US010497881B2

(12) United States Patent
Hirai

(10) Patent No.: US 10,497,881 B2
(45) Date of Patent: Dec. 3, 2019

(54) ORGANIC SEMICONDUCTOR ELEMENT, MANUFACTURING METHOD THEREOF, COMPOSITION FOR FORMING ORGANIC SEMICONDUCTOR FILM, COMPOUND, AND ORGANIC SEMICONDUCTOR FILM

(71) Applicant: FUJIFILM CORPORATION, Minato-ku, Tokyo (JP)

(72) Inventor: Yuki Hirai, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 79 days.

(21) Appl. No.: 15/497,239

(22) Filed: Apr. 26, 2017

(65) Prior Publication Data

US 2017/0229662 A1 Aug. 10, 2017

Related U.S. Application Data

(63) Continuation of application No. PCT/JP2015/082668, filed on Nov. 20, 2015.

(30) Foreign Application Priority Data

Nov. 25, 2014 (JP) .................................. 2014-237888

(51) Int. Cl.

| H01L 51/00 | (2006.01) |
| C09B 57/00 | (2006.01) |
| H01L 29/786 | (2006.01) |
| C07D 493/04 | (2006.01) |
| C07D 495/04 | (2006.01) |
| H01L 51/05 | (2006.01) |

(52) U.S. Cl.
CPC ........ H01L 51/0074 (2013.01); C07D 493/04 (2013.01); C07D 495/04 (2013.01); C09B 57/00 (2013.01); H01L 29/786 (2013.01); H01L 51/0035 (2013.01); H01L 51/0068 (2013.01); H01L 51/0073 (2013.01); H01L 51/0004 (2013.01); H01L 51/0005 (2013.01); H01L 51/0541 (2013.01); H01L 51/0545 (2013.01); H01L 51/0558 (2013.01)

(58) Field of Classification Search
CPC .................................................. H01L 51/0074
See application file for complete search history.

(56) References Cited

U.S. PATENT DOCUMENTS

2015/0014673 A1 * 1/2015 Takeya ................. C07D 333/50
257/40

FOREIGN PATENT DOCUMENTS

| JP | 2010-177637 A | 8/2010 |
| WO | 2013/168048 A1 | 11/2013 |
| WO | WO-2013168048 A1 * | 11/2013 ........... C07D 333/52 |

OTHER PUBLICATIONS

Kwon, O., et al. "Vibronic Coupling in Organic Semiconductors: The Case of Fused Polycyclic Benzene-Thiophene Structures." Chem. Eur. J. (2006), vol. 12, pp. 2073-2080.*
ChemSpider. "O-Xylene." (Nov. 8, 2012). Accessed Dec. 15, 2018. Available from: < https://web.archive.org/web/20121108175027/http://www.chemspider.com/Chemical-Structure.6967.html > . (Year: 2012).*
Kwon, O., et al. "Vibronic Coupling in Organic Semiconductors: The Case of Fused Polycyclic Benzene-Thiophene Structures." Chem. Eur. J. (2006), vol. 12, pp. 2073-2080. (Year: 2006).*

* cited by examiner

*Primary Examiner* — Andrew D Kosar
*Assistant Examiner* — John S Kenyon
(74) *Attorney, Agent, or Firm* — Solaris Intellectual Property Group, PLLC

(57) ABSTRACT

An object to be achieved by the present invention is to provide an organic semiconductor element and an organic semiconductor film having high mobility and excellent heat resistance, and a manufacturing method thereof, to provide a novel compound that is suitable as an organic semiconductor, and to provide a composition for forming an organic semiconductor film in which coating film formability is excellent, with which an organic semiconductor element that has high mobility can be obtained, and in which heat resistance is excellent, an organic semiconductor element in which the composition for forming an organic semiconductor film is used, and a manufacturing method thereof.

The organic semiconductor element according to the present invention includes a compound represented by Formula 1 below included in an organic semiconductor layer.

(1)

[Chemical structure showing fused polycyclic compound with labels $Z^{1a}$, $Z^{1b}$, $Z^{1c}$, $Z^{1d}$, $Z^{1e}$, $Z^{1f}$, $Z^{1g}$, $Z^{1h}$, $Z^{1i}$, $Z^{1j}$, $X^{11}$, $X^{12}$, $A^{11}$, $A^{12}$, $(R^{11})_{p1}$, $(R^{12})_{q1}$, $n1$]

39 Claims, 1 Drawing Sheet

ORGANIC SEMICONDUCTOR ELEMENT, MANUFACTURING METHOD THEREOF, COMPOSITION FOR FORMING ORGANIC SEMICONDUCTOR FILM, COMPOUND, AND ORGANIC SEMICONDUCTOR FILM

CROSS-REFERENCE TO RELATED APPLICATION

This application is a continuation application of International Application No. PCT/JP2015/082668, filed Nov. 20, 2015, the disclosure of which is incorporated herein by reference in its entirety. Further, this application claims priority from Japanese Patent Application No. 2014-237888, filed Nov. 25, 2014, the disclosure of which is incorporated herein by reference in its entirety.

BACKGROUND OF THE INVENTION

1. Field of the Invention

The present invention relates to an organic semiconductor element, a manufacturing method thereof, a composition for forming an organic semiconductor film, a compound, and an organic semiconductor film.

2. Description of the Related Art

An organic transistor having an organic semiconductor film (organic semiconductor layer) is used in a field effect transistor (FET) used in a liquid crystal display or an organic electroluminescence (EL) display, Radio Frequency Identifier (RFID, RF tag), and the like, because lightening of weight, cost reduction and flexibilization can be achieved.

As the organic semiconductor in the related art, those disclosed in JP2010-177637A and WO2013/168048A are known.

SUMMARY OF THE INVENTION

An object to be achieved by the present invention is to provide an organic semiconductor element and an organic semiconductor film having high mobility and excellent heat resistance, and a manufacturing method thereof.

Another object to be achieved by the present invention is to provide a novel compound that is suitable as an organic semiconductor.

Still another object to be achieved by the present invention is to provide a composition for forming an organic semiconductor film in which coating film formability is excellent, with which an organic semiconductor element that has high mobility can be obtained, and in which heat resistance is excellent, an organic semiconductor element in which the composition for forming an organic semiconductor film is used, and a manufacturing method thereof.

The objects of the present invention are solved by the means described in <1>, <17>, <34>, <35>, <37>, <38>, and <40> below. <1> to <16>, <18> to <33>, <36>, and <39> which are preferable embodiments are also described below.

<1> An organic semiconductor element comprising: a compound represented by Formula 1 below in an organic semiconductor layer,

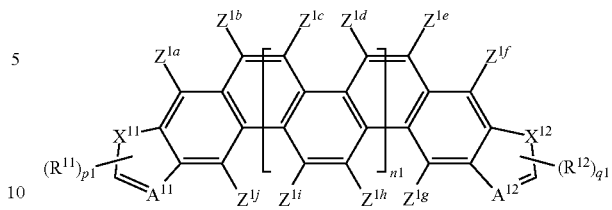

in Formula 1, $X^{11}$ and $X^{12}$ each independently represent a chalcogen atom, $Z^{1a}$ to $Z^{1j}$ each independently represent a hydrogen atom or a halogen atom, $A^{11}$ represents $=CR^{A11}-$ or a nitrogen atom, $R^{A11}$ represents a hydrogen atom or a group represented by $R^{11}$, $A^{12}$ represents $=CR^{A12}-$ or a nitrogen atom, $R^{A12}$ represents a hydrogen atom or a group represented by $R^{12}$, n1 represents 0 or 1, p1 represents an integer of 0 to 2 in a case where $A^{11}$ is $=CR^{A11}-$ and represents 0 or 1 in a case where $A^{11}$ is a nitrogen atom, q1 represents an integer of 0 to 2 in a case where $A^{12}$ is $=CR^{A12}-$ and represents 0 or 1 in a case where $A^{12}$ is a nitrogen atom, $R^{11}$ and $R^{12}$ each independently represent a halogen atom, an aryl group, a heteroaryl group, or a group represented by Formula W below, and $$-S^{W}-L^{W}-T^{W} \quad (W)$$

in Formula W, $S^{W}$ represents a single bond or an alkylene group represented by $-(CR^{S}_{2})_{k}-$, $R^{S}$ each independently represent a hydrogen atom or a halogen atom, k represents an integer of 1 to 17, $L^{W}$ represents a single bond, a divalent linking group represented by any one of Formulae L-1 to L-16 below, or a group obtained by bonding any two or more of divalent linking groups represented by Formulae L-1 to L-16 below, $T^{W}$ represents an alkyl group, a cyano group, a vinyl group, an ethynyl group, an aryl group, a heteroaryl group, an oxyethylene group, an oligooxyethylene group of which the repetition number of oxyethylene units is two or greater, an oligosiloxane group having two or more silicon atoms, or a trialkylsilyl group,

-continued (L-6)
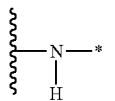

(L-7)
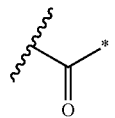

(L-8)
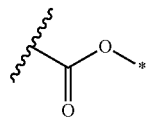

(L-9)
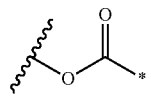

(L-10)
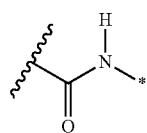

(L-11)
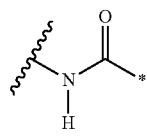

(L-12)
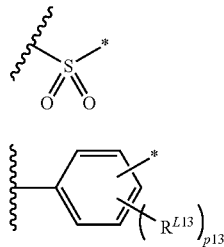

(L-13)

(L-14)
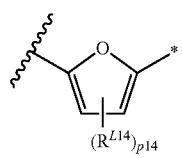

(L-15)
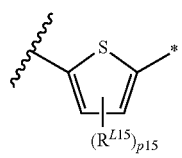

(L-16)
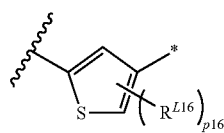

in Formulae L-1 to L-16, * and wavy line portions represent bonding positions to other structures, p13 represents an integer of 0 to 4, p14, p15, and p16 each independently represent an integer of 0 to 2, $R^{L1}$, $R^{L21}$, $R^{L22}$, $R^{L13}$, $R^{L14}$, $R^{L15}$, and $R^{L16}$ each independently represent a hydrogen atom or a substituent.

<2> The organic semiconductor element according to <1>, in which all of $Z^{1a}$ to $Z^{1j}$ are hydrogen atoms.

<3> The organic semiconductor element according to <1> or <2>, in which n1 is 0.

<4> The organic semiconductor element according to any one of <1> to <3>, in which at least one of p1 or q1 is not 0.

<5> The organic semiconductor element according to any one of <1> to <4>, in which at least one of p1 or q1 is not 0, and at least one of $R^{11}$ or $R^{12}$ is a group represented by Formula W.

<6> The organic semiconductor element according to any one of <1> to <5>, in which p1 and q1 are 1.

<7> The organic semiconductor element according to any one of <1> to <6>, in which both of $X^{11}$ and $X^{12}$ are S atoms, $A^{11}$ is $=CR^{A11}$—, and $A^{12}$ is $=CR^{A12}$—.

<8> The organic semiconductor element according to any one of <1> to <6>, in which a compound represented by Formula 1 is a compound represented by Formula 2 below, (2)

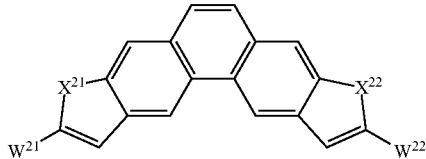

in Formula 2, $X^{21}$ and $X^{22}$ each independently represent a chalcogen atom, $W^{21}$ and $W^{22}$ each independently represent a group represented by Formula W.

<9> The organic semiconductor element according to any one of <1> to <8>, in which the compound represented by Formula 1 is a line symmetric structure.

<10> The organic semiconductor element according to any one of <1> to <9>, in which the number of carbon atoms in the group represented by Formula W is 5 to 40.

<11> The organic semiconductor element according to any one of <1> to <10>, in which $L^W$ is a single bond, a divalent linking group represented by any one of Formulae L-1 to L-4 and Formulae L-13 to L-16, or a divalent linking group obtained by bonding two or more divalent linking groups represented by any one of Formulae L-1 to L-4 and Formulae L-13 to L-16.

<12> The organic semiconductor element according to any one of <1> to <11>, in which $L^W$ is a single bond or a divalent linking group represented by any one of Formulae L-1 to L-4 and Formulae L-13 to L-16.

<13> The organic semiconductor element according to any one of <1> to <12>, in which $S^W$ is a single bond.

<14> The organic semiconductor element according to any one of <1> to <13>, in which $L^W$ is a single bond or a divalent linking group represented by any one of Formula L-1 and Formulae L-13 to L-16.

<15> The organic semiconductor element according to any one of <1> to <14>, in which $T^W$ is an alkyl group.

<16> The organic semiconductor element according to any one of <1> to <15>, in which a group represented by Formula W is an alkyl group.

<17> A composition for forming an organic semiconductor film, comprising: a solvent having a boiling point of 100° C. or higher; and a compound represented by Formula 1, in which a content of the compound represented by Formula 1 is 20 mass % or less with respect to a total amount of the composition for forming an organic semiconductor film.

<18> The composition for forming an organic semiconductor film according to <17>, in which all of $Z^{1a}$ to $Z^{1j}$ are hydrogen atoms.

<19> The composition for forming an organic semiconductor film according to <17> or <18>, in which n1 is 0.

<20> The composition for forming an organic semiconductor film according to any one of <17> to <19>, in which at least one of p1 or q1 is not 0.

<21> The composition for forming an organic semiconductor film according to any one of <17> to <20>, in which at least one of p1 or q1 is not 0, and at least one of $R^{11}$ or $R^{12}$ is a group represented by Formula W.

<22> The composition for forming an organic semiconductor film according to any one of <17> to <21>, in which p1 and q1 is 1.

<23> The composition for forming an organic semiconductor film according to any one of <17> to <22>, in which both of $X^{11}$ and $X^{12}$ are S atoms, $A^{11}$ is =$CR^{A11}$—, and $A^{12}$ is =$CR^{A12}$—.

<24> The composition for forming an organic semiconductor film according to any one of <17> to <22>, in which the compound represented by Formula 1 is a compound represented by Formula 2.

<25> The composition for forming an organic semiconductor film according to any one of <17> to <24>, in which the compound represented by Formula 1 is a line symmetric structure.

<26> The composition for forming an organic semiconductor film according to any one of <17> to <25>, in which the number of carbon atoms in the group represented by Formula W is 5 to 40.

<27> The composition for forming an organic semiconductor film according to any one of <17> to <26>, in which $L^W$ is a single bond, a divalent linking group represented by any one of Formulae L-1 to L-4 and Formulae L-13 to L-16, and a divalent linking group obtained by bonding two or more divalent linking groups represented by any one of Formulae L-1 to L-4 and Formulae L-13 to L-16.

<28> The composition for forming an organic semiconductor film according to any one of <17> to <27>, in which $L^W$ is a single bond or a divalent linking group represented by any one of Formulae L-1 to L-4 and Formulae L-13 to L-16.

<29> The composition for forming an organic semiconductor film according to any one of <17> to <28>, in which $S^W$ is a single bond.

<30> The composition for forming an organic semiconductor film according to any one of <17> to <29>, in which $L^W$ is a single bond or a divalent linking group represented by any one of Formula L-1 and Formulae L-13 to L-16.

<31> The composition for forming an organic semiconductor film according to any one of <17> to <30>, in which $T^W$ is an alkyl group.

<32> The composition for forming an organic semiconductor film according to any one of <17> to <31>, in which a group represented by Formula W is an alkyl group.

<33> The composition for forming an organic semiconductor film according to any one of <17> to <32>, further comprising: a binder polymer, in which a content of the binder polymer is 10 mass % or less with respect to a total amount of the composition for forming an organic semiconductor film.

<34> A compound represented by Formula 1.

<35> A method of manufacturing an organic semiconductor film, comprising: an applying step of applying the composition for forming an organic semiconductor film according to any one of <17> to <33> to a substrate, and a removing step of removing at least a portion of the solvent having a boiling point of 100° C. or higher included in the composition for forming an organic semiconductor film.

<36> The method of manufacturing the organic semiconductor film according to <35>, in which the applying step is performed by an ink jet method or a flexographic printing method.

<37> An organic semiconductor film obtained by the method according to <35> or <36>.

<38> A method of manufacturing an organic semiconductor element, comprising: an applying step of applying the composition for forming an organic semiconductor film according to any one of <17> to <33> to a substrate, and a removing step of removing at least a portion of the solvent having a boiling point of 100° C. or higher included in the composition for forming an organic semiconductor film.

<39> The method of manufacturing the organic semiconductor element according to <38>, in which the applying step is performed by an ink jet method or a flexographic printing method.

<40> An organic semiconductor element manufactured by the method according to <38> or <39>.

According to the present invention, it is possible to provide an organic semiconductor element and an organic semiconductor film having high mobility and excellent heat resistance, and a manufacturing method thereof.

According to the present invention, it is possible to provide a novel compound that is suitable as an organic semiconductor.

According to the present invention, it is possible to provide a composition for forming an organic semiconductor film in which coating film formability is excellent, with which an organic semiconductor element that has high mobility can be obtained, and in which heat resistance is excellent, an organic semiconductor element in which the composition for forming an organic semiconductor film is used, and a manufacturing method thereof.

DESCRIPTION OF THE PREFERRED EMBODIMENTS

Figure 1:
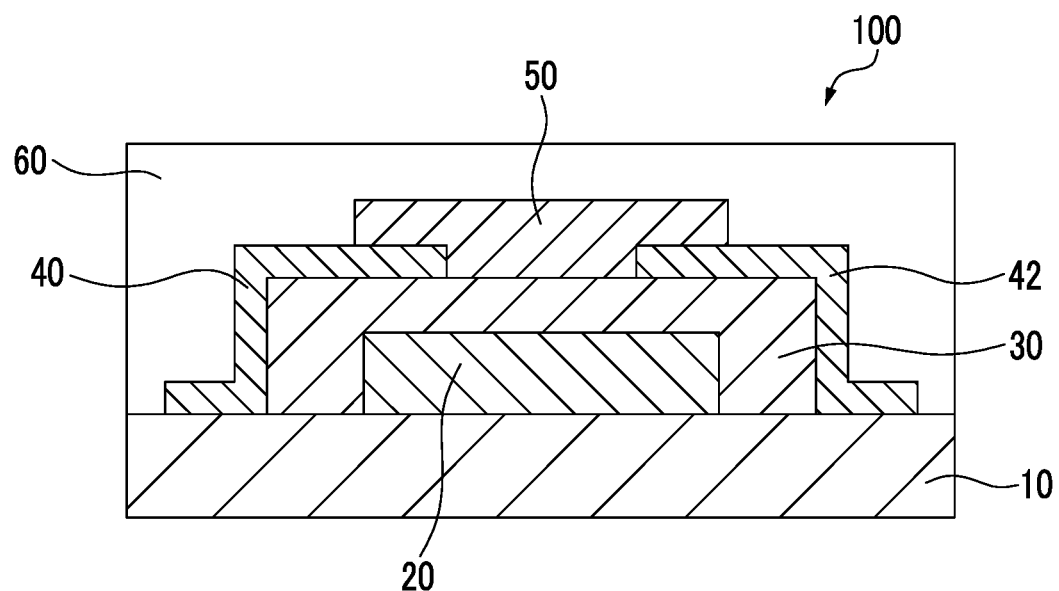
FIG. 1 is a schematic cross-sectional view of an aspect of an organic semiconductor element of the present invention.

Hereinafter, the contents of the present invention will be specifically described. The constituents in the following description will be explained based on typical embodiments of the present invention, but the present invention is not limited to the embodiments. In the specification of the present application, "to" is used to mean that the numerical values listed before and after "to" are a lower limit and an upper limit respectively. Furthermore, in the present invention, an organic EL element refers to an organic electroluminescence element.

In the present specification, in a case where there is no description regarding whether a group (atomic group) is substituted or unsubstituted, the group includes both of a group having a substituent and a group not having a substituent. For example, an "alkyl group" includes not only an alkyl group not having a substituent (unsubstituted alkyl group) but also an alkyl group having a substituent (substituted alkyl group).

In the present specification, in some cases, a chemical structural formula is described as a simplified structural formula in which a hydrogen atom is omitted.

In the present invention, "mass %" and "weight %" have the same definition, and "part by mass" and "part by weight" have the same definition.

In the present invention, a combination of preferred aspects is more preferable.

(Organic Semiconductor Element and Compound)

The organic semiconductor element according to the present invention includes a compound (hereinafter, referred to as a "specific compound") represented by Formula 1 above in an organic semiconductor layer.

The compound represented by Formula 1 above is preferably an organic semiconductor compound.

As a result of diligent research, the present inventors found that an organic semiconductor element or an organic semiconductor film containing the compound represented by Formula 1 has high mobility and excellent heat resistance, so as to complete the present invention.

A specific mechanism for exhibiting the effect is not clear, but it is assumed that if the compound represented by Formula 1 has line symmetry with a molecular center as an axis of symmetry in a certain degree or greater, mobility improves since crystallinity becomes excellent, and heat resistance of the organic semiconductor element is improved since a melting point increases.

It is assumed that crystallinity is excellent and mobility is improved, since the compound represented by Formula 1 has a molecular shape that the terminal thiophene ring protrudes from a rod-like structure such as a phenanthrene structure or a picene structure, and the appearance of a liquid crystal layer is suppressed. The mechanism of the suppression of the appearance of the liquid crystal layer as above contributes to the improvement of the heat resistance of the organic semiconductor element.

<Specific Compound>

The specific compound according to the present invention is represented by Formula 1 below.

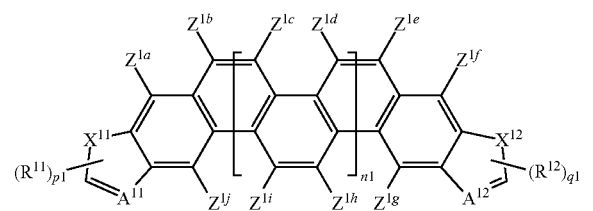

(1)

In Formula 1, $X^{11}$ and $X^{12}$ each independently represent a chalcogen atom, $Z^{1a}$ to $Z^{1j}$ each independently represent a hydrogen atom or a halogen atom, $A^{11}$ represents $=CR^{411}—$ or a nitrogen atom, $R^{411}$ represents a hydrogen atom or a group represented by $R^{11}$, $A^{12}$ represents $=CR^{412}—$ or a nitrogen atom, $R^{412}$ represents a hydrogen atom or a group represented by $R^{12}$, n1 represents 0 or 1, p1 represents an integer of 0 to 2 in a case where $A^{11}$ is $=CR^{411}—$ and represents 0 or 1 in a case where $A^{11}$ is a nitrogen atom, q1 represents an integer of 0 to 2 in a case where $A^{12}$ is $=CR^{412}—$ and represents 0 or 1 in a case where $A^{12}$ is a nitrogen atom, $R^{11}$ and $R^{12}$ each independently represent a halogen atom, an aryl group, a heteroaryl group, or a group represented by Formula W below.

(W)

In Formula W, $S^W$ represents a single bond or an alkylene group represented by $—(CR^S{}_2)_k—$, $R^S$ each independently represent a hydrogen atom or a halogen atom, k represents an integer of 1 to 17, $L^W$ represents a single bond, a divalent linking group represented by any one of Formulae L-1 to L-16 below, or a group obtained by bonding any two or more of divalent linking groups represented by Formulae L-1 to L-16 below, $T^W$ represents an alkyl group, a cyano group, a vinyl group, an ethynyl group, an aryl group, a heteroaryl group, an oxyethylene group, an oligooxyethylene group of which the repetition number of oxyethylene units is two or greater, an oligosiloxane group having two or more silicon atoms, or a trialkylsilyl group.

(L-1)

(L-2)

(L-3)

(L-4)

(L-5)

(L-6)

(L-7)

(L-8)

(L-9)

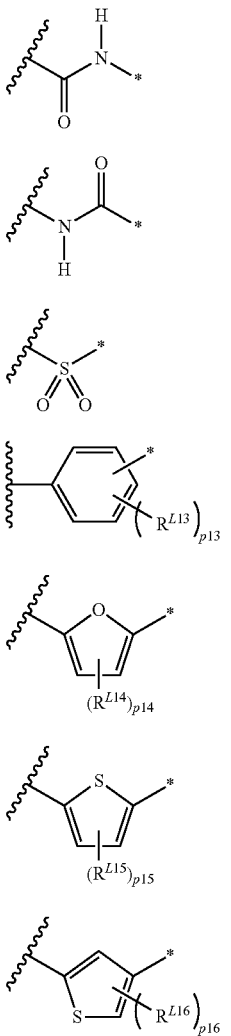

In Formulae L-1 to L-16, * and wavy line portions represent bonding positions to other structures, p13 represents an integer of 0 to 4, p14, p15, and p16 each independently represent an integer of 0 to 2, $R^{L1}$, $R^{L21}$, $R^{L22}$, $R^{L13}$, $R^{L14}$, $R^{L15}$, and $R^{L16}$ each independently represent a hydrogen atom or a substituent.

The specific compound according to the present invention is preferably an organic semiconductor compound.

The specific compound according to the present invention is a novel compound.

The specific compound according to the present invention can be suitably used for an organic semiconductor element, an organic semiconductor film, and a composition for forming an organic semiconductor film.

In Formula 1, $X^{11}$ and $X^{12}$ each independently represent a chalcogen atom, it is preferable that $X^{11}$ and $X^{12}$ each independently represent an O atom or an S atom, and it is more preferable that both of $X^{11}$ and $X^{12}$ are S atoms. The chalcogen atom refers to an atom in Group 16 including an O atom.

$Z^{1a}$ to $Z^{1j}$ each independently represent a hydrogen atom or a halogen atom, and it is preferable that all of $Z^{1a}$ to $Z^{1j}$ are hydrogen atoms.

Examples of the halogen atom include a fluorine atom, a chlorine atom, a bromine atom, and an iodine atom, and a fluorine atom is preferable.

$A^{11}$ represents $=CR^{A11}-$ or an nitrogen atom, and $=CR^{A11}-$ is preferable.

$R^{A11}$ represents a hydrogen atom or a group represented by $R^{11}$, and a hydrogen atom is preferable. The expression "$R^{A11}$ represents a group represented by $R^{11}$" refers to a case where one of $R^{11}$'s of which the number is specified by p1 in Formula 1 is bonded to a carbon atom in $A^{11}$.

$A^{12}$ represents $=CR^{A12}-$ or a nitrogen atom, and $=CR^{A12}-$ is preferable.

$R^{A12}$ represents a hydrogen atom or a group represented by $R^{12}$, and a hydrogen atom is preferable. The expression "$R^{A12}$ represents a group represented by $R^{12}$" refers to a case where one of $R^{12}$'s of which the number is specified by q1 in Formula 1 is bonded to a carbon atom in $A^2$.

n1 represents 0 or 1 and preferably 0.

In a case where $A^{11}$ is $=CR^{A11}-$, p1 represents an integer of 0 to 2, preferably represents 1 or 2, more preferably 1. In a case where $A^{11}$ is a nitrogen atom, p1 represents 0 or 1 and preferably represents 1. In a case where $A^{11}$ is $=CR^{A11}-$, and p1 is 1, $R^{11}$ is preferably bonded to a carbon atom positioned between $A^{11}$ and $X^{11}$, not a carbon atom included in $A^{11}$.

In a case where $A^{12}$ is $=CR^{A12}-$, q1 represents an integer of 0 to 2, preferably represents 1 or 2, and more preferably represents 1. In a case where $A^{12}$ is a nitrogen atom, q1 represents 0 or 1 and preferably represents 1. In a case where $A^{12}$ is $=CR^{A12}-$ and q1 is 1, $R^{12}$ is preferably bonded to a carbon atom positioned between $A^{12}$ and $X^{12}$, not a carbon atom included in $A^{12}$.

$R^{11}$ and $R^{12}$ each independently represent a halogen atom, an aryl group, a heteroaryl group, or a group represented by Formula W below and preferably represents a group represented by Formula W.

$$-S^W-L^W-T^W \qquad (W)$$

In Formula W, $S^W$ represents a single bond or an alkylene group represented by $-(CR^S_2)_k-$ and preferably represents a single bond.

$R^S$ each independently represent a hydrogen atom or a halogen atom and preferably a hydrogen atom.

k represents an integer of 1 to 17, preferably represents an integer of 1 to 15, and more preferably an integer of 1 to 10.

$L^W$ represents a single bond, a divalent linking group represented by any one of Formulae L-1 to L-16, or a group obtained by bonding any two or more of divalent linking groups represented by Formulae L-1 to L-16, preferably represents a single bond, a divalent linking group represented by any one of Formulae L-1 to L-4 and Formulae L-13 to L-16, or a divalent linking group obtained by bonding two or more divalent linking groups represented by any one of Formulae L-1 to L-4 and Formulae L-13 to L-16, more preferably a single bond or a divalent linking group represented by any one of Formulae L-1 to L-4 and Formulae L-13 to L-16, and even more preferably a divalent linking group represented by any one of Formulae L-1, L-3, L-15, and L-16.

$L^W$ preferably represents a single bond or a divalent linking group represented by any one of Formula L-1 and Formulae L-13 to L-16.

$T^W$ represented by an alkyl group, a cyano group, a vinyl group, an ethynyl group, an aryl group, a heteroaryl group, an oxyethylene group, an oligooxyethylene group of which the repetition number of oxyethylene units is two or greater, an oligosiloxane group having two or more silicon atoms, or a trialkylsilyl group.

The alkyl group is preferably an alkyl group having 2 to 18 carbon atoms, more preferably an alkyl group having 3 to 15 carbon atoms, and even more preferably an alkyl group having 4 to 13 carbon atoms. The alkyl group may have any one of a linear shape, a branched shape, or a cyclic shape, or may have a structure obtained by combining these. However, a linear or branched alkyl group is preferable, and a linear alkyl group is more preferable.

The alkyl group may be substituted and preferable examples of the substituent include a halogen atom.

Examples of the aryl group (an aromatic hydrocarbon group) include a group obtained by removing one hydrogen atom from benzene, naphthalene, anthracene, or the like. A group obtained by removing one hydrogen atom from benzene is preferable.

The aryl group may be substituted but is preferably not substituted.

Examples of a heteroatom included in a heteroaryl group (an aromatic heterocyclic group) include an oxygen atom, a nitrogen atom, and a sulfur atom. An oxygen atom and a sulfur atom are preferable, and a sulfur atom is more preferable.

Examples of the heteroaryl group include a group obtained by removing one hydrogen atom from a thiophene ring, a furan ring, a pyran ring, a pyrrole ring, a pyridine ring, a pyrazine ring, a pyrimidine ring, a pyridazine ring, a selenophene ring, an imidazole ring, and the like. A group obtained by removing one hydrogen atom from a thiophene ring or a furan ring is more preferable, and a group obtained by removing one hydrogen atom from a thiophene ring is even more preferable.

The heteroaryl group may be further substituted, but it is preferable that the heteroaryl group is not substituted.

The oligooxyethylene group of which the repetition number of oxyethylene units is two or greater is preferably an oligooxyethylene group of which the repetition number is one to five and more preferably an oligooxyethylene group of which the repetition number is one to three.

The oligosiloxane group having two or more silicon atoms is preferably an oligosiloxane group having one to five silicon atoms and more preferably an oligosiloxane group having one to three silicon atoms.

In Formulae L-1 to L-16, it is preferable that wavy line portions represent bonding positions to $S^W$, * represents a bonding position to $T^W$ or a bonding position to a divalent linking group selected from the group consisting of other L-1 to L-16.

p13 represents an integer of 0 to 4, p14, p15, and p16 each independently represent an integer of 0 to 2, and $R^{L1}$, $R^{L21}$, $R^{L22}$, $R^{L13}$, $R^{L14}$, $R^{L15}$, and $R^{L16}$ each independently represent a hydrogen atom or a substituent.

In a case where $L^W$ represents a linking group obtained by bonding a divalent linking group represented by any one of Formulae L-1 to L-16 above, the number of linkages of the divalent linking groups represented by any one of Formulae L-1 to L-16 is preferably 2 to 4 and more preferably 2 or 3.

$R^{L1}$, $R^{L21}$, $R^{L22}$, $R^{L13}$, $R^{L14}$, $R^{L15}$, and $R^{L16}$ each independently represent a hydrogen atom or a substituent and preferably represent a hydrogen atom. Examples of the substituent include various substituents exemplified as $T^W$ in Formula 1 above.

A plurality of $R^{L1}$'s, $R^{L13}$'s, $R^{L14}$'s, $R^{L15}$'s, and $R^{L16}$'s may be identical to or different from each other. $R^{L1}$'s, $R^{L21}$'s, and $R^{L22}$'s may form ring structures by being bonded to $T^W$ adjacent to each other or may form a fused ring as the ring structure.

The group represented by Formula W is preferably an alkyl group, more preferably an alkyl group having 2 to 18 carbon atoms, even more preferably an alkyl group having 3 to 15 carbon atoms, and particularly preferably an alkyl group having 4 to 13 carbon atoms. In a case where the group represented by Formula W is an alkyl group, it is preferable that $S^W$ and $L^W$ are single bonds, and $T^W$ is an alkyl group.

In Formula 1, it is preferable that at least one of p1 or q1 is not 0, and it is more preferable that at least one of p1 or q1 is not 0, and at least one of $R^{11}$ or $R^{12}$ is a group represented by Formula W.

In Formula 1, it is preferable that p1 and q1 are 1, it is more preferable that p1 and q1 are 1, and at least one of $R^{11}$ or $R^{12}$ is a group represented by Formula W, and it is even more preferable that p1 and q1 are 1, and both of $R^{11}$ and $R^{12}$ are groups represented by Formula W.

In Formula 1, it is preferable that both of $X^{11}$ and $X^{12}$ are S atoms, $A^{11}$ is $=CR^{A11}—$, and $A^{12}$ is $=CR^{A12}—$, it is more preferable that both of $X^{11}$ and $X^{12}$ are S atoms, $A^{11}$ is $=CR^{A11}—$, $A^{12}$ is $=CR^{A12}—$, and both of $R^{A11}$ and $R^{A12}$ are hydrogen atoms.

The compound represented by Formula 1 is preferably a compound represented by Formula 2 below.

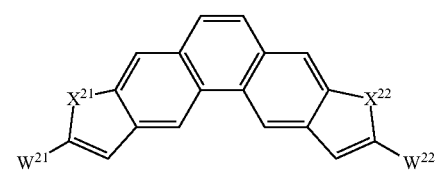

(2)

In Formula 2, $X^{21}$ and $X^{22}$ each independently represent a chalcogen atom, preferably an O atom or a S atom. It is more preferable that both of $X^{21}$ and $X^{22}$ are S atoms. $W^{21}$ and $W^{22}$ each independently represent a group represented by Formula W above, and a preferable aspect thereof is the same as the preferable aspect described in the group represented by Formula W above.

The compound represented by Formula 1 above is preferably a line symmetric structure.

The expression "a compound has a line symmetric structure" means that a structural formula thereof is line symmetric with respect to the entire molecule. Specifically, the compound represented by Formula 1 is preferably a compound represented by Formulae 3 to 5 below.

It is considered that, if the compound represented by Formula 1 has a line symmetric structure, crystallinity and melting point become high, and mobility or heat resistance of an obtained organic semiconductor element or an obtained organic semiconductor film increase.

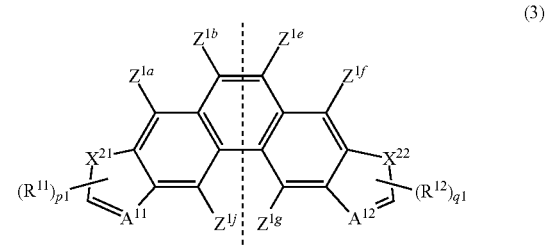

(3)

-continued

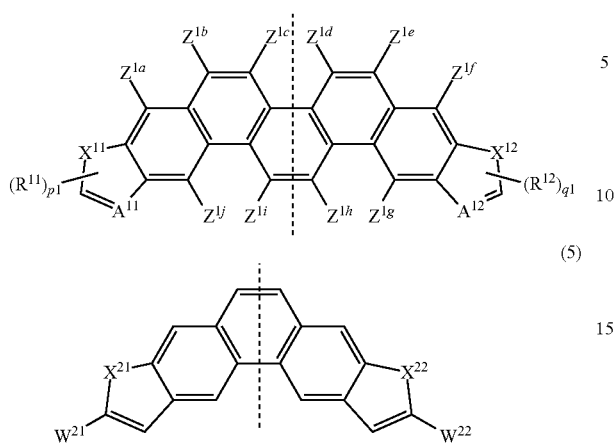

(4)

(5)

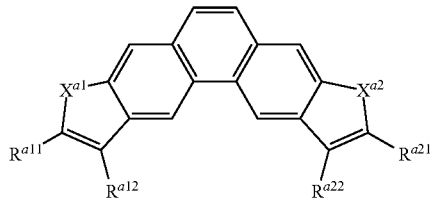

(a)

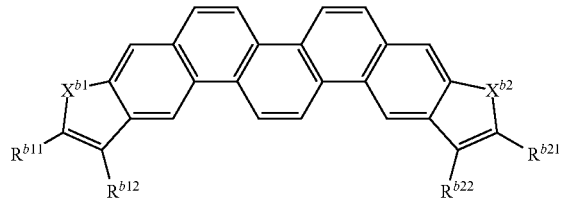

(b)

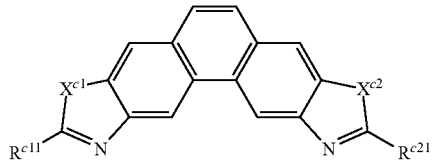

(c)

In Formula 3 or 4, $X^{11}$, $X^{12}$, $Z^{1a}$ to $Z^{1j}$, $A^{11}$, $A^{12}$, p1, q1, $R^{11}$, and $R^{12}$ have the same meaning as $X^{11}$, $X^{12}$, $Z^{1a}$ to $Z^{1j}$, $A^{11}$, $A^{12}$, p1, q1, $R^{11}$, and $R^{12}$ in Formula 1, and preferable aspects thereof are also the same.

In Formula 5, $X^{21}$, $X^{22}$, $W^{21}$, and $W^{22}$ have the same meaning as $X^{21}$, $X^{22}$, $W^{21}$, and $W^{22}$ in Formula 2, and preferable aspects thereof are also the same.

All of the compounds represented by Formulae 3 to 5 have line symmetry having broken lines as symmetry axes.

As specific examples of the specific compound used in the present invention, Compounds 1 to 1475 represented by Formulae a to c below and presented in Tables 1 to 59 are preferably exemplified. However, the present invention is not limited thereto.

In Compounds 1 to 1475, $X^{a1}$, $X^{a2}$, $R^{a11}$, $R^{a12}$, $R^{a21}$, $R^{a22}$, $X^{b1}$, $X^{b2}$, $R^{b11}$, $R^{b12}$, $R^{b21}$, $R^{b22}$, $X^{c1}$, $X^{c2}$, $R^{c11}$, and $R^{c21}$ in Formulae a to c represent structures presented in Tables 1 to 59. In Tables 1 to 59, Ph represents a phenyl group, -Ph- represents a phenylene group, and * represents a bonding portion to another structure.

TABLE 1

| | $X^{a1}$ | $X^{a2}$ | $R^{a11}$ | $R^{a12}$ | $R^{a21}$ | $R^{a22}$ |
|---|---|---|---|---|---|---|
| Compound 1 | S | S | $C_4H_9$—* | H | $C_4H_9$—* | H |
| Compound 2 | S | S | $C_5H_{11}$—* | H | $C_5H_{11}$—* | H |
| Compound 3 | S | S | $C_6H_{13}$—* | H | $C_6H_{13}$—* | H |
| Compound 4 | S | S | $C_7H_{15}$—* | H | $C_7H_{15}$—* | H |
| Compound 5 | S | S | $C_8H_{17}$—* | H | $C_8H_{17}$—* | H |
| Compound 6 | S | S | $C_9H_{19}$—* | H | $C_9H_{19}$—* | H |
| Compound 7 | S | S | $C_{10}H_{21}$—* | H | $C_{10}H_{21}$—* | H |
| Compound 8 | S | S | $C_{11}H_{23}$—* | H | $C_{11}H_{23}$—* | H |
| Compound 9 | S | S | $C_{12}H_{25}$—* | H | $C_{12}H_{25}$—* | H |
| Compound 10 | S | S | $C_{13}H_{27}$—* | H | $C_{13}H_{27}$—* | H |
| Compound 11 | S | S | $C_{14}H_{29}$—* | H | $C_{14}H_{29}$—* | H |
| Compound 12 | S | S | $C_{15}H_{31}$—* | H | $C_{15}H_{31}$—* | H |
| Compound 13 | S | S | $C_{16}H_{33}$—* | H | $C_{16}H_{33}$—* | H |
| Compound 14 | S | S | $C_{17}H_{35}$—* | H | $C_{17}H_{35}$—* | H |
| Compound 15 | S | S | $C_{18}H_{37}$—* | H | $C_{18}H_{37}$—* | H |
| Compound 16 | S | S | $C_5H_{11}$—* | $C_5H_{11}$—* | $C_5H_{11}$—* | $C_5H_{11}$—* |
| Compound 17 | S | S | $C_6H_{13}$—* | $C_6H_{13}$—* | $C_6H_{13}$—* | $C_6H_{13}$—* |
| Compound 18 | S | S | $C_7H_{15}$—* | $C_7H_{15}$—* | $C_7H_{15}$—* | $C_7H_{15}$—* |
| Compound 19 | S | S | $C_8H_{17}$—* | $C_8H_{17}$—* | $C_8H_{17}$—* | $C_8H_{17}$—* |
| Compound 20 | S | S | $C_9H_{19}$—* | $C_9H_{19}$—* | $C_9H_{19}$—* | $C_9H_{19}$—* |
| Compound 21 | S | S | $C_{10}H_{21}$—* | $C_{10}H_{21}$—* | $C_{10}H_{21}$—* | $C_{10}H_{21}$—* |
| Compound 22 | S | S | $C_{11}H_{23}$—* | $C_{11}H_{23}$—* | $C_{11}H_{23}$—* | $C_{11}H_{23}$—* |
| Compound 23 | S | S | $C_{12}H_{25}$—* | $C_{12}H_{25}$—* | $C_{12}H_{25}$—* | $C_{12}H_{25}$—* |
| Compound 24 | S | S | $C_{13}H_{27}$—* | $C_{13}H_{27}$—* | $C_{13}H_{27}$—* | $C_{13}H_{27}$—* |
| Compound 25 | S | S | $C_{14}H_{29}$—* | $C_{14}H_{29}$—* | $C_{14}H_{29}$—* | $C_{14}H_{29}$—* |
| Compound 26 | S | S | $C_{15}H_{31}$—* | $C_{15}H_{31}$—* | $C_{15}H_{31}$—* | $C_{15}H_{31}$—* |
| Compound 27 | S | S | $C_{16}H_{33}$—* | $C_{16}H_{33}$—* | $C_{16}H_{33}$—* | $C_{16}H_{33}$—* |
| Compound 28 | S | S | $C_{17}H_{35}$—* | $C_{17}H_{35}$—* | $C_{17}H_{35}$—* | $C_{17}H_{35}$—* |
| Compound 29 | S | S | $C_{18}H_{37}$—* | $C_{18}H_{37}$—* | $C_{18}H_{37}$—* | $C_{18}H_{37}$—* |
| Compound 30 | S | S | p-$C_5H_{11}$—Ph—* | H | p-$C_5H_{11}$—Ph—* | H |
| Compound 31 | S | S | p-$C_6H_{13}$—Ph—* | H | p-$C_6H_{13}$—Ph—* | H |
| Compound 32 | S | S | p-$C_7H_{15}$—Ph—* | H | p-$C_7H_{15}$—Ph—* | H |
| Compound 33 | S | S | p-$C_8H_{17}$—Ph—* | H | p-$C_8H_{17}$—Ph—* | H |
| Compound 34 | S | S | p-$C_9H_{19}$—Ph—* | H | p-$C_9H_{19}$—Ph—* | H |

TABLE 1-continued

|  | $X^{a1}$ | $X^{a2}$ | $R^{a11}$ | $R^{a12}$ | $R^{a21}$ | $R^{a22}$ |
|---|---|---|---|---|---|---|
| Compound 35 | S | S | p-C$_{10}$H$_{21}$—Ph—* | H | p-C$_{10}$H$_{21}$—Ph—* | H |
| Compound 36 | S | S | p-C$_{11}$H$_{23}$—Ph—* | H | p-C$_{11}$H$_{23}$—Ph—* | H |
| Compound 37 | S | S | p-C$_{12}$H$_{25}$—Ph—* | H | p-C$_{12}$H$_{25}$—Ph—* | H |
| Compound 38 | S | S | p-C$_{13}$H$_{27}$—Ph—* | H | p-C$_{13}$H$_{27}$—Ph—* | H |
| Compound 39 | S | S | p-C$_{14}$H$_{29}$—Ph—* | H | p-C$_{14}$H$_{29}$—Ph—* | H |
| Compound 40 | S | S | p-C$_{15}$H$_{31}$—Ph—* | H | p-C$_{15}$H$_{31}$—Ph—* | H |
| Compound 41 | S | S | p-C$_{16}$H$_{33}$—Ph—* | H | p-C$_{16}$H$_{33}$—Ph—* | H |
| Compound 42 | S | S | p-C$_{17}$H$_{35}$—Ph—* | H | p-C$_{17}$H$_{35}$—Ph—* | H |
| Compound 43 | S | S | p-C$_{18}$H$_{37}$—Ph—* | H | p-C$_{18}$H$_{37}$—Ph—* | H |
| Compound 44 | S | S | p-C$_5$H$_{11}$—Ph—* | p-C$_5$H$_{11}$—Ph—* | p-C$_5$H$_{11}$—Ph—* | p-C$_5$H$_{11}$—Ph—* |
| Compound 45 | S | S | p-C$_6$H$_{13}$—Ph—* | p-C$_6$H$_{13}$—Ph—* | p-C$_6$H$_{13}$—Ph—* | p-C$_6$H$_{13}$—Ph—* |
| Compound 46 | S | S | p-C$_7$H$_{15}$—Ph—* | p-C$_7$H$_{15}$—Ph—* | p-C$_7$H$_{15}$—Ph—* | p-C$_7$H$_{15}$—Ph—* |
| Compound 47 | S | S | p-C$_8$H$_{17}$—Ph—* | p-C$_8$H$_{17}$—Ph—* | p-C$_8$H$_{17}$—Ph—* | p-C$_8$H$_{17}$—Ph—* |
| Compound 48 | S | S | p-C$_9$H$_{19}$—Ph—* | p-C$_9$H$_{19}$—Ph—* | p-C$_9$H$_{19}$—Ph—* | p-C$_9$H$_{19}$—Ph—* |
| Compound 49 | S | S | p-C$_{10}$H$_{21}$—Ph—* | p-C$_{10}$H$_{21}$—Ph—* | p-C$_{10}$H$_{21}$—Ph—* | p-C$_{10}$H$_{21}$—Ph—* |
| Compound 50 | S | S | p-C$_{11}$H$_{23}$—Ph—* | p-C$_{11}$H$_{23}$—Ph—* | p-C$_{11}$H$_{23}$—Ph—* | p-C$_{11}$H$_{23}$—Ph—* |
| Compound 51 | S | S | p-C$_{12}$H$_{25}$—Ph—* | p-C$_{12}$H$_{25}$—Ph—* | p-C$_{12}$H$_{25}$—Ph—* | p-C$_{12}$H$_{25}$—Ph—* |

TABLE 2

|  | $X^{a1}$ | $X^{a2}$ | $R^{a11}$ | $R^{a12}$ | $R^{a21}$ | $R^{a22}$ |
|---|---|---|---|---|---|---|
| Compound 52 | S | S | p-C$_{13}$H$_{27}$—Ph—* | p-C$_{13}$H$_{27}$—Ph—* | p-C$_{13}$H$_{27}$—Ph—* | p-C$_{13}$H$_{27}$—Ph—* |
| Compound 53 | S | S | p-C$_{14}$H$_{29}$—Ph—* | p-C$_{14}$H$_{29}$—Ph—* | p-C$_{14}$H$_{29}$—Ph—* | p-C$_{14}$H$_{29}$—Ph—* |
| Compound 54 | S | S | p-C$_{15}$H$_{31}$—Ph—* | p-C$_{15}$H$_{31}$—Ph—* | p-C$_{15}$H$_{31}$—Ph—* | p-C$_{15}$H$_{31}$—Ph—* |
| Compound 55 | S | S | p-C$_{16}$H$_{33}$—Ph—* | p-C$_{16}$H$_{33}$—Ph—* | p-C$_{16}$H$_{33}$—Ph—* | p-C$_{16}$H$_{33}$—Ph—* |
| Compound 56 | S | S | p-C$_{17}$H$_{35}$—Ph—* | p-C$_{17}$H$_{35}$—Ph—* | p-C$_{17}$H$_{35}$—Ph—* | p-C$_{17}$H$_{35}$—Ph—* |
| Compound 57 | S | S | p-C$_{18}$H$_{37}$—Ph—* | p-C$_{18}$H$_{37}$—Ph—* | p-C$_{18}$H$_{37}$—Ph—* | p-C$_{18}$H$_{37}$—Ph—* |
| Compound 58 | S | S | 5-C$_5$H$_{11}$-thiophen-2-yl—* | H | 5-C$_5$H$_{11}$-thiophen-2-yl—* | H |
| Compound 59 | S | S | 5-C$_6$H$_{13}$-thiophen-2-yl—* | H | 5-C$_6$H$_{13}$-thiophen-2-yl—* | H |
| Compound 60 | S | S | 5-C$_7$H$_{15}$-thiophen-2-yl—* | H | 5-C$_7$H$_{15}$-thiophen-2-yl—* | H |
| Compound 61 | S | S | 5-C$_8$H$_{17}$-thiophen-2-yl—* | H | 5-C$_8$H$_{17}$-thiophen-2-yl—* | H |
| Compound 62 | S | S | 5-C$_9$H$_{19}$-thiophen-2-yl—* | H | 5-C$_9$H$_{19}$-thiophen-2-yl—* | H |
| Compound 63 | S | S | 5-C$_{10}$H$_{21}$-thiophen-2-yl—* | H | 5-C$_{10}$H$_{21}$-thiophen-2-yl—* | H |
| Compound 64 | S | S | 5-C$_{11}$H$_{23}$-thiophen-2-yl—* | H | 5-C$_{11}$H$_{23}$-thiophen-2-yl—* | H |
| Compound 65 | S | S | 5-C$_{12}$H$_{25}$-thiophen-2-yl—* | H | 5-C$_{12}$H$_{25}$-thiophen-2-yl—* | H |

TABLE 2-continued

| | $X^{a1}$ | $X^{a2}$ | $R^{a11}$ | $R^{a12}$ | $R^{a21}$ | $R^{a22}$ |
|---|---|---|---|---|---|---|
| Compound 66 | S | S | 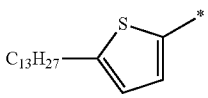 $C_{13}H_{27}$- | H | 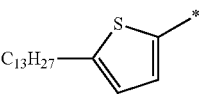 $C_{13}H_{27}$- | H |
| Compound 67 | S | S | 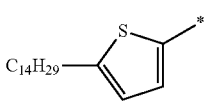 $C_{14}H_{29}$- | H | 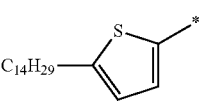 $C_{14}H_{29}$- | H |
| Compound 68 | S | S | 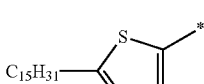 $C_{15}H_{31}$- | H | 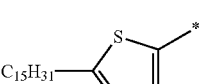 $C_{15}H_{31}$- | H |
| Compound 69 | S | S | 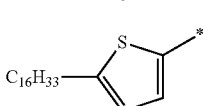 $C_{16}H_{33}$- | H | 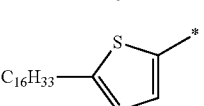 $C_{16}H_{33}$- | H |
| Compound 70 | S | S | 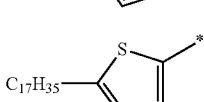 $C_{17}H_{35}$- | H | 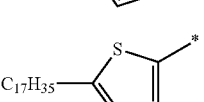 $C_{17}H_{35}$- | H |
| Compound 71 | S | S | 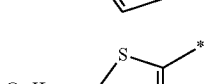 $C_{18}H_{37}$- | H | 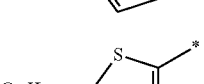 $C_{18}H_{37}$- | H |
| Compound 72 | S | S | 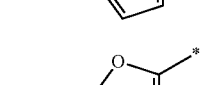 $C_5H_{11}$- | H | 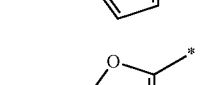 $C_5H_{11}$- | H |
| Compound 73 | S | S | 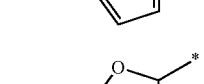 $C_6H_{13}$- | H | 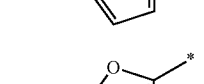 $C_6H_{13}$- | H |

TABLE 3

| | $X^{a1}$ | $X^{a2}$ | $R^{a11}$ | $R^{a12}$ | $R^{a21}$ | $R^{a22}$ |
|---|---|---|---|---|---|---|
| Compound 74 | S | S | 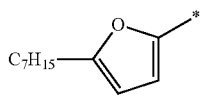 $C_7H_{15}$- | H | 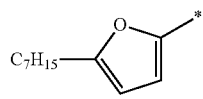 $C_7H_{15}$- | H |
| Compound 75 | S | S | 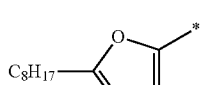 $C_8H_{17}$- | H | 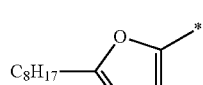 $C_8H_{17}$- | H |
| Compound 76 | S | S | 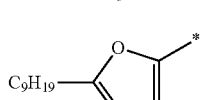 $C_9H_{19}$- | H | 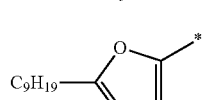 $C_9H_{19}$- | H |
| Compound 77 | S | S | 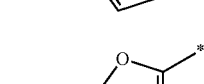 $C_{10}H_{21}$- | H | 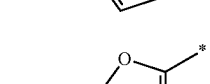 $C_{10}H_{21}$- | H |
| Compound 78 | S | S | 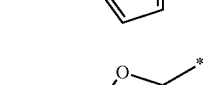 $C_{11}H_{23}$- | H | 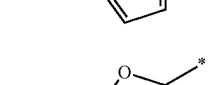 $C_{11}H_{23}$- | H |

TABLE 3-continued
| | $X^{a1}$ | $X^{a2}$ | $R^{a11}$ | $R^{a12}$ | $R^{a21}$ | $R^{a22}$ |
|---|---|---|---|---|---|---|
| Compound 79 | S | S | 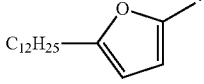 | H | 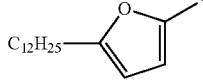 | H |
| Compound 80 | S | S | 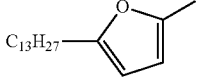 | H | 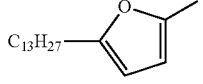 | H |
| Compound 81 | S | S | 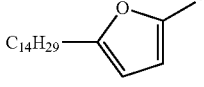 | H | 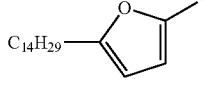 | H |
| Compound 82 | S | S | 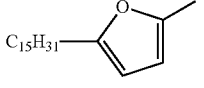 | H | 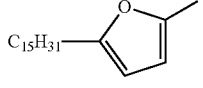 | H |
| Compound 83 | S | S | 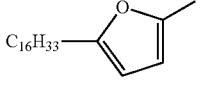 | H | 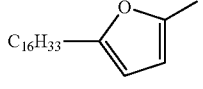 | H |
| Compound 84 | S | S | 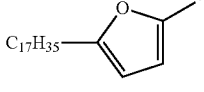 | H | 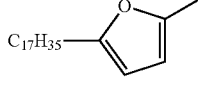 | H |
| Compound 85 | S | S | 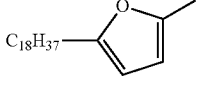 | H | 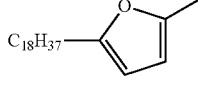 | H |
| Compound 86 | S | S | 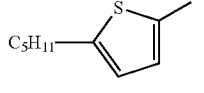 | 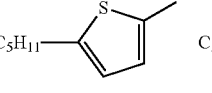 | 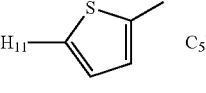 | 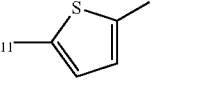 |
| Compound 87 | S | S | 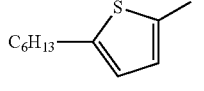 | 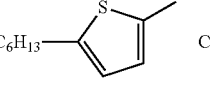 | 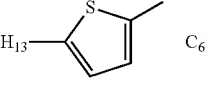 | 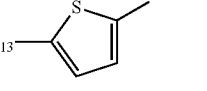 |
| Compound 88 | S | S | 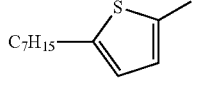 | 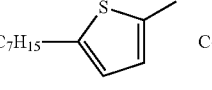 | 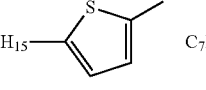 | 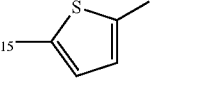 |
| Compound 89 | S | S | 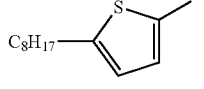 | 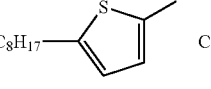 | 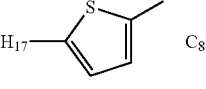 | 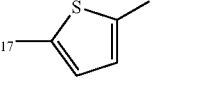 |
| Compound 90 | S | S | 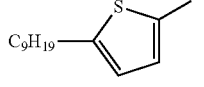 | 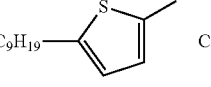 | 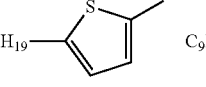 | 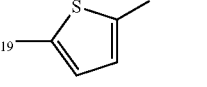 |
| Compound 91 | S | S | 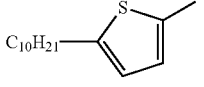 | 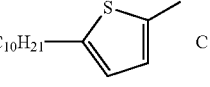 | 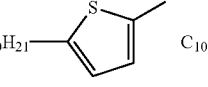 | 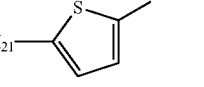 |

TABLE 4

| | $X^{a1}$ | $X^{a2}$ | $R^{a11}$ | $R^{a12}$ | $R^{a21}$ | $R^{a22}$ |
|---|---|---|---|---|---|---|
| Compound 92 | S | S | 5-C₁₁H₂₃-thiophen-2-yl | 5-C₁₁H₂₃-thiophen-2-yl | 5-C₁₁H₂₃-thiophen-2-yl | 5-C₁₁H₂₃-thiophen-2-yl |
| Compound 93 | S | S | 5-C₁₂H₂₅-thiophen-2-yl | 5-C₁₂H₂₅-thiophen-2-yl | 5-C₁₂H₂₅-thiophen-2-yl | 5-C₁₂H₂₅-thiophen-2-yl |
| Compound 94 | S | S | 5-C₁₃H₂₇-thiophen-2-yl | 5-C₁₃H₂₇-thiophen-2-yl | 5-C₁₃H₂₇-thiophen-2-yl | 5-C₁₃H₂₇-thiophen-2-yl |
| Compound 95 | S | S | 5-C₁₄H₂₉-thiophen-2-yl | 5-C₁₄H₂₉-thiophen-2-yl | 5-C₁₄H₂₉-thiophen-2-yl | 5-C₁₄H₂₉-thiophen-2-yl |
| Compound 96 | S | S | 5-C₁₅H₃₁-thiophen-2-yl | 5-C₁₅H₃₁-thiophen-2-yl | 5-C₁₅H₃₁-thiophen-2-yl | 5-C₁₅H₃₁-thiophen-2-yl |
| Compound 97 | S | S | 5-C₁₆H₃₃-thiophen-2-yl | 5-C₁₆H₃₃-thiophen-2-yl | 5-C₁₆H₃₃-thiophen-2-yl | 5-C₁₆H₃₃-thiophen-2-yl |
| Compound 98 | S | S | 5-C₁₇H₃₅-thiophen-2-yl | 5-C₁₇H₃₅-thiophen-2-yl | 5-C₁₇H₃₅-thiophen-2-yl | 5-C₁₇H₃₅-thiophen-2-yl |
| Compound 99 | S | S | 5-C₁₈H₃₇-thiophen-2-yl | 5-C₁₈H₃₇-thiophen-2-yl | 5-C₁₈H₃₇-thiophen-2-yl | 5-C₁₈H₃₇-thiophen-2-yl |
| Compound 100 | S | S | 4-C₅H₁₁-thiophen-2-yl | H | 4-C₅H₁₁-thiophen-2-yl | H |
| Compound 101 | S | S | 4-C₆H₁₃-thiophen-2-yl | H | 4-C₆H₁₃-thiophen-2-yl | H |
| Compound 102 | S | S | 4-C₇H₁₅-thiophen-2-yl | H | 4-C₇H₁₅-thiophen-2-yl | H |
| Compound 103 | S | S | 4-C₈H₁₇-thiophen-2-yl | H | 4-C₈H₁₇-thiophen-2-yl | H |
| Compound 104 | S | S | 4-C₉H₁₉-thiophen-2-yl | H | 4-C₉H₁₉-thiophen-2-yl | H |
| Compound 105 | S | S | 4-C₁₀H₂₁-thiophen-2-yl | H | 4-C₁₀H₂₁-thiophen-2-yl | H |
| Compound 106 | S | S | 4-C₁₁H₂₃-thiophen-2-yl | H | 4-C₁₁H₂₃-thiophen-2-yl | H |

TABLE 4-continued

| | $X^{a1}$ | $X^{a2}$ | $R^{a11}$ | $R^{a12}$ | $R^{a21}$ | $R^{a22}$ |
|---|---|---|---|---|---|---|
| Compound 107 | S | S | 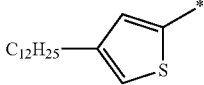 C$_{12}$H$_{25}$- | H | 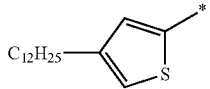 C$_{12}$H$_{25}$- | H |
| Compound 108 | S | S | 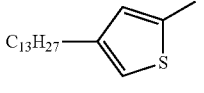 C$_{13}$H$_{27}$- | H | 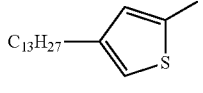 C$_{13}$H$_{27}$- | H |
| Compound 109 | S | S | 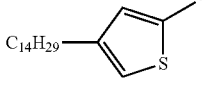 C$_{14}$H$_{29}$- | H | 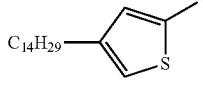 C$_{14}$H$_{29}$- | H |

TABLE 5

| | $X^{a1}$ | $X^{a2}$ | $R^{a11}$ | $R^{a12}$ | $R^{a21}$ | $R^{a22}$ |
|---|---|---|---|---|---|---|
| Compound 110 | S | S | 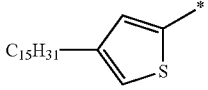 C$_{15}$H$_{31}$- | H | 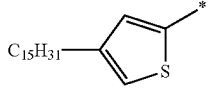 C$_{15}$H$_{31}$- | H |
| Compound 111 | S | S | 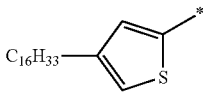 C$_{16}$H$_{33}$- | H | 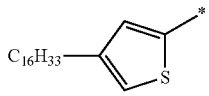 C$_{16}$H$_{33}$- | H |
| Compound 112 | S | S | 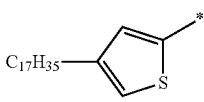 C$_{17}$H$_{35}$- | H | 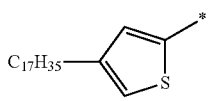 C$_{17}$H$_{35}$- | H |
| Compound 113 | S | S | 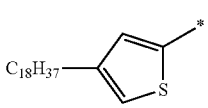 C$_{18}$H$_{37}$- | H | 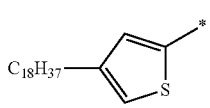 C$_{18}$H$_{37}$- | H |
| Compound 114 | S | S | 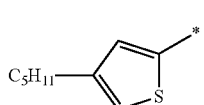 C$_5$H$_{11}$- | 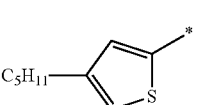 C$_5$H$_{11}$- | 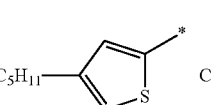 C$_5$H$_{11}$- | 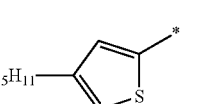 C$_5$H$_{11}$- |
| Compound 115 | S | S |  C$_6$H$_{13}$- | 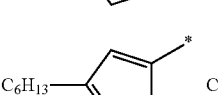 C$_6$H$_{13}$- |  C$_6$H$_{13}$- |  C$_6$H$_{13}$- |
| Compound 116 | S | S | 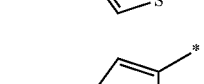 C$_7$H$_{15}$- | 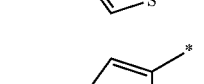 C$_7$H$_{15}$- | 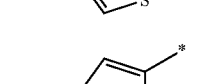 C$_7$H$_{15}$- | 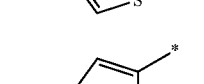 C$_7$H$_{15}$- |
| Compound 117 | S | S | 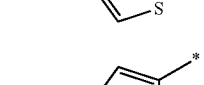 C$_8$H$_{17}$- | 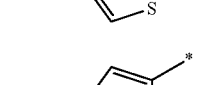 C$_8$H$_{17}$- | 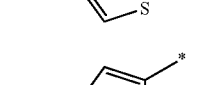 C$_8$H$_{17}$- | 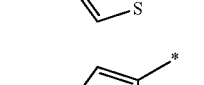 C$_8$H$_{17}$- |
| Compound 118 | S | S | 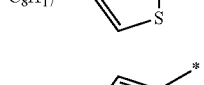 C$_9$H$_{19}$- | 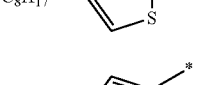 C$_9$H$_{19}$- | 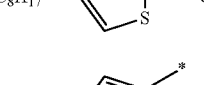 C$_9$H$_{19}$- | 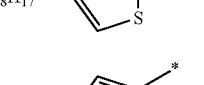 C$_9$H$_{19}$- |
| Compound 119 | S | S | 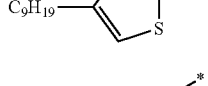 C$_{10}$H$_{21}$- | 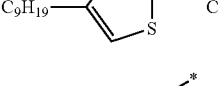 C$_{10}$H$_{21}$- | 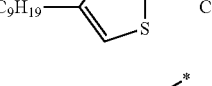 C$_{10}$H$_{21}$- | 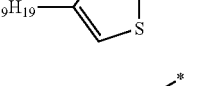 C$_{10}$H$_{21}$- |

TABLE 5-continued

| | $X^{a1}$ | $X^{a2}$ | $R^{a11}$ | $R^{a12}$ | $R^{a21}$ | $R^{a22}$ |
|---|---|---|---|---|---|---|
| Compound 120 | S | S | 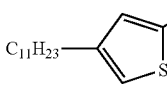 | 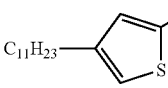 | 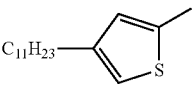 | 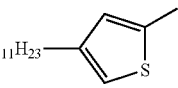 |
| Compound 121 | S | S | 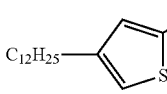 | 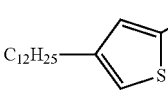 | 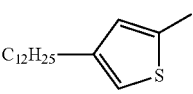 | 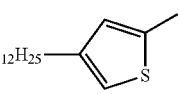 |
| Compound 122 | S | S | 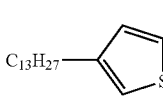 | 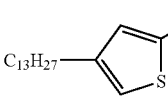 | 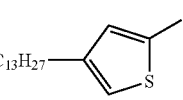 | 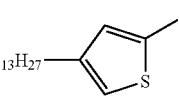 |
| Compound 123 | S | S | 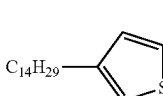 | 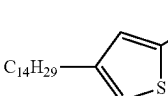 | 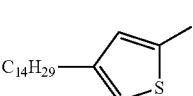 | 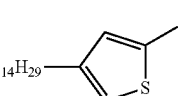 |
| Compound 124 | S | S | 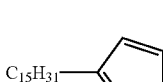 | 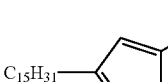 |  | 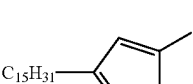 |
| Compound 125 | S | S |  | 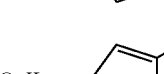 |  |  |
| Compound 126 | S | S |  | 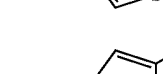 |  | 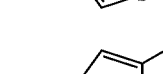 |
| Compound 127 | S | S |  | 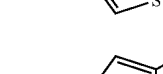 |  | 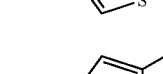 |

TABLE 6

| | $X^{a1}$ | $X^{a2}$ | $R^{a11}$ | $R^{a12}$ | $R^{a21}$ | $R^{a22}$ |
|---|---|---|---|---|---|---|
| Compound 128 | S | S | H | $C_5H_{11}$—* | H | $C_5H_{11}$—* |
| Compound 129 | S | S | H | $C_6H_{13}$—* | H | $C_6H_{13}$—* |
| Compound 130 | S | S | H | $C_7H_{15}$—* | H | $C_7H_{15}$—* |
| Compound 131 | S | S | H | $C_8H_{17}$—* | H | $C_8H_{17}$—* |
| Compound 132 | S | S | H | $C_9H_{19}$—* | H | $C_9H_{19}$—* |
| Compound 133 | S | S | H | $C_{10}H_{21}$—* | H | $C_{10}H_{21}$—* |
| Compound 134 | S | S | H | $C_{11}H_{23}$—* | H | $C_{11}H_{23}$—* |
| Compound 135 | S | S | H | $C_{12}H_{25}$—* | H | $C_{12}H_{25}$—* |
| Compound 136 | S | S | H | $C_{13}H_{27}$—* | H | $C_{13}H_{27}$—* |
| Compound 137 | S | S | H | $C_{14}H_{29}$—* | H | $C_{14}H_{29}$—* |
| Compound 138 | S | S | H | $C_{15}H_{31}$—* | H | $C_{15}H_{31}$—* |
| Compound 139 | S | S | H | $C_{16}H_{33}$—* | H | $C_{16}H_{33}$—* |
| Compound 140 | S | S | H | $C_{17}H_{35}$—* | H | $C_{17}H_{35}$—* |
| Compound 141 | S | S | H | $C_{18}H_{37}$—* | H | $C_{18}H_{37}$—* |
| Compound 142 | S | S | H | p-$C_5H_{11}$—Ph—* | H | p-$C_5H_{11}$—Ph—* |
| Compound 143 | S | S | H | p-$C_6H_{13}$—Ph—* | H | p-$C_6H_{13}$—Ph—* |
| Compound 144 | S | S | H | p-$C_7H_{15}$—Ph—* | H | p-$C_7H_{15}$—Ph—* |
| Compound 145 | S | S | H | p-$C_8H_{17}$—Ph—* | H | p-$C_8H_{17}$—Ph—* |
| Compound 146 | S | S | H | p-$C_9H_{19}$—Ph—* | H | p-$C_9H_{19}$—Ph—* |
| Compound 147 | S | S | H | p-$C_{10}H_{21}$—Ph—* | H | p-$C_{10}H_{21}$—Ph—* |
| Compound 148 | S | S | H | p-$C_{11}H_{23}$—Ph—* | H | p-$C_{11}H_{23}$—Ph—* |
| Compound 149 | S | S | H | p-$C_{12}H_{25}$—Ph—* | H | p-$C_{12}H_{25}$—Ph—* |
| Compound 150 | S | S | H | p-$C_{13}H_{27}$—Ph—* | H | p-$C_{13}H_{27}$—Ph—* |
| Compound 151 | S | S | H | p-$C_{14}H_{29}$—Ph—* | H | p-$C_{14}H_{29}$—Ph—* |
| Compound 152 | S | S | H | p-$C_{15}H_{31}$—Ph—* | H | p-$C_{15}H_{31}$—Ph—* |
| Compound 153 | S | S | H | p-$C_{16}H_{33}$—Ph—* | H | p-$C_{16}H_{33}$—Ph—* |
| Compound 154 | S | S | H | p-$C_{17}H_{35}$—Ph—* | H | p-$C_{17}H_{35}$—Ph—* |
| Compound 155 | S | S | H | p-$C_{18}H_{37}$—Ph—* | H | p-$C_{18}H_{37}$—Ph—* |

TABLE 6-continued

| | $X^{a1}$ | $X^{a2}$ | $R^{a11}$ | $R^{a12}$ | $R^{a21}$ | $R^{a22}$ |
|---|---|---|---|---|---|---|
| Compound 156 | S | S | H | 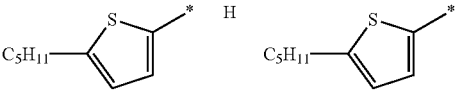 C$_5$H$_{11}$-thiophene-* | H | 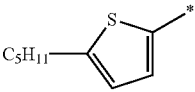 C$_5$H$_{11}$-thiophene-* |
| Compound 157 | S | S | H | 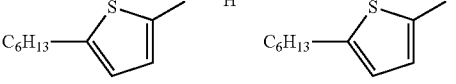 C$_6$H$_{13}$-thiophene-* | H | 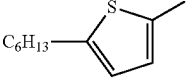 C$_6$H$_{13}$-thiophene-* |
| Compound 158 | S | S | H | 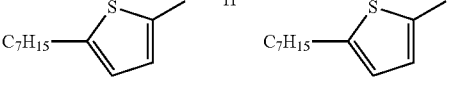 C$_7$H$_{15}$-thiophene-* | H | 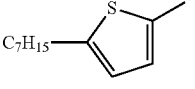 C$_7$H$_{15}$-thiophene-* |
| Compound 159 | S | S | H | 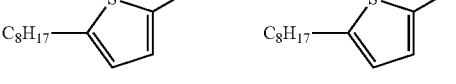 C$_8$H$_{17}$-thiophene-* | H | 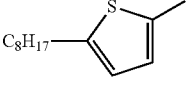 C$_8$H$_{17}$-thiophene-* |
| Compound 160 | S | S | H | 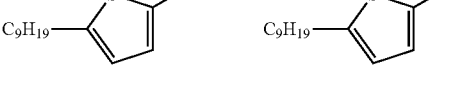 C$_9$H$_{19}$-thiophene-* | H | 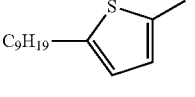 C$_9$H$_{19}$-thiophene-* |
| Compound 161 | S | S | H | 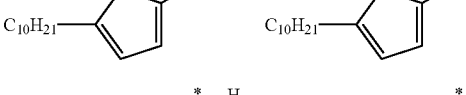 C$_{10}$H$_{21}$-thiophene-* | H | 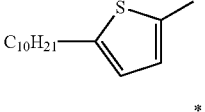 C$_{10}$H$_{21}$-thiophene-* |
| Compound 162 | S | S | H |  C$_{11}$H$_{23}$-thiophene-* | H | 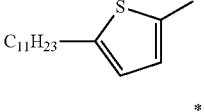 C$_{11}$H$_{23}$-thiophene-* |
| Compound 163 | S | S | H | 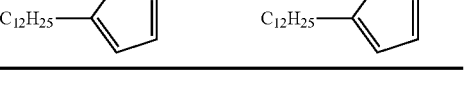 C$_{12}$H$_{25}$-thiophene-* | H | 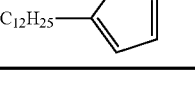 C$_{12}$H$_{25}$-thiophene-* |

TABLE 7

| | $X^{a1}$ | $X^{a2}$ | $R^{a11}$ | $R^{a12}$ | $R^{a21}$ | $R^{a22}$ |
|---|---|---|---|---|---|---|
| Compound 164 | S | S | H |  C$_{13}$H$_{27}$-thiophene-* | H | 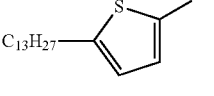 C$_{13}$H$_{27}$-thiophene-* |
| Compound 165 | S | S | H |  C$_{14}$H$_{29}$-thiophene-* | H | 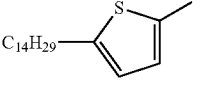 C$_{14}$H$_{29}$-thiophene-* |
| Compound 166 | S | S | H |  C$_{15}$H$_{31}$-thiophene-* | H | 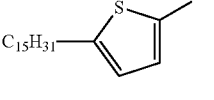 C$_{15}$H$_{31}$-thiophene-* |
| Compound 167 | S | S | H |  C$_{16}$H$_{33}$-thiophene-* | H | 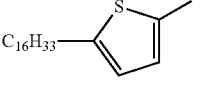 C$_{16}$H$_{33}$-thiophene-* |
| Compound 168 | S | S | H |  C$_{17}$H$_{35}$-thiophene-* | H | 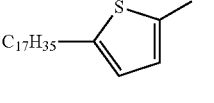 C$_{17}$H$_{35}$-thiophene-* |

TABLE 7-continued

| | $X^{a1}$ | $X^{a2}$ | $R^{a11}$ | $R^{a12}$ | $R^{a21}$ | $R^{a22}$ |
|---|---|---|---|---|---|---|
| Compound 169 | S | S | H | 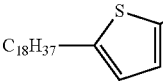 C₁₈H₃₇ thiophene-* | H | 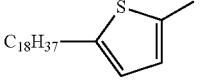 C₁₈H₃₇ thiophene-* |
| Compound 170 | S | S | H | H | $C_5H_{11}$—* | H |
| Compound 171 | S | S | H | H | $C_6H_{13}$—* | H |
| Compound 172 | S | S | H | H | $C_7H_{15}$—* | H |
| Compound 173 | S | S | H | H | $C_8H_{17}$—* | H |
| Compound 174 | S | S | H | H | $C_9H_{19}$—* | H |
| Compound 175 | S | S | H | H | $C_{10}H_{21}$—* | H |
| Compound 176 | S | S | H | H | $C_{11}H_{23}$—* | H |
| Compound 177 | S | S | H | H | $C_{12}H_{25}$—* | H |
| Compound 178 | S | S | H | H | $C_{13}H_{27}$—* | H |
| Compound 179 | S | S | H | H | $C_{14}H_{29}$—* | H |
| Compound 180 | S | S | H | H | $C_{15}H_{31}$—* | H |
| Compound 181 | S | S | H | H | $C_{16}H_{33}$—* | H |
| Compound 182 | S | S | H | H | $C_{17}H_{35}$—* | H |
| Compound 183 | S | S | H | H | $C_{18}H_{37}$—* | H |
| Compound 184 | S | S | Ph | H | $C_5H_{11}$—* | H |
| Compound 185 | S | S | Ph | H | $C_6H_{13}$—* | H |
| Compound 186 | S | S | Ph | H | $C_7H_{15}$—* | H |
| Compound 187 | S | S | Ph | H | $C_8H_{17}$—* | H |
| Compound 188 | S | S | Ph | H | $C_9H_{19}$—* | H |
| Compound 189 | S | S | Ph | H | $C_{10}H_{21}$—* | H |
| Compound 190 | S | S | Ph | H | $C_{11}H_{23}$—* | H |
| Compound 191 | S | S | Ph | H | $C_{12}H_{25}$—* | H |
| Compound 192 | S | S | Ph | H | $C_{13}H_{27}$—* | H |
| Compound 193 | S | S | Ph | H | $C_{14}H_{29}$—* | H |
| Compound 194 | S | S | Ph | H | $C_{15}H_{31}$—* | H |
| Compound 195 | S | S | Ph | H | $C_{16}H_{33}$—* | H |
| Compound 196 | S | S | Ph | H | $C_{17}H_{35}$—* | H |
| Compound 197 | S | S | Ph | H | $C_{18}H_{37}$—* | H |
| Compound 198 | S | S | 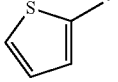 thiophene-* | H | $C_5H_{11}$—* | H |
| Compound 199 | S | S | 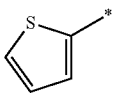 thiophene-* | H | $C_6H_{13}$—* | H |

TABLE 8

| | $X^{a1}$ | $X^{a2}$ | $R^{a11}$ | $R^{a12}$ | $R^{a21}$ | $R^{a22}$ |
|---|---|---|---|---|---|---|
| Compound 200 | S | S |  thiophene-* | H | $C_7H_{15}$—* | H |
| Compound 201 | S | S |  thiophene-* | H | $C_8H_{17}$—* | H |
| Compound 202 | S | S |  thiophene-* | H | $C_9H_{19}$—* | H |
| Compound 203 | S | S |  thiophene-* | H | $C_{10}H_{21}$—* | H |
| Compound 204 | S | S |  thiophene-* | H | $C_{11}H_{23}$—* | H |

TABLE 8-continued

| | $X^{a1}$ | $X^{a2}$ | $R^{a11}$ | $R^{a12}$ | $R^{a21}$ | $R^{a22}$ |
|---|---|---|---|---|---|---|
| Compound 205 | S | S | 2-thienyl—* | H | $C_{12}H_{25}$—* | H |
| Compound 206 | S | S | 2-thienyl—* | H | $C_{13}H_{27}$—* | H |
| Compound 207 | S | S | 2-thienyl—* | H | $C_{14}H_{29}$—* | H |
| Compound 208 | S | S | 2-thienyl—* | H | $C_{15}H_{31}$—* | H |
| Compound 209 | S | S | 2-thienyl—* | H | $C_{16}H_{33}$—* | H |
| Compound 210 | S | S | 2-thienyl—* | H | $C_{17}H_{35}$—* | H |
| Compound 211 | S | S | 2-thienyl—* | H | $C_{18}H_{37}$—* | H |
| Compound 212 | S | S | H | H | H | $C_5H_{11}$—* |
| Compound 213 | S | S | H | H | H | $C_6H_{13}$—* |
| Compound 214 | S | S | H | H | H | $C_7H_{15}$—* |
| Compound 215 | S | S | H | H | H | $C_8H_{17}$—* |
| Compound 216 | S | S | H | H | H | $C_9H_{19}$—* |
| Compound 217 | S | S | H | H | H | $C_{10}H_{21}$—* |
| Compound 218 | S | S | H | H | H | $C_{11}H_{23}$—* |
| Compound 219 | S | S | H | H | H | $C_{12}H_{25}$—* |
| Compound 220 | S | S | H | H | H | $C_{13}H_{27}$—* |
| Compound 221 | S | S | H | H | H | $C_{14}H_{29}$—* |
| Compound 222 | S | S | H | H | H | $C_{15}H_{31}$—* |
| Compound 223 | S | S | H | H | H | $C_{16}H_{33}$—* |
| Compound 224 | S | S | H | H | H | $C_{17}H_{35}$—* |
| Compound 225 | S | S | H | H | H | $C_{18}H_{37}$—* |
| Compound 226 | S | S | H | H | p-$C_5H_{11}$—Ph—* | H |
| Compound 227 | S | S | H | H | p-$C_6H_{13}$—Ph—* | H |
| Compound 228 | S | S | H | H | p-$C_7H_{15}$—Ph—* | H |
| Compound 229 | S | S | H | H | p-$C_8H_{17}$—Ph—* | H |
| Compound 230 | S | S | H | H | p-$C_9H_{19}$—Ph—* | H |

Note: For Compounds 205–211, $R^{a11}$ is a 2-thienyl group (thiophene attached at position 2).

TABLE 9

| | $X^{a1}$ | $X^{a2}$ | $R^{a11}$ | $R^{a12}$ | $R^{a21}$ | $R^{a22}$ |
|---|---|---|---|---|---|---|
| Compound 231 | S | S | H | H | p-$C_{10}H_{21}$—Ph—* | H |
| Compound 232 | S | S | H | H | p-$C_{11}H_{23}$—Ph—* | H |
| Compound 233 | S | S | H | H | p-$C_{12}H_{25}$—Ph—* | H |
| Compound 234 | S | S | H | H | p-$C_{13}H_{27}$—Ph—* | H |
| Compound 235 | S | S | H | H | p-$C_{14}H_{29}$—Ph—* | H |
| Compound 236 | S | S | H | H | p-$C_{15}H_{31}$—Ph—* | H |
| Compound 237 | S | S | H | H | p-$C_{16}H_{33}$—Ph—* | H |
| Compound 238 | S | S | H | H | p-$C_{17}H_{35}$—Ph—* | H |
| Compound 239 | S | S | H | H | p-$C_{18}H_{37}$—Ph—* | H |
| Compound 240 | S | S | Ph | H | p-$C_5H_{11}$—Ph—* | H |
| Compound 241 | S | S | Ph | H | p-$C_6H_{13}$—Ph—* | H |
| Compound 242 | S | S | Ph | H | p-$C_7H_{15}$—Ph—* | H |
| Compound 243 | S | S | Ph | H | p-$C_8H_{17}$—Ph—* | H |
| Compound 244 | S | S | Ph | H | p-$C_9H_{19}$—Ph—* | H |
| Compound 245 | S | S | Ph | H | p-$C_{10}H_{21}$—Ph—* | H |
| Compound 246 | S | S | Ph | H | p-$C_{11}H_{23}$—Ph—* | H |
| Compound 247 | S | S | Ph | H | p-$C_{12}H_{25}$—Ph—* | H |
| Compound 248 | S | S | Ph | H | p-$C_{13}H_{27}$—Ph—* | H |
| Compound 249 | S | S | Ph | H | p-$C_{14}H_{29}$—Ph—* | H |
| Compound 250 | S | S | Ph | H | p-$C_{15}H_{31}$—Ph—* | H |
| Compound 251 | S | S | Ph | H | p-$C_{16}H_{33}$—Ph—* | H |
| Compound 252 | S | S | Ph | H | p-$C_{17}H_{35}$—Ph—* | H |
| Compound 253 | S | S | Ph | H | p-$C_{18}H_{37}$—Ph—* | H |

TABLE 9-continued

| | $X^{a1}$ | $X^{a2}$ | $R^{a11}$ | $R^{a12}$ | $R^{a21}$ | $R^{a22}$ |
|---|---|---|---|---|---|---|
| Compound 254 | S | S |  | H | p-$C_5H_{11}$—Ph—* | H |
| Compound 255 | S | S |  | H | p-$C_6H_{13}$—Ph—* | H |
| Compound 256 | S | S |  | H | p-$C_7H_{15}$—Ph—* | H |
| Compound 257 | S | S |  | H | p-$C_8H_{17}$—Ph—* | H |
| Compound 258 | S | S |  | H | p-$C_9H_{19}$—Ph—* | H |
| Compound 259 | S | S |  | H | p-$C_{10}H_{21}$—Ph—* | H |
| Compound 260 | S | S |  | H | p-$C_{11}H_{23}$—Ph—* | H |
| Compound 261 | S | S |  | H | p-$C_{12}H_{25}$—Ph—* | H |
| Compound 262 | S | S |  | H | p-$C_{13}H_{27}$—Ph—* | H |
| Compound 263 | S | S |  | H | p-$C_{14}H_{29}$—Ph—* | H |

TABLE 10

| | $X^{a1}$ | $X^{a2}$ | $R^{a11}$ | $R^{a12}$ | $R^{a21}$ | $R^{a22}$ |
|---|---|---|---|---|---|---|
| Compound 264 | S | S |  | H | p-$C_{15}H_{31}$—Ph—* | H |
| Compound 265 | S | S |  | H | p-$C_{16}H_{33}$—Ph—* | H |
| Compound 266 | S | S |  | H | p-$C_{17}H_{35}$—Ph—* | H |
| Compound 267 | S | S |  | H | p-$C_{18}H_{37}$—Ph—* | H |
| Compound 268 | S | S | H | H | H | p-$C_5H_{11}$—Ph—* |
| Compound 269 | S | S | H | H | H | p-$C_6H_{13}$—Ph—* |
| Compound 270 | S | S | H | H | H | p-$C_7H_{15}$—Ph—* |
| Compound 271 | S | S | H | H | H | p-$C_8H_{17}$—Ph—* |
| Compound 272 | S | S | H | H | H | p-$C_9H_{19}$—Ph—* |
| Compound 273 | S | S | H | H | H | p-$C_{10}H_{21}$—Ph—* |
| Compound 274 | S | S | H | H | H | p-$C_{11}H_{23}$—Ph—* |
| Compound 275 | S | S | H | H | H | p-$C_{12}H_{25}$—Ph—* |
| Compound 276 | S | S | H | H | H | p-$C_{13}H_{27}$—Ph—* |
| Compound 277 | S | S | H | H | H | p-$C_{14}H_{29}$—Ph—* |
| Compound 278 | S | S | H | H | H | p-$C_{15}H_{31}$—Ph—* |
| Compound 279 | S | S | H | H | H | p-$C_{16}H_{33}$—Ph—* |
| Compound 280 | S | S | H | H | H | p-$C_{17}H_{35}$—Ph—* |
| Compound 281 | S | S | H | H | H | p-$C_{18}H_{37}$—Ph—* |
| Compound 282 | S | S | H | H | 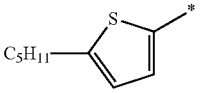 | H |

TABLE 10-continued

| | $X^{a1}$ | $X^{a2}$ | $R^{a11}$ | $R^{a12}$ | $R^{a21}$ | $R^{a22}$ |
|---|---|---|---|---|---|---|
| Compound 283 | S | S | H | H | 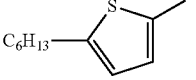 | H |
| Compound 284 | S | S | H | H | 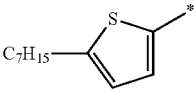 | H |
| Compound 285 | S | S | H | H | 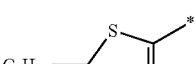 | H |
| Compound 286 | S | S | H | H | 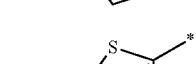 | H |
| Compound 287 | S | S | H | H | 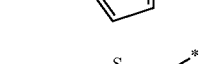 | H |
| Compound 288 | S | S | H | H | 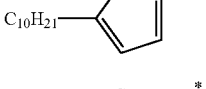 | H |
| Compound 289 | S | S | H | H | 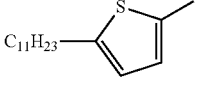 | H |
| Compound 290 | S | S | H | H | 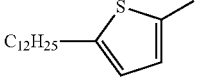 | H |

TABLE 11

| | $X^{a1}$ | $X^{a2}$ | $R^{a11}$ | $R^{a12}$ | $R^{a21}$ | $R^{a22}$ |
|---|---|---|---|---|---|---|
| Compound 291 | S | S | H | H | 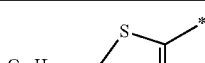 | H |
| Compound 292 | S | S | H | H | 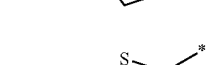 | H |
| Compound 293 | S | S | H | H | 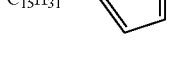 | H |
| Compound 294 | S | S | H | H | 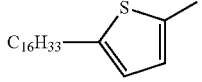 | H |
| Compound 295 | S | S | Ph | H | 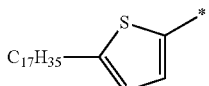 | H |
| Compound 296 | S | S | Ph | H | 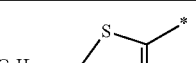 | H |
| Compound 297 | S | S | Ph | H | 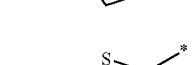 | H |
| Compound 298 | S | S | Ph | H | 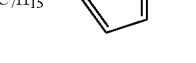 | H |
| Compound 299 | S | S | Ph | H | 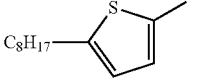 | H |
| Compound 300 | S | S | Ph | H | 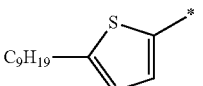 | H |

TABLE 11-continued

| | $X^{a1}$ | $X^{a2}$ | $R^{a11}$ | $R^{a12}$ | $R^{a21}$ | $R^{a22}$ |
|---|---|---|---|---|---|---|
| Compound 301 | S | S | Ph | H | 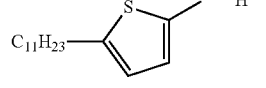 $C_{11}H_{23}$ | H |
| Compound 302 | S | S | Ph | H | 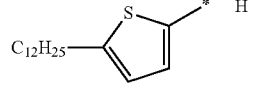 $C_{12}H_{25}$ | H |
| Compound 303 | S | S | Ph | H | 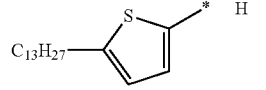 $C_{13}H_{27}$ | H |
| Compound 304 | S | S | Ph | H | 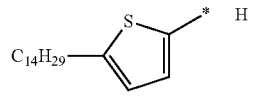 $C_{14}H_{29}$ | H |
| Compound 305 | S | S | Ph | H | 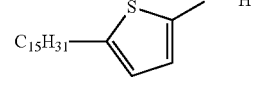 $C_{15}H_{31}$ | H |
| Compound 306 | S | S | Ph | H | 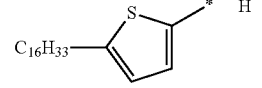 $C_{16}H_{33}$ | H |
| Compound 307 | S | S | Ph | H | 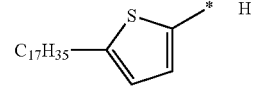 $C_{17}H_{35}$ | H |
| Compound 308 | S | S | 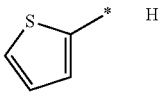 | H | 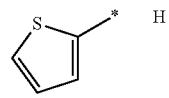 $C_5H_{11}$ | H |

TABLE 12

| | $X^{a1}$ | $X^{a2}$ | $R^{a11}$ | $R^{a12}$ | $R^{a21}$ | $R^{a22}$ |
|---|---|---|---|---|---|---|
| Compound 309 | S | S | 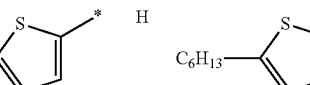 | H | 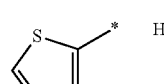 $C_6H_{13}$ | H |
| Compound 310 | S | S | 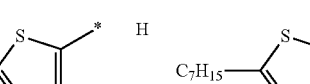 | H | 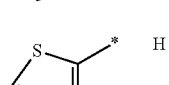 $C_7H_{15}$ | H |
| Compound 311 | S | S | 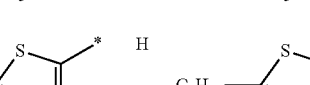 | H | 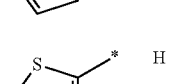 $C_8H_{17}$ | H |
| Compound 312 | S | S | 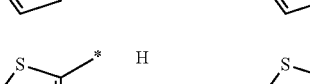 | H | 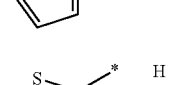 $C_9H_{19}$ | H |
| Compound 313 | S | S | 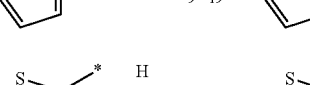 | H | 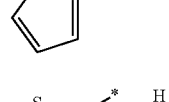 $C_{10}H_{21}$ | H |
| Compound 314 | S | S | 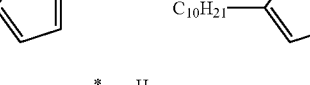 | H | 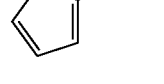 $C_{11}H_{23}$ | H |
| Compound 315 | S | S |  | H | 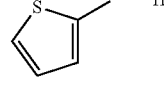 $C_{12}H_{25}$ | H |
| Compound 316 | S | S | 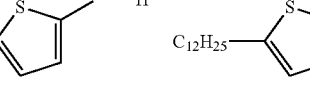 | H | 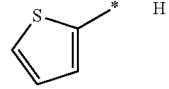 $C_{13}H_{27}$ | H |
| Compound 317 | S | S | 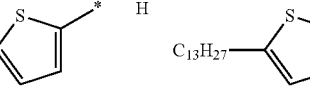 | H |  $C_{14}H_{29}$ | H |

TABLE 12-continued

| | $X^{a1}$ | $X^{a2}$ | $R^{a11}$ | $R^{a12}$ | $R^{a21}$ | $R^{a22}$ |
|---|---|---|---|---|---|---|
| Compound 318 | S | S | 2-thienyl | H | 5-$C_{15}H_{31}$-2-thienyl | H |
| Compound 319 | S | S | 2-thienyl | H | 5-$C_{16}H_{33}$-2-thienyl | H |
| Compound 320 | S | S | 2-thienyl | H | 5-$C_{17}H_{35}$-2-thienyl | H |
| Compound 321 | S | S | H | H | H | 5-$C_5H_{11}$-2-thienyl |
| Compound 322 | S | S | H | H | H | 5-$C_6H_{13}$-2-thienyl |
| Compound 323 | S | S | H | H | H | 5-$C_7H_{15}$-2-thienyl |
| Compound 324 | S | S | H | H | H | 5-$C_8H_{17}$-2-thienyl |
| Compound 325 | S | S | H | H | H | 5-$C_9H_{19}$-2-thienyl |
| Compound 326 | S | S | H | H | H | 5-$C_{10}H_{21}$-2-thienyl |

TABLE 13

| | $X^{a1}$ | $X^{a2}$ | $R^{a11}$ | $R^{a12}$ | $R^{a21}$ | $R^{a22}$ |
|---|---|---|---|---|---|---|
| Compound 327 | S | S | H | H | H | 5-$C_{11}H_{23}$-2-thienyl |
| Compound 328 | S | S | H | H | H | 5-$C_{12}H_{25}$-2-thienyl |
| Compound 329 | S | S | H | H | H | 5-$C_{13}H_{27}$-2-thienyl |
| Compound 330 | S | S | H | H | H | 5-$C_{14}H_{29}$-2-thienyl |

TABLE 13-continued
| | $X^{a1}$ | $X^{a2}$ | $R^{a11}$ | $R^{a12}$ | $R^{a21}$ | $R^{a22}$ |
|---|---|---|---|---|---|---|
| Compound 331 | S | S | H | H | H | 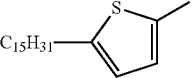 |
| Compound 332 | S | S | H | H | H | 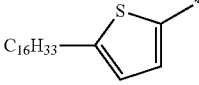 |
| Compound 333 | S | S | H | H | H | 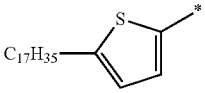 |
| Compound 334 | S | S | H | H | 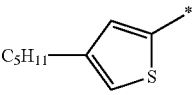 | H |
| Compound 335 | S | S | H | H | 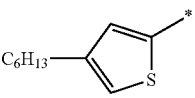 | H |
| Compound 336 | S | S | H | H | 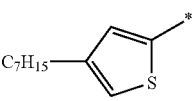 | H |
| Compound 337 | S | S | H | H | 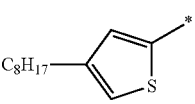 | H |
| Compound 338 | S | S | H | H | 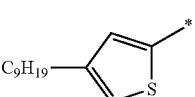 | H |
| Compound 339 | S | S | H | H | 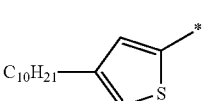 | H |
| Compound 340 | S | S | H | H |  | H |
| Compound 341 | S | S | H | H |  | H |
| Compound 342 | S | S | H | H |  | H |
| Compound 343 | S | S | H | H |  | H |
| Compound 344 | S | S | H | H | 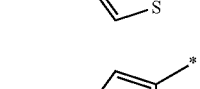 | H |

TABLE 14
| | $X^{a1}$ | $X^{a2}$ | $R^{a11}$ | $R^{a12}$ | $R^{a21}$ | $R^{a22}$ |
|---|---|---|---|---|---|---|
| Compound 345 | S | S | H | H | 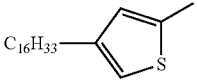 $C_{16}H_{33}$- | H |
| Compound 346 | S | S | H | H | 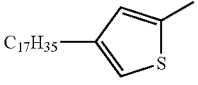 $C_{17}H_{35}$- | H |
| Compound 347 | S | S | H | H | 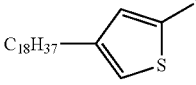 $C_{18}H_{37}$- | H |
| Compound 348 | S | S | Ph | H | 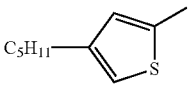 $C_{5}H_{11}$- | H |
| Compound 349 | S | S | Ph | H | 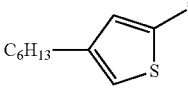 $C_{6}H_{13}$- | H |
| Compound 350 | S | S | Ph | H | 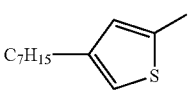 $C_{7}H_{15}$- | H |
| Compound 351 | S | S | Ph | H | 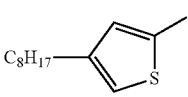 $C_{8}H_{17}$- | H |
| Compound 352 | S | S | Ph | H | 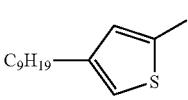 $C_{9}H_{19}$- | H |
| Compound 353 | S | S | Ph | H | 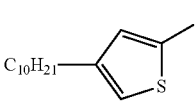 $C_{10}H_{21}$- | H |
| Compound 354 | S | S | Ph | H | 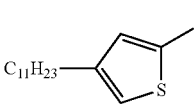 $C_{11}H_{23}$- | H |
| Compound 355 | S | S | Ph | H | 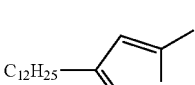 $C_{12}H_{25}$- | H |
| Compound 356 | S | S | Ph | H | 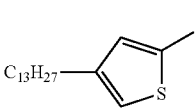 $C_{13}H_{27}$- | H |
| Compound 357 | S | S | Ph | H | 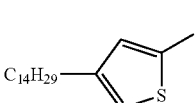 $C_{14}H_{29}$- | H |
| Compound 358 | S | S | Ph | H | 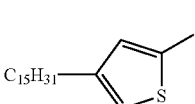 $C_{15}H_{31}$- | H |

TABLE 14-continued
| | $X^{a1}$ | $X^{a2}$ | $R^{a11}$ | $R^{a12}$ | $R^{a21}$ | $R^{a22}$ |
|---|---|---|---|---|---|---|
| Compound 359 | S | S | Ph | H | 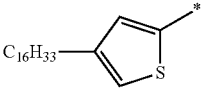 | H |
| Compound 360 | S | S | Ph | H | 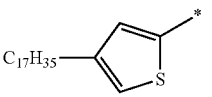 | H |
| Compound 361 | S | S | Ph | H | 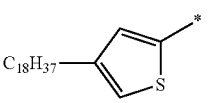 | H |
| Compound 362 | S | S | 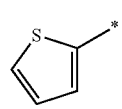 | H | 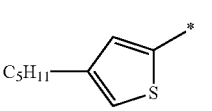 | H |
TABLE 15
| | $X^{a1}$ | $X^{a2}$ | $R^{a11}$ | $R^{a12}$ | $R^{a21}$ | $R^{a22}$ |
|---|---|---|---|---|---|---|
| Compound 363 | S | S | 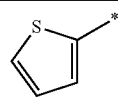 | H | 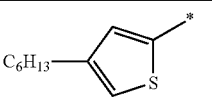 | H |
| Compound 364 | S | S | 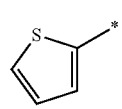 | H | 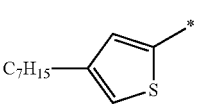 | H |
| Compound 365 | S | S | 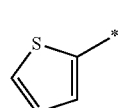 | H | 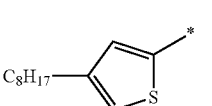 | H |
| Compound 366 | S | S | 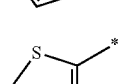 | H |  | H |
| Compound 367 | S | S | 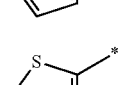 | H | 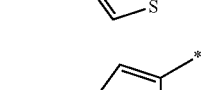 | H |
| Compound 368 | S | S | 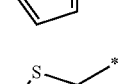 | H | 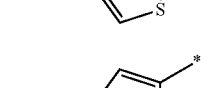 | H |
| Compound 369 | S | S | 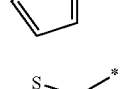 | H |  | H |
| Compound 370 | S | S | 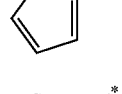 | H | 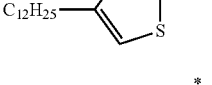 | H |
| Compound 371 | S | S | 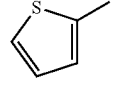 | H | 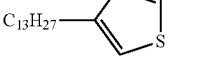 | H |

TABLE 15-continued

| | $X^{a1}$ | $X^{a2}$ | $R^{a11}$ | $R^{a12}$ | $R^{a21}$ | $R^{a22}$ |
|---|---|---|---|---|---|---|
| Compound 372 | S | S |  | H | 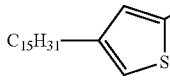 | H |
| Compound 373 | S | S |  | H | 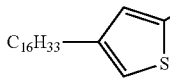 | H |
| Compound 374 | S | S |  | H | 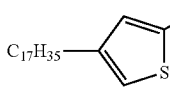 | H |
| Compound 375 | S | S |  | H | 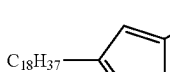 | H |
| Compound 376 | S | S | $C_{10}H_{21}$—* | H | p-$C_5H_{11}$—Ph—* | H |
| Compound 377 | S | S | $C_{10}H_{21}$—* | H | p-$C_6H_{13}$—Ph—* | H |
| Compound 378 | S | S | $C_{10}H_{21}$—* | H | p-$C_7H_{15}$—Ph—* | H |
| Compound 379 | S | S | $C_{10}H_{21}$—* | H | p-$C_8H_{17}$—Ph—* | H |
| Compound 380 | S | S | $C_{10}H_{21}$—* | H | p-$C_9H_{19}$—Ph—* | H |
| Compound 381 | S | S | $C_{10}H_{21}$—* | H | p-$C_{10}H_{21}$—Ph—* | H |
| Compound 382 | S | S | $C_{10}H_{21}$—* | H | p-$C_{11}H_{23}$—Ph—* | H |
| Compound 383 | S | S | $C_{10}H_{21}$—* | H | p-$C_{12}H_{25}$—Ph—* | H |
| Compound 384 | S | S | $C_{10}H_{21}$—* | H | p-$C_{13}H_{27}$—Ph—* | H |
| Compound 385 | S | S | $C_{10}H_{21}$—* | H | p-$C_{14}H_{29}$—Ph—* | H |
| Compound 386 | S | S | $C_{10}H_{21}$—* | H | p-$C_{15}H_{31}$—Ph—* | H |
| Compound 387 | S | S | $C_{10}H_{21}$—* | H | p-$C_{16}H_{33}$—Ph—* | H |
| Compound 388 | S | S | $C_{10}H_{21}$—* | H | p-$C_{17}H_{35}$—Ph—* | H |
| Compound 389 | S | S | $C_{10}H_{21}$—* | H | p-$C_{18}H_{37}$—Ph—* | H |

TABLE 16

| | $X^{a1}$ | $X^{a2}$ | $R^{a11}$ | $R^{a12}$ | $R^{a21}$ | $R^{a22}$ |
|---|---|---|---|---|---|---|
| Compound 390 | S | S | $C_{12}H_{25}$—* | H | 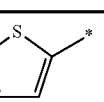 | H |
| Compound 391 | S | S | $C_{12}H_{25}$—* | H | 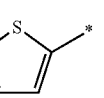 | H |
| Compound 392 | S | S | $C_{12}H_{25}$—* | H | 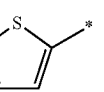 | H |
| Compound 393 | S | S | $C_{12}H_{25}$—* | H | 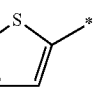 | H |
| Compound 394 | S | S | $C_{12}H_{25}$—* | H | 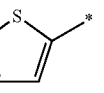 | H |
| Compound 395 | S | S | $C_{12}H_{25}$—* | H | 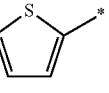 | H |
| Compound 396 | S | S | $C_{12}H_{25}$—* | H | 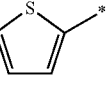 | H |

TABLE 16-continued

| | $X^{a1}$ | $X^{a2}$ | $R^{a11}$ | $R^{a12}$ | $R^{a21}$ | $R^{a22}$ |
|---|---|---|---|---|---|---|
| Compound 397 | S | S | $C_{12}H_{25}$—* | H | 5-$C_{12}H_{25}$-thiophen-2-yl—* | H |
| Compound 398 | S | S | $C_{12}H_{25}$—* | H | 5-$C_{13}H_{27}$-thiophen-2-yl—* | H |
| Compound 399 | S | S | $C_{12}H_{25}$—* | H | 5-$C_{14}H_{29}$-thiophen-2-yl—* | H |
| Compound 400 | S | S | $C_{12}H_{25}$—* | H | 5-$C_{15}H_{31}$-thiophen-2-yl—* | H |
| Compound 401 | S | S | $C_{12}H_{25}$—* | H | 5-$C_{16}H_{33}$-thiophen-2-yl—* | H |
| Compound 402 | S | S | $C_{12}H_{25}$—* | H | 5-$C_{17}H_{35}$-thiophen-2-yl—* | H |
| Compound 403 | S | S | $C_{12}H_{25}$—* | H | 5-$C_{18}H_{37}$-thiophen-2-yl—* | H |
| Compound 404 | S | S | $C_5H_{11}$—* | H | H | $C_{12}H_{25}$—* |
| Compound 405 | S | S | $C_6H_{13}$—* | H | H | $C_{12}H_{25}$—* |
| Compound 406 | S | S | $C_7H_{15}$—* | H | H | $C_{12}H_{25}$—* |
| Compound 407 | S | S | $C_8H_{17}$—* | H | H | $C_{12}H_{25}$—* |
| Compound 408 | S | S | $C_9H_{19}$—* | H | H | $C_{12}H_{25}$—* |
| Compound 409 | S | S | $C_{10}H_{21}$—* | H | H | $C_{12}H_{25}$—* |
| Compound 410 | S | S | $C_{11}H_{23}$—* | H | H | $C_{12}H_{25}$—* |
| Compound 411 | S | S | $C_{12}H_{25}$—* | H | H | $C_{12}H_{25}$—* |
| Compound 412 | S | S | $C_{13}H_{27}$—* | H | H | $C_{12}H_{25}$—* |
| Compound 413 | S | S | $C_{14}H_{29}$—* | H | H | $C_{12}H_{25}$—* |
| Compound 414 | S | S | $C_{15}H_{31}$—* | H | H | $C_{12}H_{25}$—* |
| Compound 415 | S | S | $C_{16}H_{33}$—* | H | H | $C_{12}H_{25}$—* |
| Compound 416 | S | S | $C_{17}H_{35}$—* | H | H | $C_{12}H_{25}$—* |
| Compound 417 | S | S | $C_{18}H_{37}$—* | H | H | $C_{12}H_{25}$—* |

TABLE 17

| | $X^{a1}$ | $X^{a2}$ | $R^{a11}$ | $R^{a12}$ | $R^{a21}$ | $R^{a22}$ |
|---|---|---|---|---|---|---|
| Compound 418 | S | S | $C_{10}H_{21}$—* | H | H | p-$C_5H_{11}$—Ph—* |
| Compound 419 | S | S | $C_{10}H_{21}$—* | H | H | p-$C_6H_{13}$—Ph—* |
| Compound 420 | S | S | $C_{10}H_{21}$—* | H | H | p-$C_7H_{15}$—Ph—* |
| Compound 421 | S | S | $C_{10}H_{21}$—* | H | H | p-$C_8H_{17}$—Ph—* |
| Compound 422 | S | S | $C_{10}H_{21}$—* | H | H | p-$C_9H_{19}$—Ph—* |
| Compound 423 | S | S | $C_{10}H_{21}$—* | H | H | p-$C_{10}H_{21}$—Ph—* |
| Compound 424 | S | S | $C_{10}H_{21}$—* | H | H | p-$C_{11}H_{23}$—Ph—* |
| Compound 425 | S | S | $C_{10}H_{21}$—* | H | H | p-$C_{12}H_{25}$—Ph—* |
| Compound 426 | S | S | $C_{10}H_{21}$—* | H | H | p-$C_{13}H_{27}$—Ph—* |
| Compound 427 | S | S | $C_{10}H_{21}$—* | H | H | p-$C_{14}H_{29}$—Ph—* |
| Compound 428 | S | S | $C_{10}H_{21}$—* | H | H | p-$C_{15}H_{31}$—Ph—* |
| Compound 429 | S | S | $C_{10}H_{21}$—* | H | H | p-$C_{16}H_{33}$—Ph—* |
| Compound 430 | S | S | $C_{10}H_{21}$—* | H | H | p-$C_{17}H_{35}$—Ph—* |
| Compound 431 | S | S | $C_{10}H_{21}$—* | H | H | p-$C_{18}H_{37}$—Ph—* |
| Compound 432 | S | S | H | $C_{10}H_{21}$—* | H | p-$C_5H_{11}$—Ph—* |
| Compound 433 | S | S | H | $C_{10}H_{21}$—* | H | p-$C_6H_{13}$—Ph—* |
| Compound 434 | S | S | H | $C_{10}H_{21}$—* | H | p-$C_7H_{15}$—Ph—* |
| Compound 435 | S | S | H | $C_{10}H_{21}$—* | H | p-$C_8H_{17}$—Ph—* |
| Compound 436 | S | S | H | $C_{10}H_{21}$—* | H | p-$C_9H_{19}$—Ph—* |
| Compound 437 | S | S | H | $C_{10}H_{21}$—* | H | p-$C_{10}H_{21}$—Ph—* |
| Compound 438 | S | S | H | $C_{10}H_{21}$—* | H | p-$C_{11}H_{23}$—Ph—* |

TABLE 17-continued

| | $X^{a1}$ | $X^{a2}$ | $R^{a11}$ | $R^{a12}$ | $R^{a21}$ | $R^{a22}$ |
|---|---|---|---|---|---|---|
| Compound 439 | S | S | H | $C_{10}H_{21}$—* | H | p-$C_{12}H_{25}$—Ph—* |
| Compound 440 | S | S | H | $C_{10}H_{21}$—* | H | p-$C_{13}H_{27}$—Ph—* |
| Compound 441 | S | S | H | $C_{10}H_{21}$—* | H | p-$C_{14}H_{29}$—Ph—* |
| Compound 442 | S | S | H | $C_{10}H_{21}$—* | H | p-$C_{15}H_{31}$—Ph—* |
| Compound 443 | S | S | H | $C_{10}H_{21}$—* | H | p-$C_{16}H_{33}$—Ph—* |
| Compound 444 | S | S | H | $C_{10}H_{21}$—* | H | p-$C_{17}H_{35}$—Ph—* |
| Compound 445 | S | S | H | $C_{10}H_{21}$—* | H | p-$C_{18}H_{37}$—Ph—* |
| Compound 446 | S | S | 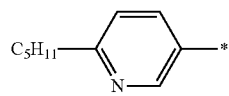 | H | 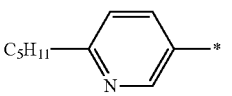 | H |
| Compound 447 | S | S | 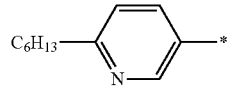 | H | 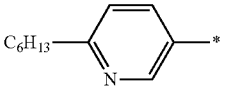 | H |
| Compound 448 | S | S | 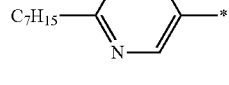 | H | 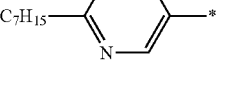 | H |
| Compound 449 | S | S | 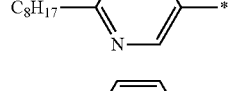 | H | 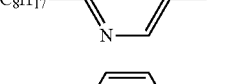 | H |
| Compound 450 | S | S | 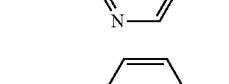 | H | 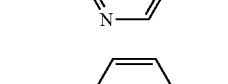 | H |
| Compound 451 | S | S | 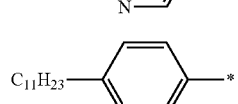 | H | 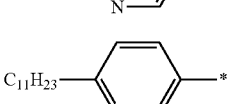 | H |
| Compound 452 | S | S | 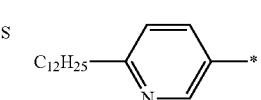 | H | 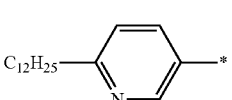 | H |
| Compound 453 | S | S |  | H |  | H |

TABLE 18

| | $X^{a1}$ | $X^{a2}$ | $R^{a11}$ | $R^{a12}$ | $R^{a21}$ | $R^{a22}$ |
|---|---|---|---|---|---|---|
| Compound 454 | S | S | 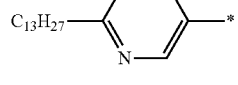 | H | 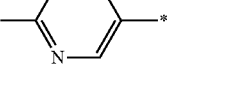 | H |
| Compound 455 | S | S | 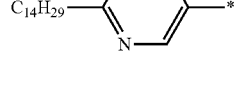 | H | 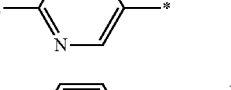 | H |
| Compound 456 | S | S | 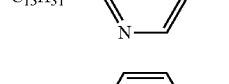 | H | 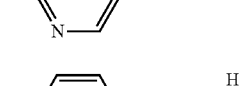 | H |
| Compound 457 | S | S | 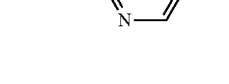 | H | 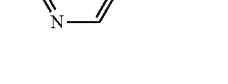 | H |

TABLE 18-continued

| | $X^{a1}$ | $X^{a2}$ | $R^{a11}$ | $R^{a12}$ | $R^{a21}$ | $R^{a22}$ |
|---|---|---|---|---|---|---|
| Compound 458 | S | S | $C_{17}H_{35}$-pyridyl-* | H | $C_{17}H_{35}$-pyridyl-* | H |
| Compound 459 | S | S | $C_{18}H_{37}$-pyridyl-* | H | $C_{18}H_{37}$-pyridyl-* | H |
| Compound 460 | S | S | $C_{7}H_{15}$-CH=CH-* | H | $C_{7}H_{15}$-CH=CH-* | H |
| Compound 461 | S | S | $C_{6}H_{13}$-CH=CH-* | H | $C_{6}H_{13}$-CH=CH-* | H |
| Compound 462 | S | S | $C_{8}H_{17}$-CH=CH-* | H | $C_{8}H_{17}$-CH=CH-* | H |
| Compound 463 | S | S | $C_{9}H_{19}$-CH=CH-* | H | $C_{9}H_{19}$-CH=CH-* | H |
| Compound 464 | S | S | $C_{10}H_{21}$-CH=CH-* | H | $C_{10}H_{21}$-CH=CH-* | H |
| Compound 465 | S | S | $C_{11}H_{23}$-CH=CH-* | H | $C_{11}H_{23}$-CH=CH-* | H |
| Compound 466 | S | S | $C_{12}H_{25}$-CH=CH-* | H | $C_{12}H_{25}$-CH=CH-* | H |
| Compound 467 | S | S | $C_{13}H_{27}$-CH=CH-* | H | $C_{13}H_{27}$-CH=CH-* | H |
| Compound 468 | S | S | $C_{14}H_{29}$-CH=CH-* | H | $C_{14}H_{29}$-CH=CH-* | H |
| Compound 469 | S | S | $C_{15}H_{31}$-CH=CH-* | H | $C_{15}H_{31}$-CH=CH-* | H |
| Compound 470 | S | S | $C_{16}H_{33}$-CH=CH-* | H | $C_{16}H_{33}$-CH=CH-* | H |
| Compound 471 | S | S | $C_{17}H_{35}$-CH=CH-* | H | $C_{17}H_{35}$-CH=CH-* | H |

TABLE 19

| | $X^{a1}$ | $X^{a2}$ | $R^{a11}$ | $R^{a12}$ | $R^{a21}$ | $R^{a22}$ |
|---|---|---|---|---|---|---|
| Compound 472 | S | S | $C_{18}H_{37}$-CH=CH-* | H | $C_{18}H_{37}$-CH=CH-* | H |
| Compound 473 | S | S | $C_{5}H_{11}$-C≡C-* | H | $C_{5}H_{11}$-C≡C-* | H |
| Compound 474 | S | S | $C_{6}H_{13}$-C≡C-* | H | $C_{6}H_{13}$-C≡C-* | H |
| Compound 475 | S | S | $C_{7}H_{15}$-C≡C-* | H | $C_{7}H_{15}$-C≡C-* | H |

TABLE 19-continued

| | $X^{a1}$ | $X^{a2}$ | $R^{a11}$ | $R^{a12}$ | $R^{a21}$ | $R^{a22}$ |
|---|---|---|---|---|---|---|
| Compound 476 | S | S |  C$_8$H$_{17}$ | H |  C$_8$H$_{17}$ | H |
| Compound 477 | S | S |  C$_9$H$_{19}$ | H |  C$_9$H$_{19}$ | H |
| Compound 478 | S | S |  C$_{10}$H$_{21}$ | H |  C$_{10}$H$_{21}$ | H |
| Compound 479 | S | S |  C$_{11}$H$_{23}$ | H |  C$_{11}$H$_{23}$ | H |
| Compound 480 | S | S |  C$_{12}$H$_{25}$ | H |  C$_{12}$H$_{25}$ | H |
| Compound 481 | S | S |  C$_{13}$H$_{27}$ | H |  C$_{13}$H$_{27}$ | H |
| Compound 482 | S | S |  C$_{14}$H$_{29}$ | H |  C$_{14}$H$_{29}$ | H |
| Compound 483 | S | S |  C$_{15}$H$_{31}$ | H |  C$_{15}$H$_{31}$ | H |
| Compound 484 | S | S |  C$_{16}$H$_{33}$ | H |  C$_{16}$H$_{33}$ | H |
| Compound 485 | S | S |  C$_{17}$H$_{35}$ | H |  C$_{17}$H$_{35}$ | H |
| Compound 486 | S | S |  C$_{18}$H$_{37}$ | H |  C$_{18}$H$_{37}$ | H |
| Compound 487 | O | O | C$_5$H$_{11}$—* | H | C$_5$H$_{11}$—* | H |
| Compound 488 | O | O | C$_6$H$_{13}$—* | H | C$_6$H$_{13}$—* | H |
| Compound 489 | O | O | C$_7$H$_{15}$—* | H | C$_7$H$_{15}$—* | H |
| Compound 490 | O | O | C$_8$H$_{17}$—* | H | C$_8$H$_{17}$—* | H |
| Compound 491 | O | O | C$_9$H$_{19}$—* | H | C$_9$H$_{19}$—* | H |
| Compound 492 | O | O | C$_{10}$H$_{21}$—* | H | C$_{10}$H$_{21}$—* | H |
| Compound 493 | O | O | C$_{11}$H$_{23}$—* | H | C$_{11}$H$_{23}$—* | H |
| Compound 494 | O | O | C$_{12}$H$_{25}$—* | H | C$_{12}$H$_{25}$—* | H |
| Compound 495 | O | O | C$_{13}$H$_{27}$—* | H | C$_{13}$H$_{27}$—* | H |
| Compound 496 | O | O | C$_{14}$H$_{29}$—* | H | C$_{14}$H$_{29}$—* | H |
| Compound 497 | O | O | C$_{15}$H$_{31}$—* | H | C$_{15}$H$_{31}$—* | H |

TABLE 20

| | $X^{a1}$ | $X^{a2}$ | $R^{a11}$ | $R^{a12}$ | $R^{a21}$ | $R^{a22}$ |
|---|---|---|---|---|---|---|
| Compound 498 | O | O | C_{16}H_{33}—* | H | C_{16}H_{33}—* | H |
| Compound 499 | O | O | C_{17}H_{35}—* | H | C_{17}H_{35}—* | H |
| Compound 500 | O | O | C_{18}H_{37}—* | H | C_{18}H_{37}—* | H |
| Compound 501 | O | O | p-C_{5}H_{11}—Ph—* | H | p-C_{5}H_{11}—Ph—* | H |
| Compound 502 | O | O | p-C_{6}H_{13}—Ph—* | H | p-C_{6}H_{13}—Ph—* | H |
| Compound 503 | O | O | p-C_{7}H_{15}—Ph—* | H | p-C_{7}H_{15}—Ph—* | H |
| Compound 504 | O | O | p-C_{8}H_{17}—Ph—* | H | p-C_{8}H_{17}—Ph—* | H |
| Compound 505 | O | O | p-C_{9}H_{19}—Ph—* | H | p-C_{9}H_{19}—Ph—* | H |
| Compound 506 | O | O | p-C_{10}H_{21}—Ph—* | H | p-C_{10}H_{21}—Ph—* | H |
| Compound 507 | O | O | p-C_{11}H_{23}—Ph—* | H | p-C_{11}H_{23}—Ph—* | H |
| Compound 508 | O | O | p-C_{12}H_{25}—Ph—* | H | p-C_{12}H_{25}—Ph—* | H |
| Compound 509 | O | O | p-C_{13}H_{27}—Ph—* | H | p-C_{13}H_{27}—Ph—* | H |
| Compound 510 | O | O | p-C_{14}H_{29}—Ph—* | H | p-C_{14}H_{29}—Ph—* | H |
| Compound 511 | O | O | p-C_{15}H_{31}—Ph—* | H | p-C_{15}H_{31}—Ph—* | H |
| Compound 512 | O | O | p-C_{16}H_{33}—Ph—* | H | p-C_{16}H_{33}—Ph—* | H |
| Compound 513 | O | O | p-C_{17}H_{35}—Ph—* | H | p-C_{17}H_{35}—Ph—* | H |
| Compound 514 | O | O | p-C_{18}H_{37}—Ph—* | H | p-C_{18}H_{37}—Ph—* | H |
| Compound 515 | O | O |  C_{5}H_{11}-thiophene-* | H |  C_{5}H_{11}-thiophene-* | H |
| Compound 516 | O | O |  C_{6}H_{13}-thiophene-* | H |  C_{6}H_{13}-thiophene-* | H |
| Compound 517 | O | O |  C_{7}H_{15}-thiophene-* | H |  C_{7}H_{15}-thiophene-* | H |
| Compound 518 | O | O |  C_{8}H_{17}-thiophene-* | H |  C_{8}H_{17}-thiophene-* | H |
| Compound 519 | O | O |  C_{9}H_{19}-thiophene-* | H |  C_{9}H_{19}-thiophene-* | H |
| Compound 520 | O | O |  C_{10}H_{21}-thiophene-* | H |  C_{10}H_{21}-thiophene-* | H |
| Compound 521 | O | O |  C_{11}H_{23}-thiophene-* | H |  C_{11}H_{23}-thiophene-* | H |
| Compound 522 | O | O |  C_{12}H_{25}-thiophene-* | H |  C_{12}H_{25}-thiophene-* | H |
| Compound 523 | O | O |  C_{13}H_{27}-thiophene-* | H |  C_{13}H_{27}-thiophene-* | H |
| Compound 524 | O | O |  C_{14}H_{29}-thiophene-* | H |  C_{14}H_{29}-thiophene-* | H |
| Compound 525 | O | O |  C_{15}H_{31}-thiophene-* | H |  C_{15}H_{31}-thiophene-* | H |
| Compound 526 | O | O |  C_{16}H_{33}-thiophene-* | H |  C_{16}H_{33}-thiophene-* | H |

TABLE 21

| | $X^{a1}$ | $X^{a2}$ | $R^{a11}$ | $R^{a12}$ | $R^{a21}$ | $R^{a22}$ |
|---|---|---|---|---|---|---|
| Compound 527 | O | O |  | H |  | H |
| Compound 528 | O | O |  | H |  | H |
| Compound 529 | S | S | $C_4H_9OC_4H_8$—* | H | $C_4H_9OC_4H_8$—* | H |
| Compound 530 | S | S | $C_2H_5OC_2H_4$—* | H | $C_2H_5OC_2H_4$—* | H |
| Compound 531 | S | S | $C_6H_{13}OC_4H_8$—* | H | $C_6H_{13}OC_4H_8$—* | H |
| Compound 532 | S | S | $C_2H_5OC_4H_8$—* | H | $C_2H_5OC_4H_8$—* | H |
| Compound 533 | S | S | $CH_3OC_3H_6$—* | H | $CH_3OC_3H_6$—* | H |
| Compound 534 | S | S |  | H |  | H |
| Compound 535 | S | S | 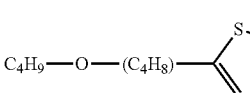 | H | 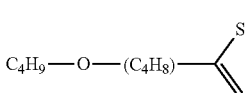 | H |
| Compound 536 | S | S | 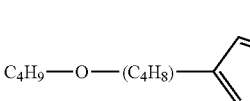 | H | 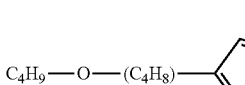 | H |
| Compound 537 | S | S | $PhC_3H_6$—* | H | $PhC_3H_6$—* | H |
| Compound 538 | S | S | $PhOC_3H_6$—* | H | $PhOC_3H_6$—* | H |
| Compound 539 | S | S | 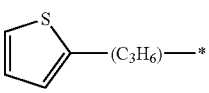 | H | 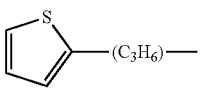 | H |
| Compound 540 | S | S | 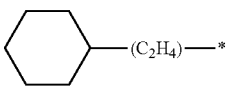 | H | 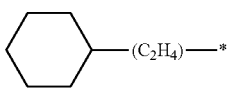 | H |
| Compound 541 | S | S | 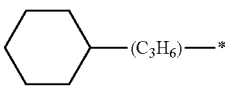 | H | 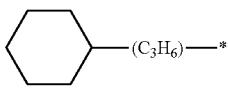 | H |
| Compound 542 | S | S | 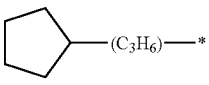 | H | 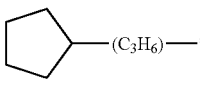 | H |
| Compound 543 | S | S | 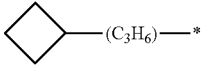 | H | 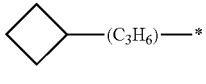 | H |
| Compound 544 | S | S | 3,7-Dimethyloctyl | H | 3,7-Dimethyloctyl | H |

TABLE 22

| | $X^{a1}$ | $X^{a2}$ | $R^{a11}$ | $R^{a12}$ | $R^{a21}$ | $R^{a22}$ |
|---|---|---|---|---|---|---|
| Compound 545 | S | S | 3,7-Dimethyloctyl | H | H | H |
| Compound 546 | S | S | 2-Ethylhexyl | H | 2-Ethylhexyl | H |

TABLE 22-continued

| | $X^{a1}$ | $X^{a2}$ | $R^{a11}$ | $R^{a12}$ | $R^{a21}$ | $R^{a22}$ |
|---|---|---|---|---|---|---|
| Compound 547 | S | S | (CH₃)₂CH-CH₂CH₂CH₂-CH(CH₃)-CH₂CH₂-C₆H₄-* | H | (CH₃)₂CH-CH₂CH₂CH₂-CH(CH₃)-CH₂CH₂-C₆H₄-* | H |
| Compound 548 | S | S | C₅H₁₁-C₆H₄-* | H | (CH₃)₂CH-CH₂CH₂CH₂-CH(CH₃)-CH₂CH₂-C₆H₄-* | H |
| Compound 549 | S | S | (CH₃)₃Si-C≡C-* | H | (CH₃)₃Si-C≡C-* | H |
| Compound 550 | S | S | (CH₃)₃Si-C≡C-* | H | H | H |
| Compound 551 | S | S | (CH₃)₃Si-O-Si(CH₃)₂-(CH₂)₆-* | H | (CH₃)₃Si-O-Si(CH₃)₂-(CH₂)₆-* | H |
| Compound 552 | S | S | C₅H₁₁-* | H | (CH₃)₃Si-O-Si(CH₃)₂-(CH₂)₆-* | H |
| Compound 553 | S | S | (CH₃)₃Si-O-Si(CH₃)₂-(CH₂)₆-C₆H₄-* | H | (CH₃)₃Si-O-Si(CH₃)₂-(CH₂)₆-C₆H₄-* | H |
| Compound 554 | S | S | C₅H₁₁-C₆H₄-* | H | (CH₃)₃Si-O-Si(CH₃)₂-(CH₂)₆-C₆H₄-* | H |
| Compound 555 | S | S | C₈H₁₇-C≡C-C₆H₄-* | H | C₈H₁₇-C≡C-C₆H₄-* | H |
| Compound 556 | S | S | C₈H₁₇-CH=CH-C₆H₄-* | H | C₈H₁₇-CH=CH-C₆H₄-* | H |
| Compound 557 | S | S | CH₂=CH-(CH₂)₅-* | H | CH₂=CH-(CH₂)₅-* | H |
| Compound 558 | S | S | CH₂=CH-(CH₂)₅-* | H | H | H |
| Compound 559 | S | S | CH₃CH₂-CH=CH-CH₂CH₂-* | H | CH₃CH₂-CH=CH-CH₂CH₂-* | H |
| Compound 560 | S | S | CH₃CH₂-CH=CH-CH₂CH₂-* (cis) | H | CH₃CH₂-CH=CH-CH₂CH₂-* (cis) | H |
| Compound 561 | S | S | CH₂=CH-(CH₂)₅-C₆H₄-* | H | CH₂=CH-(CH₂)₅-C₆H₄-* | H |

TABLE 22-continued

| | $X^{a1}$ | $X^{a2}$ | $R^{a11}$ | $R^{a12}$ | $R^{a21}$ | $R^{a22}$ |
|---|---|---|---|---|---|---|
| Compound 562 | S | S | $C_8H_{17}$—Ph—* | H | $CH_2$=$CH$—$(CH_2)_6$—Ph—* | H |

TABLE 23

| | $X^{b1}$ | $X^{b2}$ | $R^{b11}$ | $R^{b12}$ | $R^{b21}$ | $R^{b22}$ |
|---|---|---|---|---|---|---|
| Compound 563 | S | S | $C_5H_{11}$—* | H | $C_5H_{11}$—* | H |
| Compound 564 | S | S | $C_6H_{13}$—* | H | $C_6H_{13}$—* | H |
| Compound 565 | S | S | $C_7H_{15}$—* | H | $C_7H_{15}$—* | H |
| Compound 566 | S | S | $C_8H_{17}$—* | H | $C_8H_{17}$—* | H |
| Compound 567 | S | S | $C_9H_{19}$—* | H | $C_9H_{19}$—* | H |
| Compound 568 | S | S | $C_{10}H_{21}$—* | H | $C_{10}H_{21}$—* | H |
| Compound 569 | S | S | $C_{11}H_{23}$—* | H | $C_{11}H_{23}$—* | H |
| Compound 570 | S | S | $C_{12}H_{25}$—* | H | $C_{12}H_{25}$—* | H |
| Compound 571 | S | S | $C_{13}H_{27}$—* | H | $C_{13}H_{27}$—* | H |
| Compound 572 | S | S | $C_{14}H_{29}$—* | H | $C_{14}H_{29}$—* | H |
| Compound 573 | S | S | $C_{15}H_{31}$—* | H | $C_{15}H_{31}$—* | H |
| Compound 574 | S | S | $C_{16}H_{33}$—* | H | $C_{16}H_{33}$—* | H |
| Compound 575 | S | S | $C_{17}H_{35}$—* | H | $C_{17}H_{35}$—* | H |
| Compound 576 | S | S | $C_{18}H_{37}$—* | H | $C_{18}H_{37}$—* | H |
| Compound 577 | S | S | $C_5H_{11}$—* | $C_5H_{11}$—* | $C_5H_{11}$—* | $C_5H_{11}$—* |
| Compound 578 | S | S | $C_6H_{13}$—* | $C_6H_{13}$—* | $C_6H_{13}$—* | $C_6H_{13}$—* |
| Compound 579 | S | S | $C_7H_{15}$—* | $C_7H_{15}$—* | $C_7H_{15}$—* | $C_7H_{15}$—* |
| Compound 580 | S | S | $C_8H_{17}$—* | $C_8H_{17}$—* | $C_8H_{17}$—* | $C_8H_{17}$—* |
| Compound 581 | S | S | $C_9H_{19}$—* | $C_9H_{19}$—* | $C_9H_{19}$—* | $C_9H_{19}$—* |
| Compound 582 | S | S | $C_{10}H_{21}$—* | $C_{10}H_{21}$—* | $C_{10}H_{21}$—* | $C_{10}H_{21}$—* |
| Compound 583 | S | S | $C_{11}H_{23}$—* | $C_{11}H_{23}$—* | $C_{11}H_{23}$—* | $C_{11}H_{23}$—* |
| Compound 584 | S | S | $C_{12}H_{25}$—* | $C_{12}H_{25}$—* | $C_{12}H_{25}$—* | $C_{12}H_{25}$—* |
| Compound 585 | S | S | $C_{13}H_{27}$—* | $C_{13}H_{27}$—* | $C_{13}H_{27}$—* | $C_{13}H_{27}$—* |
| Compound 586 | S | S | $C_{14}H_{29}$—* | $C_{14}H_{29}$—* | $C_{14}H_{29}$—* | $C_{14}H_{29}$—* |
| Compound 587 | S | S | $C_{15}H_{31}$—* | $C_{15}H_{31}$—* | $C_{15}H_{31}$—* | $C_{15}H_{31}$—* |
| Compound 588 | S | S | $C_{16}H_{33}$—* | $C_{16}H_{33}$—* | $C_{16}H_{33}$—* | $C_{16}H_{33}$—* |
| Compound 589 | S | S | $C_{17}H_{35}$—* | $C_{17}H_{35}$—* | $C_{17}H_{35}$—* | $C_{17}H_{35}$—* |
| Compound 590 | S | S | $C_{18}H_{37}$—* | $C_{18}H_{37}$—* | $C_{18}H_{37}$—* | $C_{18}H_{37}$—* |
| Compound 591 | S | S | p-$C_5H_{11}$—Ph—* | H | p-$C_5H_{11}$—Ph—* | H |
| Compound 592 | S | S | p-$C_6H_{13}$—Ph—* | H | p-$C_6H_{13}$—Ph—* | H |
| Compound 593 | S | S | p-$C_7H_{15}$—Ph—* | H | p-$C_7H_{15}$—Ph—* | H |
| Compound 594 | S | S | p-$C_8H_{17}$—Ph—* | H | p-$C_8H_{17}$—Ph—* | H |
| Compound 595 | S | S | p-$C_9H_{19}$—Ph—* | H | p-$C_9H_{19}$—Ph—* | H |
| Compound 596 | S | S | p-$C_{10}H_{21}$—Ph—* | H | p-$C_{10}H_{21}$—Ph—* | H |
| Compound 597 | S | S | p-$C_{11}H_{23}$—Ph—* | H | p-$C_{11}H_{23}$—Ph—* | H |
| Compound 598 | S | S | p-$C_{12}H_{25}$—Ph—* | H | p-$C_{12}H_{25}$—Ph—* | H |
| Compound 599 | S | S | p-$C_{13}H_{27}$—Ph—* | H | p-$C_{13}H_{27}$—Ph—* | H |
| Compound 600 | S | S | p-$C_{14}H_{29}$—Ph—* | H | p-$C_{14}H_{29}$—Ph—* | H |
| Compound 601 | S | S | p-$C_{15}H_{31}$—Ph—* | H | p-$C_{15}H_{31}$—Ph—* | H |
| Compound 602 | S | S | p-$C_{16}H_{33}$—Ph—* | H | p-$C_{16}H_{33}$—Ph—* | H |
| Compound 603 | S | S | p-$C_{17}H_{35}$—Ph—* | H | p-$C_{17}H_{35}$—Ph—* | H |
| Compound 604 | S | S | p-$C_{18}H_{37}$—Ph—* | H | p-$C_{18}H_{37}$—Ph—* | H |
| Compound 605 | S | S | p-$C_5H_{11}$—Ph—* | p-$C_5H_{11}$—Ph—* | p-$C_5H_{11}$—Ph—* | p-$C_5H_{11}$—Ph—* |
| Compound 606 | S | S | p-$C_6H_{13}$—Ph—* | p-$C_6H_{13}$—Ph—* | p-$C_6H_{13}$—Ph—* | p-$C_6H_{13}$—Ph—* |
| Compound 607 | S | S | p-$C_7H_{15}$—Ph—* | p-$C_7H_{15}$—Ph—* | p-$C_7H_{15}$—Ph—* | p-$C_7H_{15}$—Ph—* |
| Compound 608 | S | S | p-$C_8H_{17}$—Ph—* | p-$C_8H_{17}$—Ph—* | p-$C_8H_{17}$—Ph—* | p-$C_8H_{17}$—Ph—* |
| Compound 609 | S | S | p-$C_9H_{19}$—Ph—* | p-$C_9H_{19}$—Ph—* | p-$C_9H_{19}$—Ph—* | p-$C_9H_{19}$—Ph—* |
| Compound 610 | S | S | p-$C_{10}H_{21}$—Ph—* | p-$C_{10}H_{21}$—Ph—* | p-$C_{10}H_{21}$—Ph—* | p-$C_{10}H_{21}$—Ph—* |
| Compound 611 | S | S | p-$C_{11}H_{23}$—Ph—* | p-$C_{11}H_{23}$—Ph—* | p-$C_{11}H_{23}$—Ph—* | p-$C_{11}H_{23}$—Ph—* |
| Compound 612 | S | S | p-$C_{12}H_{25}$—Ph—* | p-$C_{12}H_{25}$—Ph—* | p-$C_{12}H_{25}$—Ph—* | p-$C_{12}H_{25}$—Ph—* |
| Compound 613 | S | S | p-$C_{13}H_{27}$—Ph—* | p-$C_{13}H_{27}$—Ph—* | p-$C_{13}H_{27}$—Ph—* | p-$C_{13}H_{27}$—Ph—* |

TABLE 24

| | $X^{a1}$ | $X^{a2}$ | $R^{a11}$ | $R^{a12}$ | $R^{a21}$ | $R^{a22}$ |
|---|---|---|---|---|---|---|
| Compound 614 | S | S | p-$C_{14}H_{29}$—Ph—* | p-$C_{14}H_{29}$—Ph—* | p-$C_{14}H_{29}$—Ph—* | p-$C_{14}H_{29}$—Ph—* |
| Compound 615 | S | S | p-$C_{15}H_{31}$—Ph—* | p-$C_{15}H_{31}$—Ph—* | p-$C_{15}H_{31}$—Ph—* | p-$C_{15}H_{31}$—Ph—* |
| Compound 616 | S | S | p-$C_{16}H_{33}$—Ph—* | p-$C_{16}H_{33}$—Ph—* | p-$C_{16}H_{33}$—Ph—* | p-$C_{16}H_{33}$—Ph—* |
| Compound 617 | S | S | p-$C_{17}H_{35}$—Ph—* | p-$C_{17}H_{35}$—Ph—* | p-$C_{17}H_{35}$—Ph—* | p-$C_{17}H_{35}$—Ph—* |
| Compound 618 | S | S | p-$C_{18}H_{37}$—Ph—* | p-$C_{18}H_{37}$—Ph—* | p-$C_{18}H_{37}$—Ph—* | p-$C_{18}H_{37}$—Ph—* |

TABLE 24-continued

| | $X^{a1}$ | $X^{a2}$ | $R^{a11}$ | $R^{a12}$ | $R^{a21}$ | $R^{a22}$ |
|---|---|---|---|---|---|---|
| Compound 619 | S | S | 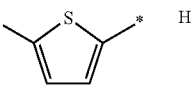 C$_5$H$_{11}$-thienyl* | H | 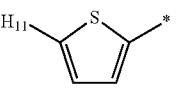 C$_5$H$_{11}$-thienyl* | H |
| Compound 620 | S | S | C$_6$H$_{13}$-thienyl* | H | C$_6$H$_{13}$-thienyl* | H |
| Compound 621 | S | S | C$_7$H$_{15}$-thienyl* | H | C$_7$H$_{15}$-thienyl* | H |
| Compound 622 | S | S | C$_8$H$_{17}$-thienyl* | H | C$_8$H$_{17}$-thienyl* | H |
| Compound 623 | S | S | C$_9$H$_{19}$-thienyl* | H | C$_9$H$_{19}$-thienyl* | H |
| Compound 624 | S | S | C$_{10}$H$_{21}$-thienyl* | H | C$_{10}$H$_{21}$-thienyl* | H |
| Compound 625 | S | S | C$_{11}$H$_{23}$-thienyl* | H | C$_{11}$H$_{23}$-thienyl* | H |
| Compound 626 | S | S | C$_{12}$H$_{25}$-thienyl* | H | C$_{12}$H$_{25}$-thienyl* | H |
| Compound 627 | S | S | C$_{13}$H$_{27}$-thienyl* | H | C$_{13}$H$_{27}$-thienyl* | H |
| Compound 628 | S | S | C$_{14}$H$_{29}$-thienyl* | H | C$_{14}$H$_{29}$-thienyl* | H |
| Compound 629 | S | S | C$_{15}$H$_{31}$-thienyl* | H | C$_{15}$H$_{31}$-thienyl* | H |
| Compound 630 | S | S | C$_{16}$H$_{33}$-thienyl* | H | C$_{16}$H$_{33}$-thienyl* | H |
| Compound 631 | S | S | C$_{17}$H$_{35}$-thienyl* | H | C$_{17}$H$_{35}$-thienyl* | H |
| Compound 632 | S | S | C$_{18}$H$_{37}$-thienyl* | H | C$_{18}$H$_{37}$-thienyl* | H |
| Compound 633 | S | S | C$_5$H$_{11}$-thienyl* | C$_5$H$_{11}$-thienyl* | C$_5$H$_{11}$-thienyl* | C$_5$H$_{11}$-thienyl* |
| Compound 634 | S | S | C$_6$H$_{13}$-thienyl* | C$_6$H$_{13}$-thienyl* | C$_6$H$_{13}$-thienyl* | C$_5$H$_{11}$-thienyl* |

TABLE 24-continued

| | $X^{a1}$ | $X^{a2}$ | $R^{a11}$ | $R^{a12}$ | $R^{a21}$ | $R^{a22}$ |
|---|---|---|---|---|---|---|
| Compound 635 | S | S | C₇H₁₅-thiophene-* | C₇H₁₅-thiophene-* | C₇H₁₅-thiophene-* | C₇H₁₅-thiophene-* |

TABLE 25

| | $X^{a1}$ | $X^{a2}$ | $R^{a11}$ | $R^{a12}$ | $R^{a21}$ | $R^{a22}$ |
|---|---|---|---|---|---|---|
| Compound 636 | S | S | C₈H₁₇-thiophene-* | C₈H₁₇-thiophene-* | C₈H₁₇-thiophene-* | C₈H₁₇-thiophene-* |
| Compound 637 | S | S | C₉H₁₉-thiophene-* | C₉H₁₉-thiophene-* | C₉H₁₉-thiophene-* | C₉H₁₉-thiophene-* |
| Compound 638 | S | S | C₁₀H₂₁-thiophene-* | C₁₀H₂₁-thiophene-* | C₁₀H₂₁-thiophene-* | C₁₀H₂₁-thiophene-* |
| Compound 639 | S | S | C₁₁H₂₃-thiophene-* | C₁₁H₂₃-thiophene-* | C₁₁H₂₃-thiophene-* | C₁₁H₂₃-thiophene-* |
| Compound 640 | S | S | C₁₂H₂₅-thiophene-* | C₁₂H₂₅-thiophene-* | C₁₂H₂₅-thiophene-* | C₁₂H₂₅-thiophene-* |
| Compound 641 | S | S | C₁₃H₂₇-thiophene-* | C₁₃H₂₇-thiophene-* | C₁₃H₂₇-thiophene-* | C₁₃H₂₇-thiophene-* |
| Compound 642 | S | S | C₁₄H₂₉-thiophene-* | C₁₄H₂₉-thiophene-* | C₁₄H₂₉-thiophene-* | C₁₄H₂₉-thiophene-* |
| Compound 643 | S | S | C₁₅H₃₁-thiophene-* | C₁₅H₃₁-thiophene-* | C₁₆H₃₃-thiophene-* | C₁₅H₃₁-thiophene-* |
| Compound 644 | S | S | C₁₆H₃₃-thiophene-* | C₁₆H₃₃-thiophene-* | C₁₆H₃₃-thiophene-* | C₁₆H₃₃-thiophene-* |
| Compound 645 | S | S | C₁₇H₃₅-thiophene-* | C₁₇H₃₅-thiophene-* | C₁₇H₃₅-thiophene-* | C₁₇H₃₅-thiophene-* |
| Compound 646 | S | S | C₁₈H₃₇-thiophene-* | C₁₈H₃₇-thiophene-* | C₁₈H₃₇-thiophene-* | C₁₈H₃₇-thiophene-* |
| Compound 647 | S | S | 4-C₅H₁₁-thiophene-2-* | H | 4-C₅H₁₁-thiophene-2-* | H |
| Compound 648 | S | S | 4-C₆H₁₃-thiophene-2-* | H | 4-C₆H₁₃-thiophene-2-* | H |

TABLE 25-continued

| | $X^{a1}$ | $X^{a2}$ | $R^{a11}$ | $R^{a12}$ | $R^{a21}$ | $R^{a22}$ |
|---|---|---|---|---|---|---|
| Compound 649 | S | S | 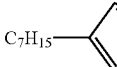 C7H15-thiophene-* | H | 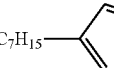 C7H15-thiophene-* | H |
| Compound 650 | S | S | 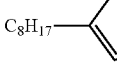 C8H17-thiophene-* | H | 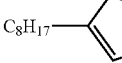 C8H17-thiophene-* | H |
| Compound 651 | S | S | 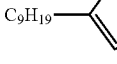 C9H19-thiophene-* | H | 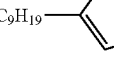 C9H19-thiophene-* | H |
| Compound 652 | S | S | 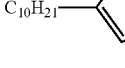 C10H21-thiophene-* | H | 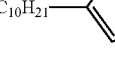 C10H21-thiophene-* | H |
| Compound 653 | S | S | 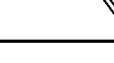 C11H23-thiophene-* | H | 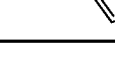 C11H23-thiophene-* | H |

TABLE 26

| | $X^{a1}$ | $X^{a2}$ | $R^{a11}$ | $R^{a12}$ | $R^{a21}$ | $R^{a22}$ |
|---|---|---|---|---|---|---|
| Compound 654 | S | S | 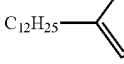 C12H25-thiophene-* | H | 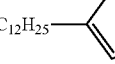 C12H25-thiophene-* | H |
| Compound 655 | S | S | 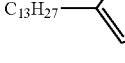 C13H27-thiophene-* | H | 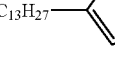 C13H27-thiophene-* | H |
| Compound 656 | S | S | 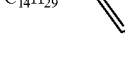 C14H29-thiophene-* | H | 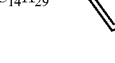 C14H29-thiophene-* | H |
| Compound 657 | S | S |  C15H31-thiophene-* | H |  C15H31-thiophene-* | H |
| Compound 658 | S | S |  C16H33-thiophene-* | H |  C16H33-thiophene-* | H |
| Compound 659 | S | S |  C17H35-thiophene-* | H |  C17H35-thiophene-* | H |
| Compound 660 | S | S | 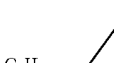 C18H37-thiophene-* | H | 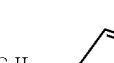 C18H37-thiophene-* | H |
| Compound 661 | S | S |  C5H11-thiophene-* |  C5H11-thiophene-* | C5H11-thiophene-* | C5H11-thiophene-* |

TABLE 26-continued

| | $X^{a1}$ | $X^{a2}$ | $R^{a11}$ | $R^{a12}$ | $R^{a21}$ | $R^{a22}$ |
|---|---|---|---|---|---|---|
| Compound 662 | S | S | 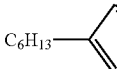 C$_6$H$_{13}$— | 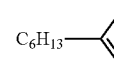 C$_6$H$_{13}$— | 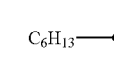 C$_6$H$_{13}$— | 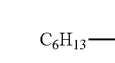 C$_6$H$_{13}$— |
| Compound 663 | S | S | 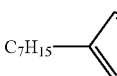 C$_7$H$_{15}$— | 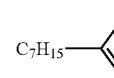 C$_7$H$_{15}$— | 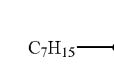 C$_7$H$_{15}$— | 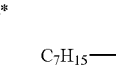 C$_7$H$_{15}$— |
| Compound 664 | S | S | 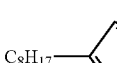 C$_8$H$_{17}$— | 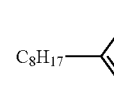 C$_8$H$_{17}$— | 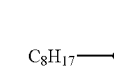 C$_8$H$_{17}$— | 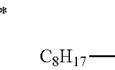 C$_8$H$_{17}$— |
| Compound 665 | S | S | 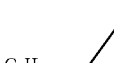 C$_9$H$_{19}$— |  C$_9$H$_{19}$— |  C$_9$H$_{19}$— |  C$_9$H$_{19}$— |
| Compound 666 | S | S |  C$_{10}$H$_{21}$— |  C$_{10}$H$_{21}$— |  C$_{10}$H$_{21}$— |  C$_{10}$H$_{21}$— |
| Compound 667 | S | S |  C$_{11}$H$_{23}$— |  C$_{11}$H$_{23}$— |  C$_{11}$H$_{23}$— |  C$_{11}$H$_{23}$— |
| Compound 668 | S | S |  C$_{12}$H$_{25}$— |  C$_{12}$H$_{25}$— |  C$_{12}$H$_{25}$— |  C$_{12}$H$_{25}$— |
| Compound 669 | S | S |  C$_{13}$H$_{27}$— |  C$_{13}$H$_{27}$— |  C$_{13}$H$_{27}$— |  C$_{13}$H$_{27}$— |
| Compound 670 | S | S | 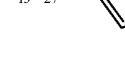 C$_{14}$H$_{29}$— |  C$_{14}$H$_{29}$— | 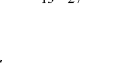 C$_{14}$H$_{29}$— | 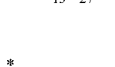 C$_{14}$H$_{29}$— |
| Compound 671 | S | S | 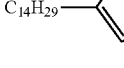 C$_{15}$H$_{31}$— | 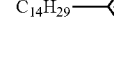 C$_{15}$H$_{31}$— | 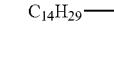 C$_{15}$H$_{31}$— | 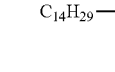 C$_{15}$H$_{31}$— |

TABLE 27

| | $X^{a1}$ | $X^{a2}$ | $R^{a11}$ | $R^{a12}$ | $R^{a21}$ | $R^{a22}$ |
|---|---|---|---|---|---|---|
| Compound 672 | S | S | 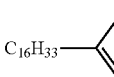 C$_{16}$H$_{33}$— | 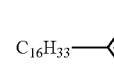 C$_{16}$H$_{33}$— | 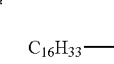 C$_{16}$H$_{33}$— | 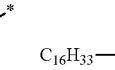 C$_{16}$H$_{33}$— |
| Compound 673 | S | S | 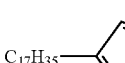 C$_{17}$H$_{35}$— | 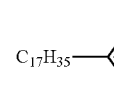 C$_{17}$H$_{35}$— | 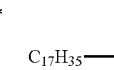 C$_{17}$H$_{35}$— | 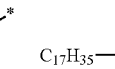 C$_{17}$H$_{35}$— |
| Compound 674 | S | S |  C$_{18}$H$_{37}$— | 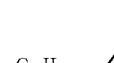 C$_{18}$H$_{37}$— |  C$_{18}$H$_{37}$— |  C$_{18}$H$_{37}$— |

TABLE 27-continued

| | $X^{a1}$ | $X^{a2}$ | $R^{a11}$ | $R^{a12}$ | $R^{a21}$ | $R^{a22}$ |
|---|---|---|---|---|---|---|
| Compound 675 | S | S | H | $C_5H_{11}$—* | H | $C_5H_{11}$—* |
| Compound 676 | S | S | H | $C_6H_{13}$—* | H | $C_6H_{13}$—* |
| Compound 677 | S | S | H | $C_7H_{15}$—* | H | $C_7H_{15}$—* |
| Compound 678 | S | S | H | $C_8H_{17}$—* | H | $C_8H_{17}$—* |
| Compound 679 | S | S | H | $C_9H_{19}$—* | H | $C_9H_{19}$—* |
| Compound 680 | S | S | H | $C_{10}H_{21}$—* | H | $C_{10}H_{21}$—* |
| Compound 681 | S | S | H | $C_{11}H_{23}$—* | H | $C_{11}H_{23}$—* |
| Compound 682 | S | S | H | $C_{12}H_{25}$—* | H | $C_{12}H_{25}$—* |
| Compound 683 | S | S | H | $C_{13}H_{27}$—* | H | $C_{13}H_{27}$—* |
| Compound 684 | S | S | H | $C_{14}H_{29}$—* | H | $C_{14}H_{29}$—* |
| Compound 685 | S | S | H | $C_{15}H_{31}$—* | H | $C_{15}H_{31}$—* |
| Compound 686 | S | S | H | $C_{16}H_{33}$—* | H | $C_{16}H_{33}$—* |
| Compound 687 | S | S | H | $C_{17}H_{35}$—* | H | $C_{17}H_{35}$—* |
| Compound 688 | S | S | H | $C_{18}H_{37}$—* | H | $C_{18}H_{37}$—* |
| Compound 689 | S | S | H | p-$C_5H_{11}$—Ph—* | H | p-$C_5H_{11}$—Ph—* |
| Compound 690 | S | S | H | p-$C_6H_{13}$—Ph—* | H | p-$C_6H_{13}$—Ph—* |
| Compound 691 | S | S | H | p-$C_7H_{15}$—Ph—* | H | p-$C_7H_{15}$—Ph—* |
| Compound 692 | S | S | H | p-$C_8H_{17}$—Ph—* | H | p-$C_8H_{17}$—Ph—* |
| Compound 693 | S | S | H | p-$C_9H_{19}$—Ph—* | H | p-$C_9H_{19}$—Ph—* |
| Compound 694 | S | S | H | p-$C_{10}H_{21}$—Ph—* | H | p-$C_{10}H_{21}$—Ph—* |
| Compound 695 | S | S | H | p-$C_{11}H_{23}$—Ph—* | H | p-$C_{11}H_{23}$—Ph—* |
| Compound 696 | S | S | H | p-$C_{12}H_{25}$—Ph—* | H | p-$C_{12}H_{25}$—Ph—* |
| Compound 697 | S | S | H | p-$C_{13}H_{27}$—Ph—* | H | p-$C_{13}H_{27}$—Ph—* |
| Compound 698 | S | S | H | p-$C_{14}H_{29}$—Ph—* | H | p-$C_{14}H_{29}$—Ph—* |
| Compound 699 | S | S | H | p-$C_{15}H_{31}$—Ph—* | H | p-$C_{15}H_{31}$—Ph—* |
| Compound 700 | S | S | H | p-$C_{16}H_{33}$—Ph—* | H | p-$C_{16}H_{33}$—Ph—* |
| Compound 701 | S | S | H | p-$C_{17}H_{35}$—Ph—* | H | p-$C_{17}H_{35}$—Ph—* |
| Compound 702 | S | S | H | p-$C_{18}H_{37}$—Ph—* | H | p-$C_{18}H_{37}$—Ph—* |
| Compound 703 | S | S | H | 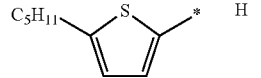 | H | 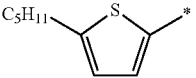 |
| Compound 704 | S | S | H | 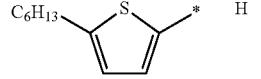 | H | 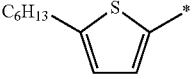 |
| Compound 705 | S | S | H | 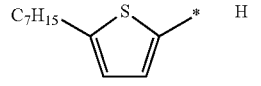 | H | 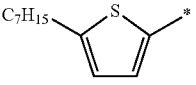 |
| Compound 706 | S | S | H | 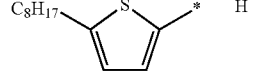 | H | 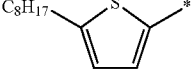 |
| Compound 707 | S | S | H | 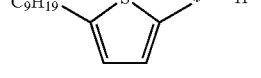 | H | 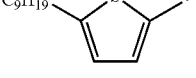 |

TABLE 28

| | $X^{a1}$ | $X^{a2}$ | $R^{a11}$ | $R^{a12}$ | $R^{a21}$ | $R^{a22}$ |
|---|---|---|---|---|---|---|
| Compound 708 | S | S | H | 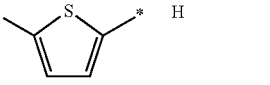 | H | 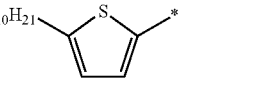 |
| Compound 709 | S | S | H | 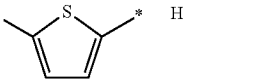 | H | 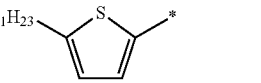 |
| Compound 710 | S | S | H | 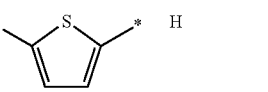 | H | 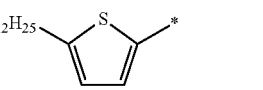 |

TABLE 28-continued

| | $X^{a1}$ | $X^{a2}$ | $R^{a11}$ | $R^{a12}$ | $R^{a21}$ | $R^{a22}$ |
|---|---|---|---|---|---|---|
| Compound 711 | S | S | H | $C_{13}H_{27}$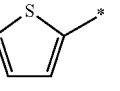* | H | $C_{13}H_{27}$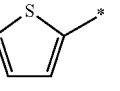* |
| Compound 712 | S | S | H | $C_{14}H_{29}$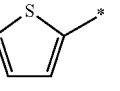* | H | $C_{14}H_{29}$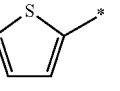* |
| Compound 713 | S | S | H | $C_{15}H_{31}$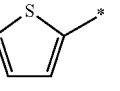* | H | $C_{15}H_{31}$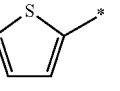* |
| Compound 714 | S | S | H | $C_{16}H_{33}$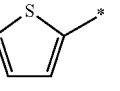* | H | $C_{16}H_{33}$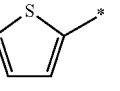* |
| Compound 715 | S | S | H | $C_{17}H_{35}$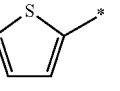* | H | $C_{17}H_{35}$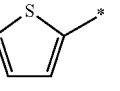* |
| Compound 716 | S | S | H | $C_{18}H_{37}$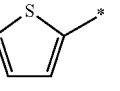* | H | $C_{18}H_{37}$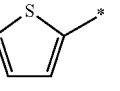* |
| Compound 717 | S | S | H | H | $C_5H_{11}$—* | H |
| Compound 718 | S | S | H | H | $C_6H_{13}$—* | H |
| Compound 719 | S | S | H | H | $C_7H_{15}$—* | H |
| Compound 720 | S | S | H | H | $C_8H_{17}$—* | H |
| Compound 721 | S | S | H | H | $C_9H_{19}$—* | H |
| Compound 722 | S | S | H | H | $C_{10}H_{21}$—* | H |
| Compound 723 | S | S | H | H | $C_{11}H_{23}$—* | H |
| Compound 724 | S | S | H | H | $C_{12}H_{25}$—* | H |
| Compound 725 | S | S | H | H | $C_{13}H_{27}$—* | H |
| Compound 726 | S | S | H | H | $C_{14}H_{29}$—* | H |
| Compound 727 | S | S | H | H | $C_{15}H_{31}$—* | H |
| Compound 728 | S | S | H | H | $C_{16}H_{33}$—* | H |
| Compound 729 | S | S | H | H | $C_{17}H_{35}$—* | H |
| Compound 730 | S | S | H | H | $C_{18}H_{37}$—* | H |
| Compound 731 | S | S | Ph | H | $C_5H_{11}$—* | H |
| Compound 732 | S | S | Ph | H | $C_6H_{13}$—* | H |
| Compound 733 | S | S | Ph | H | $C_7H_{15}$—* | H |
| Compound 734 | S | S | Ph | H | $C_8H_{17}$—* | H |
| Compound 735 | S | S | Ph | H | $C_9H_{19}$—* | H |
| Compound 736 | S | S | Ph | H | $C_{10}H_{21}$—* | H |
| Compound 737 | S | S | Ph | H | $C_{11}H_{23}$—* | H |
| Compound 738 | S | S | Ph | H | $C_{12}H_{25}$—* | H |
| Compound 739 | S | S | Ph | H | $C_{13}H_{27}$—* | H |
| Compound 740 | S | S | Ph | H | $C_{14}H_{29}$—* | H |
| Compound 741 | S | S | Ph | H | $C_{15}H_{31}$—* | H |
| Compound 742 | S | S | Ph | H | $C_{16}H_{33}$—* | H |
| Compound 743 | S | S | Ph | H | $C_{17}H_{35}$—* | H |

TABLE 29

| | $X^{a1}$ | $X^{a2}$ | $R^{a11}$ | $R^{a12}$ | $R^{a21}$ | $R^{a22}$ |
|---|---|---|---|---|---|---|
| Compound 744 | S | S | Ph | H | $C_{18}H_{37}$—* | H |
| Compound 745 | S | S | 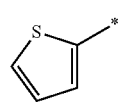* | H | $C_5H_{11}$—* | H |
| Compound 746 | S | S | 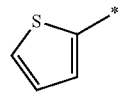* | H | $C_6H_{13}$—* | H |

TABLE 29-continued

| | $X^{a1}$ | $X^{a2}$ | $R^{a11}$ | $R^{a12}$ | $R^{a21}$ | $R^{a22}$ |
|---|---|---|---|---|---|---|
| Compound 747 | S | S | 2-thienyl | H | $C_7H_{15}$—* | H |
| Compound 748 | S | S | 2-thienyl | H | $C_8H_{17}$—* | H |
| Compound 749 | S | S | 2-thienyl | H | $C_9H_{19}$—* | H |
| Compound 750 | S | S | 2-thienyl | H | $C_{10}H_{21}$—* | H |
| Compound 751 | S | S | 2-thienyl | H | $C_{11}H_{23}$—* | H |
| Compound 752 | S | S | 2-thienyl | H | $C_{12}H_{25}$—* | H |
| Compound 753 | S | S | 2-thienyl | H | $C_{13}H_{27}$—* | H |
| Compound 754 | S | S | 2-thienyl | H | $C_{14}H_{29}$—* | H |
| Compound 755 | S | S | 2-thienyl | H | $C_{15}H_{31}$—* | H |
| Compound 756 | S | S | 2-thienyl | H | $C_{16}H_{33}$—* | H |
| Compound 757 | S | S | 2-thienyl | H | $C_{17}H_{35}$—* | H |
| Compound 758 | S | S | 2-thienyl | H | $C_{18}H_{37}$—* | H |
| Compound 759 | S | S | H | H | H | $C_5H_{11}$—* |
| Compound 760 | S | S | H | H | H | $C_6H_{13}$—* |
| Compound 761 | S | S | H | H | H | $C_7H_{15}$—* |
| Compound 762 | S | S | H | H | H | $C_8H_{17}$—* |
| Compound 763 | S | S | H | H | H | $C_9H_{19}$—* |
| Compound 764 | S | S | H | H | H | $C_{10}H_{21}$—* |
| Compound 765 | S | S | H | H | H | $C_{11}H_{23}$—* |
| Compound 766 | S | S | H | H | H | $C_{12}H_{25}$—* |
| Compound 767 | S | S | H | H | H | $C_{13}H_{27}$—* |
| Compound 768 | S | S | H | H | H | $C_{14}H_{29}$—* |
| Compound 769 | S | S | H | H | H | $C_{15}H_{31}$—* |
| Compound 770 | S | S | H | H | H | $C_{16}H_{33}$—* |
| Compound 771 | S | S | H | H | H | $C_{17}H_{35}$—* |

TABLE 30

| | $X^{b1}$ | $X^{b2}$ | $R^{b11}$ | $R^{b12}$ | $R^{b21}$ | $R^{b22}$ |
|---|---|---|---|---|---|---|
| Compound 772 | S | S | H | H | H | $C_{18}H_{37}$—* |
| Compound 773 | S | S | H | H | p-$C_5H_{11}$—Ph—* | H |
| Compound 774 | S | S | H | H | p-$C_6H_{13}$—Ph—* | H |
| Compound 775 | S | S | H | H | p-$C_7H_{15}$—Ph—* | H |
| Compound 776 | S | S | H | H | p-$C_8H_{17}$—Ph—* | H |
| Compound 777 | S | S | H | H | p-$C_9H_{19}$—Ph—* | H |
| Compound 778 | S | S | H | H | p-$C_{10}H_{21}$—Ph—* | H |
| Compound 779 | S | S | H | H | p-$C_{11}H_{23}$—Ph—* | H |
| Compound 780 | S | S | H | H | p-$C_{12}H_{25}$—Ph—* | H |
| Compound 781 | S | S | H | H | p-$C_{13}H_{27}$—Ph—* | H |
| Compound 782 | S | S | H | H | p-$C_{14}H_{29}$—Ph—* | H |
| Compound 783 | S | S | H | H | p-$C_{15}H_{31}$—Ph—* | H |
| Compound 784 | S | S | H | H | p-$C_{16}H_{33}$—Ph—* | H |
| Compound 785 | S | S | H | H | p-$C_{17}H_{35}$—Ph—* | H |
| Compound 786 | S | S | H | H | p-$C_{18}H_{37}$—Ph—* | H |
| Compound 787 | S | S | Ph | H | p-$C_5H_{11}$—Ph—* | H |
| Compound 788 | S | S | Ph | H | p-$C_6H_{13}$—Ph—* | H |
| Compound 789 | S | S | Ph | H | p-$C_7H_{15}$—Ph—* | H |
| Compound 790 | S | S | Ph | H | p-$C_8H_{17}$—Ph—* | H |
| Compound 791 | S | S | Ph | H | p-$C_9H_{19}$—Ph—* | H |
| Compound 792 | S | S | Ph | H | p-$C_{10}H_{21}$—Ph—* | H |
| Compound 793 | S | S | Ph | H | p-$C_{11}H_{23}$—Ph—* | H |
| Compound 794 | S | S | Ph | H | p-$C_{12}H_{25}$—Ph—* | H |
| Compound 795 | S | S | Ph | H | p-$C_{13}H_{27}$—Ph—* | H |
| Compound 796 | S | S | Ph | H | p-$C_{14}H_{29}$—Ph—* | H |
| Compound 797 | S | S | Ph | H | p-$C_{15}H_{31}$—Ph—* | H |
| Compound 798 | S | S | Ph | H | p-$C_{16}H_{33}$—Ph—* | H |
| Compound 799 | S | S | Ph | H | p-$C_{17}H_{35}$—Ph—* | H |
| Compound 800 | S | S | Ph | H | p-$C_{18}H_{37}$—Ph—* | H |
| Compound 801 | S | S |  | H | p-$C_5H_{11}$—Ph—* | H |
| Compound 802 | S | S |  | H | p-$C_6H_{13}$—Ph—* | H |
| Compound 803 | S | S |  | H | p-$C_7H_{15}$—Ph—* | H |
| Compound 804 | S | S |  | H | p-$C_8H_{17}$—Ph—* | H |
| Compound 805 | S | S |  | H | p-$C_9H_{19}$—Ph—* | H |
| Compound 806 | S | S |  | H | p-$C_{10}H_{21}$—Ph—* | H |
| Compound 807 | S | S |  | H | p-$C_{11}H_{23}$—Ph—* | H |

TABLE 31

| | $X^{b1}$ | $X^{b2}$ | $R^{b11}$ | $R^{b12}$ | $R^{b21}$ | $R^{b22}$ |
|---|---|---|---|---|---|---|
| Compound 808 | S | S |  | H | p-$C_{12}H_{25}$—Ph—* | H |
| Compound 809 | S | S |  | H | p-$C_{13}H_{27}$—Ph—* | H |
| Compound 810 | S | S |  | H | p-$C_{14}H_{29}$—Ph—* | H |
| Compound 811 | S | S |  | H | p-$C_{15}H_{31}$—Ph—* | H |
| Compound 812 | S | S |  | H | p-$C_{16}H_{33}$—Ph—* | H |
| Compound 813 | S | S |  | H | p-$C_{17}H_{35}$—Ph—* | H |
| Compound 814 | S | S |  | H | p-$C_{18}H_{37}$—Ph—* | H |
| Compound 815 | S | S | H | H | H | p-$C_5H_{11}$—Ph—* |
| Compound 816 | S | S | H | H | H | p-$C_6H_{13}$—Ph—* |
| Compound 817 | S | S | H | H | H | p-$C_7H_{15}$—Ph—* |
| Compound 818 | S | S | H | H | H | p-$C_8H_{17}$—Ph—* |
| Compound 819 | S | S | H | H | H | p-$C_9H_{19}$—Ph—* |
| Compound 820 | S | S | H | H | H | p-$C_{10}H_{21}$—Ph—* |
| Compound 821 | S | S | H | H | H | p-$C_{11}H_{23}$—Ph—* |
| Compound 822 | S | S | H | H | H | p-$C_{12}H_{25}$—Ph—* |
| Compound 823 | S | S | H | H | H | p-$C_{13}H_{27}$—Ph—* |
| Compound 824 | S | S | H | H | H | p-$C_{14}H_{29}$—Ph—* |
| Compound 825 | S | S | H | H | H | p-$C_{15}H_{31}$—Ph—* |
| Compound 826 | S | S | H | H | H | p-$C_{16}H_{33}$—Ph—* |
| Compound 827 | S | S | H | H | H | p-$C_{17}H_{35}$—Ph—* |
| Compound 828 | S | S | H | H | H | p-$C_{18}H_{37}$—Ph—* |
| Compound 829 | S | S | H | H | 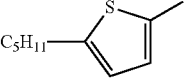 | H |
| Compound 830 | S | S | H | H | 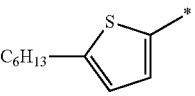 | H |
| Compound 831 | S | S | H | H | 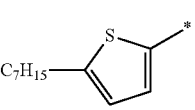 | H |
| Compound 832 | S | S | H | H | 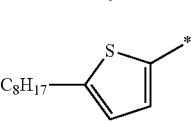 | H |

TABLE 31-continued

| | $X^{b1}$ | $X^{b2}$ | $R^{b11}$ | $R^{b12}$ | $R^{b21}$ | $R^{b22}$ |
|---|---|---|---|---|---|---|
| Compound 833 | S | S | H | H | 5-C$_9$H$_{19}$-thiophen-2-yl* | H |
| Compound 834 | S | S | H | H | 5-C$_{10}$H$_{21}$-thiophen-2-yl* | H |

TABLE 32

| | $X^{b1}$ | $X^{b2}$ | $R^{b11}$ | $R^{b12}$ | $R^{b21}$ | $R^{b22}$ |
|---|---|---|---|---|---|---|
| Compound 835 | S | S | H | H | 5-C$_{11}$H$_{23}$-thiophen-2-yl* | H |
| Compound 836 | S | S | H | H | 5-C$_{12}$H$_{25}$-thiophen-2-yl* | H |
| Compound 837 | S | S | H | H | 5-C$_{13}$H$_{27}$-thiophen-2-yl* | H |
| Compound 838 | S | S | H | H | 5-C$_{14}$H$_{29}$-thiophen-2-yl* | H |
| Compound 839 | S | S | H | H | 5-C$_{15}$H$_{31}$-thiophen-2-yl* | H |
| Compound 840 | S | S | H | H | 5-C$_{16}$H$_{33}$-thiophen-2-yl* | H |
| Compound 841 | S | S | H | H | 5-C$_{17}$H$_{35}$-thiophen-2-yl* | H |
| Compound 842 | S | S | Ph | H | 5-C$_5$H$_{11}$-thiophen-2-yl* | H |
| Compound 843 | S | S | Ph | H | 5-C$_6$H$_{13}$-thiophen-2-yl* | H |
| Compound 844 | S | S | Ph | H | 5-C$_7$H$_{15}$-thiophen-2-yl* | H |
| Compound 845 | S | S | Ph | H | 5-C$_8$H$_{17}$-thiophen-2-yl* | H |
| Compound 846 | S | S | Ph | H | 5-C$_9$H$_{19}$-thiophen-2-yl* | H |
| Compound 847 | S | S | Ph | H | 5-C$_{10}$H$_{21}$-thiophen-2-yl* | H |
| Compound 848 | S | S | Ph | H | 5-C$_{11}$H$_{23}$-thiophen-2-yl* | H |
| Compound 849 | S | S | Ph | H | 5-C$_{12}$H$_{25}$-thiophen-2-yl* | H |
| Compound 850 | S | S | Ph | H | 5-C$_{13}$H$_{27}$-thiophen-2-yl* | H |
| Compound 851 | S | S | Ph | H | 5-C$_{14}$H$_{29}$-thiophen-2-yl* | H |
| Compound 852 | S | S | Ph | H | 5-C$_{15}$H$_{31}$-thiophen-2-yl* | H |

TABLE 33

| | $X^{b1}$ | $X^{b2}$ | $R^{b11}$ | $R^{b12}$ | $R^{b21}$ | $R^{b22}$ |
|---|---|---|---|---|---|---|
| Compound 853 | S | S | Ph | H | 5-C$_{16}$H$_{33}$-thiophen-2-yl* | H |

TABLE 33-continued

| | $X^{b1}$ | $X^{b2}$ | $R^{b11}$ | $R^{b12}$ | $R^{b21}$ | $R^{b22}$ |
|---|---|---|---|---|---|---|
| Compound 854 | S | S | Ph | H | 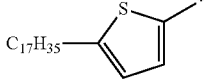 $C_{17}H_{35}$-thienyl* | H |
| Compound 855 | S | S | 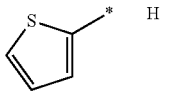 thienyl* | H | 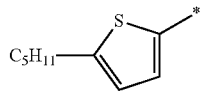 $C_5H_{11}$-thienyl* | H |
| Compound 856 | S | S | 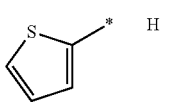 thienyl* | H | 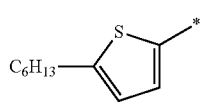 $C_6H_{13}$-thienyl* | H |
| Compound 857 | S | S | 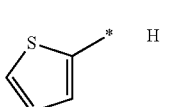 thienyl* | H | 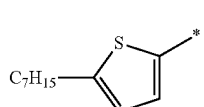 $C_7H_{15}$-thienyl* | H |
| Compound 858 | S | S | 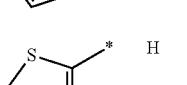 thienyl* | H | 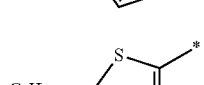 $C_8H_{17}$-thienyl* | H |
| Compound 859 | S | S | 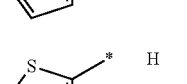 thienyl* | H | 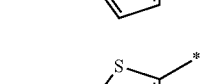 $C_9H_{19}$-thienyl* | H |
| Compound 860 | S | S | 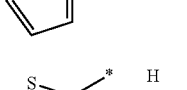 thienyl* | H | 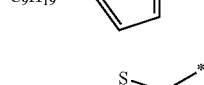 $C_{10}H_{21}$-thienyl* | H |
| Compound 861 | S | S | 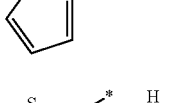 thienyl* | H | 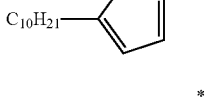 $C_{11}H_{23}$-thienyl* | H |
| Compound 862 | S | S |  thienyl* | H | 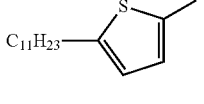 $C_{12}H_{25}$-thienyl* | H |
| Compound 863 | S | S | 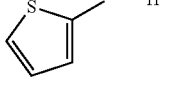 thienyl* | H | 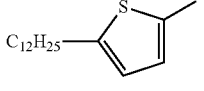 $C_{13}H_{27}$-thienyl* | H |
| Compound 864 | S | S | 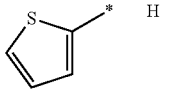 thienyl* | H | 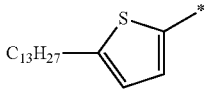 $C_{14}H_{29}$-thienyl* | H |
| Compound 865 | S | S | 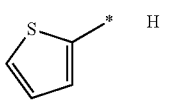 thienyl* | H | 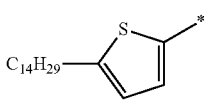 $C_{15}H_{31}$-thienyl* | H |
| Compound 866 | S | S | 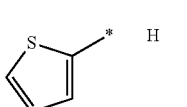 thienyl* | H | 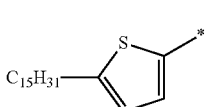 $C_{16}H_{33}$-thienyl* | H |
| Compound 867 | S | S | 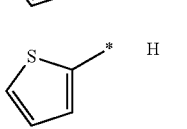 thienyl* | H | 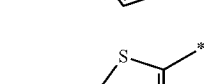 $C_{17}H_{35}$-thienyl* | H |

TABLE 33-continued
| | $X^{b1}$ | $X^{b2}$ | $R^{b11}$ | $R^{b12}$ | $R^{b21}$ | $R^{b22}$ |
|---|---|---|---|---|---|---|
| Compound 868 | S | S | H | H | H | 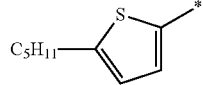 |
| Compound 869 | S | S | H | H | H | 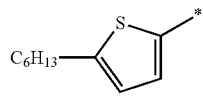 |
| Compound 870 | S | S | H | H | H | 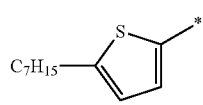 |
TABLE 34
| | $X^{b1}$ | $X^{b2}$ | $R^{b11}$ | $R^{b12}$ | $R^{b21}$ | $R^{b22}$ |
|---|---|---|---|---|---|---|
| Compound 871 | S | S | H | H | H | 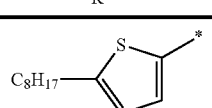 |
| Compound 872 | S | S | H | H | H | 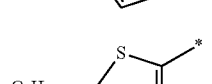 |
| Compound 873 | S | S | H | H | H | 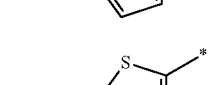 |
| Compound 874 | S | S | H | H | H | 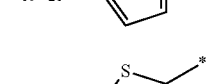 |
| Compound 875 | S | S | H | H | H | 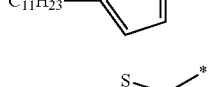 |
| Compound 876 | S | S | H | H | H | 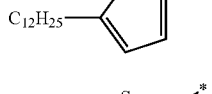 |
| Compound 877 | S | S | H | H | H | 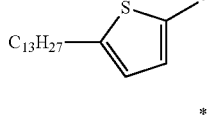 |
| Compound 878 | S | S | H | H | H | 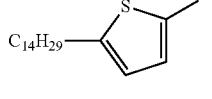 |
| Compound 879 | S | S | H | H | H | 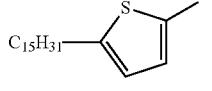 |
| Compound 880 | S | S | H | H | H | 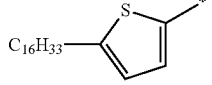 |

TABLE 34-continued

| | $X^{b1}$ | $X^{b2}$ | $R^{b11}$ | $R^{b12}$ | $R^{b21}$ | $R^{b22}$ |
|---|---|---|---|---|---|---|
| Compound 881 | S | S | H | H | 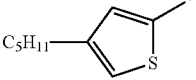 ($C_5H_{11}$-thiophene-*) | H |
| Compound 882 | S | S | H | H | 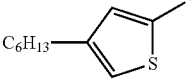 ($C_6H_{13}$-thiophene-*) | H |
| Compound 883 | S | S | H | H | 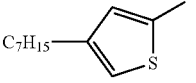 ($C_7H_{15}$-thiophene-*) | H |
| Compound 884 | S | S | H | H | 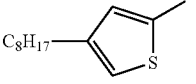 ($C_8H_{17}$-thiophene-*) | H |
| Compound 885 | S | S | H | H | 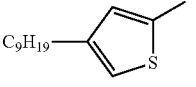 ($C_9H_{19}$-thiophene-*) | H |
| Compound 886 | S | S | H | H | 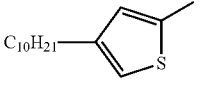 ($C_{10}H_{21}$-thiophene-*) | H |
| Compound 887 | S | S | H | H | 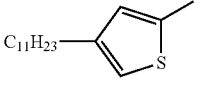 ($C_{11}H_{23}$-thiophene-*) | H |
| Compound 888 | S | S | H | H | 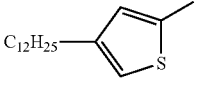 ($C_{12}H_{25}$-thiophene-*) | H |

TABLE 35

| | $X^{b1}$ | $X^{b2}$ | $R^{b11}$ | $R^{b12}$ | $R^{b21}$ | $R^{b22}$ |
|---|---|---|---|---|---|---|
| Compound 889 | S | S | H | H | 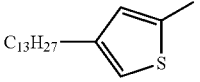 ($C_{13}H_{27}$-thiophene-*) | H |
| Compound 890 | S | S | H | H | 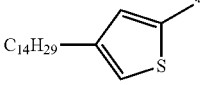 ($C_{14}H_{29}$-thiophene-*) | H |
| Compound 891 | S | S | H | H | 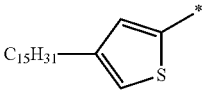 ($C_{15}H_{31}$-thiophene-*) | H |
| Compound 892 | S | S | H | H | 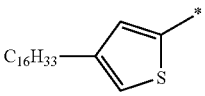 ($C_{16}H_{33}$-thiophene-*) | H |
| Compound 893 | S | S | H | H | 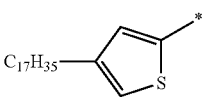 ($C_{17}H_{35}$-thiophene-*) | H |
| Compound 894 | S | S | H | H | 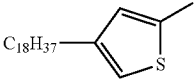 ($C_{18}H_{37}$-thiophene-*) | H |
| Compound 895 | S | S | Ph | H | 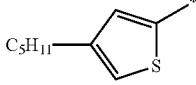 ($C_5H_{11}$-thiophene-*) | H |
| Compound 896 | S | S | Ph | H | 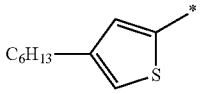 ($C_6H_{13}$-thiophene-*) | H |
| Compound 897 | S | S | Ph | H | 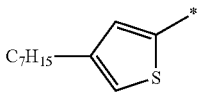 ($C_7H_{15}$-thiophene-*) | H |
| Compound 898 | S | S | Ph | H | 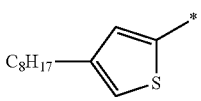 ($C_8H_{17}$-thiophene-*) | H |

TABLE 35-continued

| | $X^{b1}$ | $X^{b2}$ | $R^{b11}$ | $R^{b12}$ | $R^{b21}$ | $R^{b22}$ |
|---|---|---|---|---|---|---|
| Compound 899 | S | S | Ph | H | 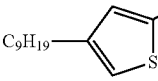 C$_9$H$_{19}$-thienyl-* | H |
| Compound 900 | S | S | Ph | H | 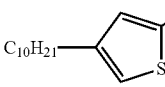 C$_{10}$H$_{21}$-thienyl-* | H |
| Compound 901 | S | S | Ph | H | 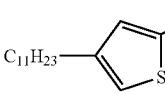 C$_{11}$H$_{23}$-thienyl-* | H |
| Compound 902 | S | S | Ph | H | 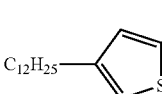 C$_{12}$H$_{25}$-thienyl-* | H |
| Compound 903 | S | S | Ph | H | 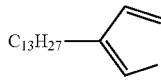 C$_{13}$H$_{27}$-thienyl-* | H |
| Compound 904 | S | S | Ph | H | 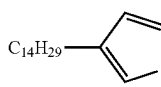 C$_{14}$H$_{29}$-thienyl-* | H |
| Compound 905 | S | S | Ph | H | 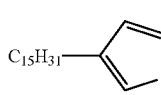 C$_{15}$H$_{31}$-thienyl-* | H |
| Compound 906 | S | S | Ph | H | 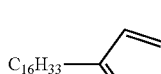 C$_{16}$H$_{33}$-thienyl-* | H |

TABLE 36

| | $X^{b1}$ | $X^{b2}$ | $R^{b11}$ | $R^{b12}$ | $R^{b21}$ | $R^{b22}$ |
|---|---|---|---|---|---|---|
| Compound 907 | S | S | Ph | H | 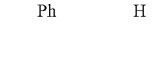 C$_{17}$H$_{35}$-thienyl-* | H |
| Compound 908 | S | S | Ph | H | 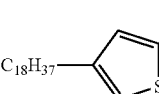 C$_{18}$H$_{37}$-thienyl-* | H |
| Compound 909 | S | S | 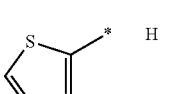 thienyl-* | H |  C$_5$H$_{11}$-thienyl-* | H |
| Compound 910 | S | S | 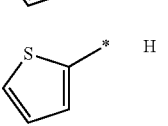 thienyl-* | H |  C$_6$H$_{13}$-thienyl-* | H |
| Compound 911 | S | S |  thienyl-* | H | 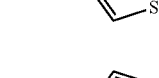 C$_7$H$_{15}$-thienyl-* | H |
| Compound 912 | S | S |  thienyl-* | H | 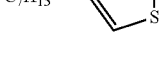 C$_8$H$_{17}$-thienyl-* | H |
| Compound 913 | S | S |  thienyl-* | H | 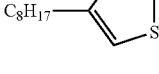 C$_9$H$_{19}$-thienyl-* | H |
| Compound 914 | S | S |  thienyl-* | H | 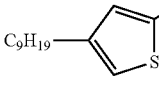 C$_{10}$H$_{21}$-thienyl-* | H |
| Compound 915 | S | S | 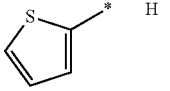 thienyl-* | H | 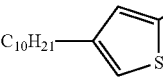 C$_{11}$H$_{23}$-thienyl-* | H |

TABLE 36-continued

| | $X^{b1}$ | $X^{b2}$ | $R^{b11}$ | $R^{b12}$ | $R^{b21}$ | $R^{b22}$ |
|---|---|---|---|---|---|---|
| Compound 916 | S | S |  | H | 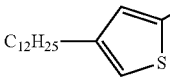 C$_{12}$H$_{25}$— | H |
| Compound 917 | S | S |  | H | 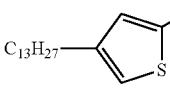 C$_{13}$H$_{27}$— | H |
| Compound 918 | S | S |  | H | 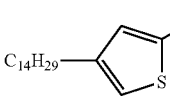 C$_{14}$H$_{29}$— | H |
| Compound 919 | S | S |  | H | 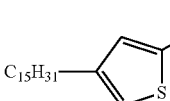 C$_{15}$H$_{31}$— | H |
| Compound 920 | S | S |  | H |  C$_{16}$H$_{33}$— | H |
| Compound 921 | S | S |  | H |  C$_{17}$H$_{35}$— | H |
| Compound 922 | S | S |  | H | 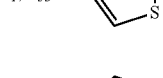 C$_{18}$H$_{37}$— | H |
| Compound 923 | S | S | C$_{10}$H$_{21}$—* | H | p-C$_5$H$_{11}$—Ph—* | H |
| Compound 924 | S | S | C$_{10}$H$_{21}$—* | H | p-C$_6$H$_{13}$—Ph—* | H |
| Compound 925 | S | S | C$_{10}$H$_{21}$—* | H | p-C$_7$H$_{15}$—Ph—* | H |
| Compound 926 | S | S | C$_{10}$H$_{21}$—* | H | p-C$_8$H$_{17}$—Ph—* | H |
| Compound 927 | S | S | C$_{10}$H$_{21}$—* | H | p-C$_9$H$_{19}$—Ph—* | H |
| Compound 928 | S | S | C$_{10}$H$_{21}$—* | H | p-C$_{10}$H$_{21}$—Ph—* | H |
| Compound 929 | S | S | C$_{10}$H$_{21}$—* | H | p-C$_{11}$H$_{23}$—Ph—* | H |
| Compound 930 | S | S | C$_{10}$H$_{21}$—* | H | p-C$_{12}$H$_{25}$—Ph—* | H |

| TABLE 37 | $X^{b1}$ | $X^{b2}$ | $R^{b11}$ | $R^{b12}$ | $R^{b21}$ | $R^{b22}$ |
|---|---|---|---|---|---|---|
| Compound 931 | S | S | C$_{10}$H$_{21}$—* | H | p-C$_{13}$H$_{27}$—Ph—* | H |
| Compound 932 | S | S | C$_{10}$H$_{21}$—* | H | p-C$_{14}$H$_{29}$—Ph—* | H |
| Compound 933 | S | S | C$_{10}$H$_{21}$—* | H | p-C$_{15}$H$_{31}$—Ph—* | H |
| Compound 934 | S | S | C$_{10}$H$_{21}$—* | H | p-C$_{16}$H$_{33}$—Ph—* | H |
| Compound 935 | S | S | C$_{10}$H$_{21}$—* | H | p-C$_{17}$H$_{35}$—Ph—* | H |
| Compound 936 | S | S | C$_{10}$H$_{21}$—* | H | p-C$_{18}$H$_{37}$—Ph—* | H |
| Compound 937 | S | S | C$_{12}$H$_{25}$—* | H | 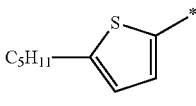 C$_5$H$_{11}$— | H |
| Compound 938 | S | S | C$_{12}$H$_{25}$—* | H | 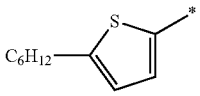 C$_6$H$_{12}$— | H |

TABLE 37-continued

| | $X^{b1}$ | $X^{b2}$ | $R^{b11}$ | $R^{b12}$ | $R^{b21}$ | $R^{b22}$ |
|---|---|---|---|---|---|---|
| Compound 939 | S | S | $C_{12}H_{25}$—* | H | 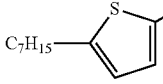 | H |
| Compound 940 | S | S | $C_{12}H_{25}$—* | H | 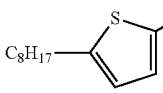 | H |
| Compound 941 | S | S | $C_{12}H_{25}$—* | H | 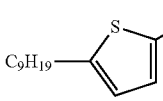 | H |
| Compound 942 | S | S | $C_{12}H_{25}$—* | H | 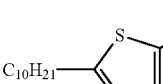 | H |
| Compound 943 | S | S | $C_{12}H_{25}$—* | H | 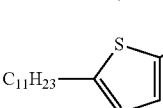 | H |
| Compound 944 | S | S | $C_{12}H_{25}$—* | H | 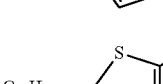 | H |
| Compound 945 | S | S | $C_{12}H_{25}$-* | H | 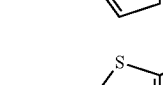 | H |
| Compound 946 | S | S | $C_{12}H_{25}$—* | H | 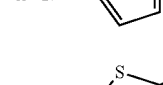 | H |
| Compound 947 | S | S | $C_{12}H_{25}$—* | H | 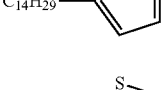 | H |
| Compound 948 | S | S | $C_{12}H_{25}$—* | H | 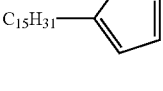 | H |
| Compound 949 | S | S | $C_{12}H_{25}$—* | H | 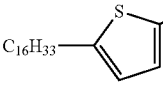 | H |
| Compound 950 | S | S | $C_{12}H_{25}$—* | H | 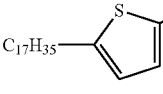 | H |
| Compound 951 | S | S | $C_5H_{11}$—* | H | H | $C_{12}H_{25}$—* |
| Compound 952 | S | S | $C_6H_{13}$—* | H | H | $C_{12}H_{25}$—* |
| Compound 953 | S | S | $C_7H_{15}$—* | H | H | $C_{12}H_{25}$—* |
| Compound 954 | S | S | $C_8H_{17}$—* | H | H | $C_{12}H_{25}$—* |
| Compound 955 | S | S | $C_9H_{19}$—* | H | H | $C_{12}H_{25}$—* |
| Compound 956 | S | S | $C_{10}H_{21}$—* | H | H | $C_{12}H_{25}$—* |

-continued

TABLE 37

| | $X^{b1}$ | $X^{b2}$ | $R^{b11}$ | $R^{b12}$ | $R^{b21}$ | $R^{b22}$ |
|---|---|---|---|---|---|---|
| Compound 957 | S | S | $C_{11}H_{23}$—* | H | H | $C_{12}H_{25}$—* |
| Compound 958 | S | S | $C_{12}H_{25}$—* | H | H | $C_{12}H_{25}$—* |

TABLE 38

| | $X^{b1}$ | $X^{b2}$ | $R^{b11}$ | $R^{b12}$ | $R^{b21}$ | $R^{b22}$ |
|---|---|---|---|---|---|---|
| Compound 959 | S | S | $C_{13}H_{27}$—* | H | H | $C_{12}H_{25}$—* |
| Compound 960 | S | S | $C_{14}H_{29}$—* | H | H | $C_{12}H_{25}$—* |
| Compound 961 | S | S | $C_{15}H_{31}$—* | H | H | $C_{12}H_{25}$—* |
| Compound 962 | S | S | $C_{16}H_{33}$—* | H | H | $C_{12}H_{25}$—* |
| Compound 963 | S | S | $C_{17}H_{35}$—* | H | H | $C_{12}H_{25}$—* |
| Compound 964 | S | S | $C_{18}H_{37}$—* | H | H | $C_{12}H_{25}$—* |
| Compound 965 | S | S | $C_{10}H_{21}$—* | H | H | p-$C_5H_{11}$—Ph—* |
| Compound 966 | S | S | $C_{10}H_{21}$—* | H | H | p-$C_6H_{13}$—Ph—* |
| Compound 967 | S | S | $C_{10}H_{21}$—* | H | H | p-$C_7H_{15}$—Ph—* |
| Compound 968 | S | S | $C_{10}H_{21}$—* | H | H | p-$C_8H_{17}$—Ph—* |
| Compound 969 | S | S | $C_{10}H_{21}$—* | H | H | p-$C_9H_{19}$—Ph—* |
| Compound 970 | S | S | $C_{10}H_{21}$—* | H | H | p-$C_{10}H_{21}$—Ph—* |
| Compound 971 | S | S | $C_{10}H_{21}$—* | H | H | p-$C_{11}H_{23}$—Ph—* |
| Compound 972 | S | S | $C_{10}H_{21}$—* | H | H | p-$C_{12}H_{25}$—Ph—* |
| Compound 973 | S | S | $C_{10}H_{21}$—* | H | H | p-$C_{13}H_{27}$—Ph—* |
| Compound 974 | S | S | $C_{10}H_{21}$—* | H | H | p-$C_{14}H_{29}$—Ph—* |
| Compound 975 | S | S | $C_{10}H_{21}$—* | H | H | p-$C_{15}H_{31}$—Ph—* |
| Compound 976 | S | S | $C_{10}H_{21}$—* | H | H | p-$C_{16}H_{33}$—Ph—* |
| Compound 977 | S | S | $C_{10}H_{21}$—* | H | H | p-$C_{17}H_{35}$—Ph—* |
| Compound 978 | S | S | $C_{10}H_{21}$—* | H | H | p-$C_{18}H_{37}$—Ph—* |
| Compound 979 | S | S | H | $C_{10}H_{21}$—* | H | p-$C_5H_{11}$—Ph—* |
| Compound 980 | S | S | H | $C_{10}H_{21}$—* | H | p-$C_6H_{13}$—Ph—* |
| Compound 981 | S | S | H | $C_{10}H_{21}$—* | H | p-$C_7H_{15}$—Ph—* |
| Compound 982 | S | S | H | $C_{10}H_{21}$—* | H | p-$C_8H_{17}$—Ph—* |
| Compound 983 | S | S | H | $C_{10}H_{21}$—* | H | p-$C_9H_{19}$—Ph—* |
| Compound 984 | S | S | H | $C_{10}H_{21}$—* | H | p-$C_{10}H_{21}$—Ph—* |
| Compound 985 | S | S | H | $C_{10}H_{21}$—* | H | p-$C_{11}H_{23}$—Ph—* |
| Compound 986 | S | S | H | $C_{10}H_{21}$—* | H | p-$C_{12}H_{25}$—Ph—* |
| Compound 987 | S | S | H | $C_{10}H_{21}$—* | H | p-$C_{13}H_{27}$—Ph—* |
| Compound 988 | S | S | H | $C_{10}H_{21}$—* | H | p-$C_{14}H_{29}$—Ph—* |
| Compound 989 | S | S | H | $C_{10}H_{21}$—* | H | p-$C_{15}H_{31}$—Ph—* |
| Compound 990 | S | S | H | $C_{10}H_{21}$—* | H | p-$C_{16}H_{33}$—Ph—* |
| Compound 991 | S | S | H | $C_{10}H_{21}$—* | H | p-$C_{17}H_{35}$—Ph—* |
| Compound 992 | S | S | H | $C_{10}H_{21}$—* | H | p-$C_{18}H_{37}$—Ph—* |
| Compound 993 | S | S | 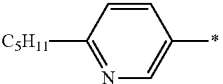 | H | 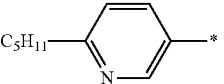 | H |
| Compound 994 | S | S | 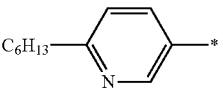 | H | 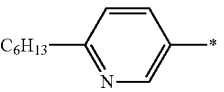 | H |
| Compound 995 | S | S | 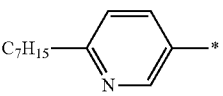 | H | 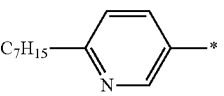 | H |
| Compound 996 | S | S | 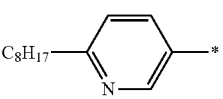 | H | 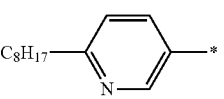 | H |
| Compound 997 | S | S | 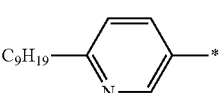 | H | 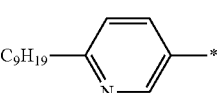 | H |
| Compound 998 | S | S | 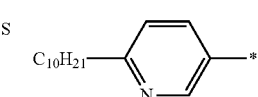 | H | 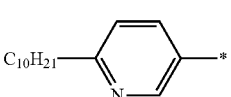 | H |

TABLE 39
| | $X^{b1}$ | $X^{b2}$ | $R^{b11}$ | $R^{b12}$ | $R^{b21}$ | $R^{b22}$ |
|---|---|---|---|---|---|---|
| Compound 999 | S | S | 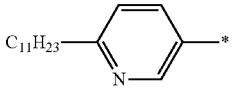 | H | 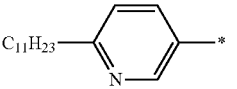 | H |
| Compound 1000 | S | S | 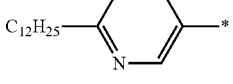 | H | 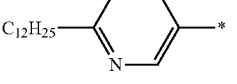 | H |
| Compound 1001 | S | S | 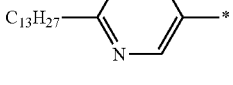 | H | 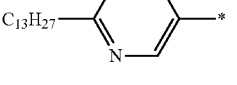 | H |
| Compound 1002 | S | S | 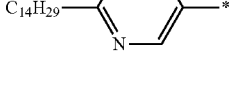 | H | 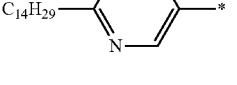 | H |
| Compound 1003 | S | S | 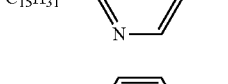 | H | 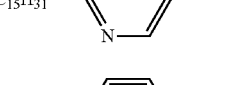 | H |
| Compound 1004 | S | S | 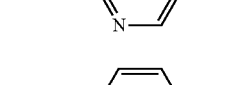 | H | 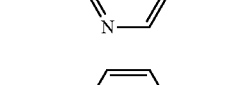 | H |
| Compound 1005 | S | S | 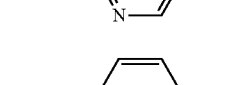 | H | 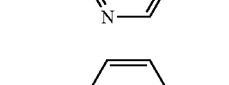 | H |
| Compound 1006 | S | S | 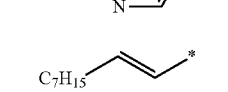 | H | 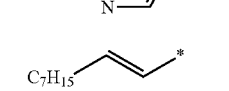 | H |
| Compound 1007 | S | S | 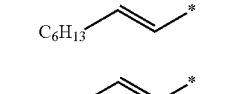 | H | 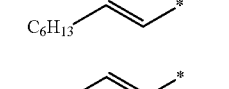 | H |
| Compound 1008 | S | S | 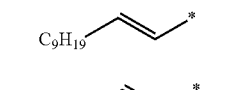 | H | 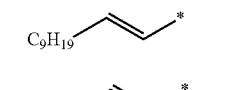 | H |
| Compound 1009 | S | S | 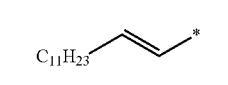 | H | 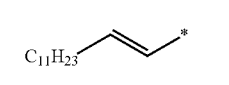 | H |
| Compound 1010 | S | S | 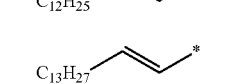 | H | 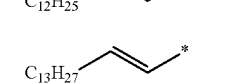 | H |
| Compound 1011 | S | S | 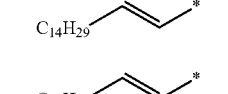 | H | 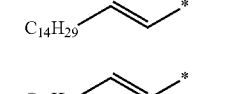 | H |
| Compound 1012 | S | S |  | H |  | H |
| Compound 1013 | S | S |  | H |  | H |
| Compound 1014 | S | S | $C_{13}H_{27}$ | H | $C_{13}H_{27}$ | H |
| Compound 1015 | S | S | $C_{14}H_{29}$ | H | $C_{14}H_{29}$ | H |
| Compound 1016 | S | S | $C_{15}H_{31}$ | H | $C_{15}H_{31}$ | H |

TABLE 40

| | $X^{b1}$ | $X^{b2}$ | $R^{b11}$ | $R^{b12}$ | $R^{b21}$ | $R^{b22}$ |
|---|---|---|---|---|---|---|
| Compound 1017 | S | S | 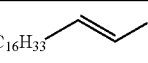 C$_{16}$H$_{33}$—CH=CH—* | H | 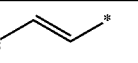 C$_{16}$H$_{33}$—CH=CH—* | H |
| Compound 1018 | S | S | C$_{17}$H$_{35}$—CH=CH—* | H | C$_{17}$H$_{35}$—CH=CH—* | H |
| Compound 1019 | S | S | C$_{18}$H$_{37}$—CH=CH—* | H | C$_{18}$H$_{37}$—CH=CH—* | H |
| Compound 1020 | S | S | C$_5$H$_{11}$—C≡C—* | H | C$_5$H$_{11}$—C≡C—* | H |
| Compound 1021 | S | S | C$_6$H$_{13}$—C≡C—* | H | C$_6$H$_{13}$—C≡C—* | H |
| Compound 1022 | S | S | C$_7$H$_{15}$—C≡C—* | H | C$_7$H$_{15}$—C≡C—* | H |
| Compound 1023 | S | S | C$_8$H$_{17}$—C≡C—* | H | C$_8$H$_{17}$—C≡C—* | H |
| Compound 1024 | S | S | C$_9$H$_{19}$—C≡C—* | H | C$_9$H$_{19}$—C≡C—* | H |
| Compound 1025 | S | S | C$_{10}$H$_{21}$—C≡C—* | H | C$_{10}$H$_{21}$—C≡C—* | H |
| Compound 1026 | S | S | C$_{11}$H$_{23}$—C≡C—* | H | C$_{11}$H$_{23}$—C≡C—* | H |
| Compound 1027 | S | S | C$_{12}$H$_{25}$—C≡C—* | H | C$_{12}$H$_{25}$—C≡C—* | H |
| Compound 1028 | S | S | C$_{13}$H$_{27}$—C≡C—* | H | C$_{13}$H$_{27}$—C≡C—* | H |
| Compound 1029 | S | S | C$_{14}$H$_{29}$—C≡C—* | H | C$_{14}$H$_{29}$—C≡C—* | H |
| Compound 1030 | S | S | C$_{15}$H$_{31}$—C≡C—* | H | C$_{15}$H$_{31}$—C≡C—* | H |
| Compound 1031 | S | S | C$_{16}$H$_{33}$—C≡C—* | H | C$_{16}$H$_{33}$—C≡C—* | H |
| Compound 1032 | S | S | C$_{17}$H$_{35}$—C≡C—* | H | C$_{17}$H$_{35}$—C≡C—* | H |

TABLE 40-continued

| | $X^{b1}$ | $X^{b2}$ | $R^{b11}$ | $R^{b12}$ | $R^{b21}$ | $R^{b22}$ |
|---|---|---|---|---|---|---|
| Compound 1033 | S | S | C$_{18}$H$_{37}$—C≡C—* | H | C$_{18}$H$_{37}$—C≡C—* | H |
| Compound 1034 | O | O | C$_5$H$_{11}$—* | H | C$_5$H$_{11}$—* | H |
| Compound 1035 | O | O | C$_6$H$_{13}$—* | H | C$_6$H$_{13}$—* | H |
| Compound 1036 | O | O | C$_7$H$_{15}$—* | H | C$_7$H$_{15}$—* | H |
| Compound 1037 | O | O | C$_8$H$_{17}$—* | H | C$_8$H$_{17}$—* | H |
| Compound 1038 | O | O | C$_9$H$_{19}$—* | H | C$_9$H$_{19}$—* | H |

TABLE 41

| | $X^{b1}$ | $X^{b2}$ | $R^{b11}$ | $R^{b12}$ | $R^{b21}$ | $R^{b22}$ |
|---|---|---|---|---|---|---|
| Compound 1039 | O | O | C$_{10}$H$_{21}$—* | H | C$_{10}$H$_{21}$—* | H |
| Compound 1040 | O | O | C$_{11}$H$_{23}$—* | H | C$_{11}$H$_{23}$—* | H |
| Compound 1041 | O | O | C$_{12}$H$_{25}$—* | H | C$_{12}$H$_{25}$—* | H |
| Compound 1042 | O | O | C$_{13}$H$_{27}$—* | H | C$_{13}$H$_{27}$—* | H |
| Compound 1043 | O | O | C$_{14}$H$_{29}$—* | H | C$_{14}$H$_{29}$—* | H |
| Compound 1044 | O | O | C$_{15}$H$_{31}$—* | H | C$_{15}$H$_{31}$—* | H |
| Compound 1045 | O | O | C$_{16}$H$_{33}$—* | H | C$_{16}$H$_{33}$—* | H |
| Compound 1046 | O | O | C$_{17}$H$_{35}$—* | H | C$_{17}$H$_{35}$—* | H |
| Compound 1047 | O | O | C$_{18}$H$_{37}$—* | H | C$_{18}$H$_{37}$—* | H |
| Compound 1048 | O | O | p-C$_5$H$_{11}$—Ph—* | H | p-C$_5$H$_{11}$—Ph—* | H |
| Compound 1049 | O | O | p-C$_6$H$_{13}$—Ph—* | H | p-C$_6$H$_{13}$—Ph—* | H |
| Compound 1050 | O | O | p-C$_7$H$_{15}$—Ph—* | H | p-C$_7$H$_{15}$—Ph—* | H |
| Compound 1051 | O | O | p-C$_8$H$_{17}$—Ph—* | H | p-C$_8$H$_{17}$—Ph—* | H |
| Compound 1052 | O | O | p-C$_9$H$_{19}$—Ph—* | H | p-C$_9$H$_{19}$—Ph—* | H |
| Compound 1053 | O | O | p-C$_{10}$H$_{21}$—Ph—* | H | p-C$_{10}$H$_{21}$—Ph—* | H |
| Compound 1054 | O | O | p-C$_{11}$H$_{23}$—Ph—* | H | p-C$_{11}$H$_{23}$—Ph—* | H |
| Compound 1055 | O | O | p-C$_{12}$H$_{25}$—Ph—* | H | p-C$_{12}$H$_{25}$—Ph—* | H |
| Compound 1056 | O | O | p-C$_{13}$H$_{27}$—Ph—* | H | p-C$_{13}$H$_{27}$—Ph—* | H |
| Compound 1057 | O | O | p-C$_{14}$H$_{29}$—Ph—* | H | p-C$_{14}$H$_{29}$—Ph—* | H |
| Compound 1058 | O | O | p-C$_{15}$H$_{31}$—Ph—* | H | p-C$_{15}$H$_{31}$—Ph—* | H |
| Compound 1059 | O | O | p-C$_{16}$H$_{33}$—Ph—* | H | p-C$_{16}$H$_{33}$—Ph—* | H |
| Compound 1060 | O | O | p-C$_{17}$H$_{35}$—Ph—* | H | p-C$_{17}$H$_{35}$—Ph—* | H |
| Compound 1061 | O | O | p-C$_{18}$H$_{37}$—Ph—* | H | p-C$_{18}$H$_{37}$—Ph—* | H |
| Compound 1062 | O | O | C$_5$H$_{11}$-(thiophen-2,5-diyl)—* | H | C$_5$H$_{11}$-(thiophen-2,5-diyl)—* | H |
| Compound 1063 | O | O | C$_6$H$_{13}$-(thiophen-2,5-diyl)—* | H | C$_6$H$_{13}$-(thiophen-2,5-diyl)—* | H |
| Compound 1064 | O | O | C$_7$H$_{15}$-(thiophen-2,5-diyl)—* | H | C$_7$H$_{15}$-(thiophen-2,5-diyl)—* | H |
| Compound 1065 | O | O | C$_8$H$_{17}$-(thiophen-2,5-diyl)—* | H | C$_8$H$_{17}$-(thiophen-2,5-diyl)—* | H |
| Compound 1066 | O | O | C$_9$H$_{19}$-(thiophen-2,5-diyl)—* | H | C$_9$H$_{19}$-(thiophen-2,5-diyl)—* | H |
| Compound 1067 | O | O | C$_{10}$H$_{21}$-(thiophen-2,5-diyl)—* | H | C$_{10}$H$_{21}$-(thiophen-2,5-diyl)—* | H |

TABLE 41-continued

| | $X^{b1}$ | $X^{b2}$ | $R^{b11}$ | $R^{b12}$ | $R^{b21}$ | $R^{b22}$ |
|---|---|---|---|---|---|---|
| Compound 1068 | O | O | 5-C₁₁H₂₃-thiophen-2-yl* | H | 5-C₁₁H₂₃-thiophen-2-yl* | H |
| Compound 1069 | O | O | 5-C₁₂H₂₅-thiophen-2-yl* | H | 5-C₁₂H₂₅-thiophen-2-yl* | H |
| Compound 1070 | O | O | 5-C₁₃H₂₇-thiophen-2-yl* | H | 5-C₁₃H₂₇-thiophen-2-yl* | H |
| Compound 1071 | O | O | 5-C₁₄H₂₉-thiophen-2-yl* | H | 5-C₁₄H₂₉-thiophen-2-yl* | H |

TABLE 42

| | $X^{b1}$ | $X^{b2}$ | $R^{b11}$ | $R^{b12}$ | $R^{b21}$ | $R^{b22}$ |
|---|---|---|---|---|---|---|
| Compound 1072 | O | O | 5-C₁₅H₃₁-thiophen-2-yl* | H | 5-C₁₅H₃₁-thiophen-2-yl* | H |
| Compound 1073 | O | O | 5-C₁₆H₃₃-thiophen-2-yl* | H | 5-C₁₆H₃₃-thiophen-2-yl* | H |
| Compound 1074 | O | O | 5-C₁₇H₃₅-thiophen-2-yl* | H | 5-C₁₇H₃₅-thiophen-2-yl* | H |
| Compound 1075 | O | O | 5-C₁₈H₃₇-thiophen-2-yl* | H | 5-C₁₈H₃₇-thiophen-2-yl* | H |
| Compound 1076 | S | S | C₄H₃OC₄H₈—* | H | C₄H₃OC₄H₈—* | H |
| Compound 1077 | S | S | C₂H₅OC₂H₄—* | H | C₂H₅OC₂H₄—* | H |
| Compound 1078 | S | S | C₆H₁₃OC₄H₈—* | H | C₆H₁₃OC₄H₈—* | H |
| Compound 1079 | S | S | C₂H₅OC₄H₈—* | H | C₂H₅OC₄H₈—* | H |
| Compound 1080 | S | S | CH₃OC₃H₅—* | H | CH₃OC₃H₅—* | H |
| Compound 1081 | S | S | 4-(C₄H₉—O—(C₄H₈)—)phenyl* | H | 4-(C₄H₉—O—(C₄H₈)—)phenyl* | H |
| Compound 1082 | S | S | 5-(C₄H₉—O—(C₄H₈)—)thiophen-2-yl* | H | 5-(C₄H₉—O—(C₄H₈)—)thiophen-2-yl* | H |
| Compound 1083 | S | S | 4-(C₄H₉—O—(C₄H₈)—)thiophen-2-yl* | H | 4-(C₄H₉—O—(C₄H₈)—)thiophen-2-yl* | H |
| Compound 1084 | S | S | PhO₃H₆—* | H | PhO₃H₆—* | H |
| Compound 1085 | S | S | PhOC₃H₆—* | H | PhOC₃H₆—* | H |

TABLE 42-continued

| | $X^{b1}$ | $X^{b2}$ | $R^{b11}$ | $R^{b12}$ | $R^{b21}$ | $R^{b22}$ |
|---|---|---|---|---|---|---|
| Compound 1086 | S | S | 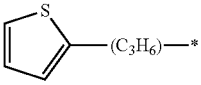 | H | 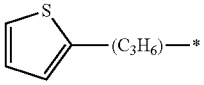 | H |
| Compound 1087 | S | S | 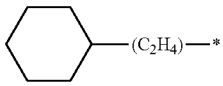 | H | 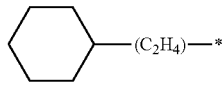 | H |
| Compound 1088 | S | S | 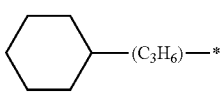 | H | 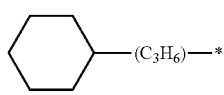 | H |
| Compound 1089 | S | S | 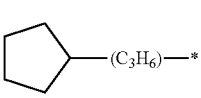 | H | 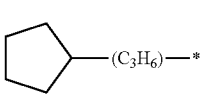 | H |
| Compound 1090 | S | S | 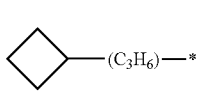 | H | 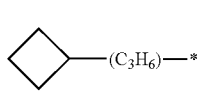 | H |
| Compound 1091 | S | S | 3,7-Dimethyloctyl | H | 3,7-Dimethyloctyl | H |
| Compound 1092 | S | S | 3,7-Dimethyloctyl | H | H | H |
| Compound 1093 | S | S | 2-Ethylhexyl | H | 2-Ethylhexyl | H |
| Compound 1094 | S | S | 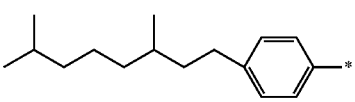 [SMILES: *c1ccc(CCC(C)CCCC(C)C)cc1] | H | 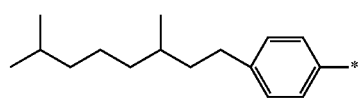 [SMILES: *c1ccc(CCC(C)CCCC(C)C)cc1] | H |
| Compound 1095 | S | S | 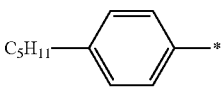 | H | 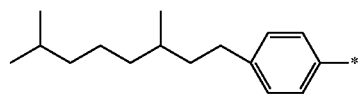 [SMILES: *c1ccc(CCC(C)CCCC(C)C)cc1] | H |

TABLE 43

| | $X^{b1}$ | $X^{b2}$ | $R^{b11}$ | $R^{b12}$ | $R^{b21}$ | $R^{b22}$ |
|---|---|---|---|---|---|---|
| Compound 1096 | S | S | 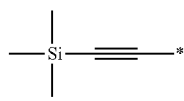 [SMILES: *C#C[Si](C)(C)C] | H | 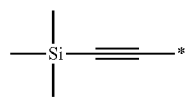 | H |
| Compound 1097 | S | S | 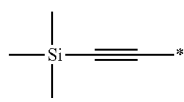 [SMILES: *C#C[Si](C)(C)C] | H | H | H |
| Compound 1098 | S | S | 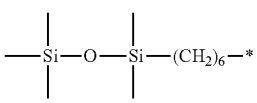 | H | 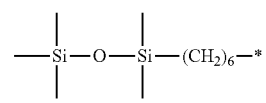 | H |
| Compound 1099 | S | S | $C_5H_{11}$—* | H | 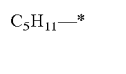 | H |
| Compound 1100 | S | S | 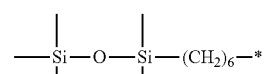 | H | 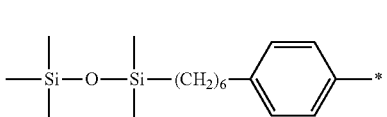 | H |
| Compound 1101 | S | S | 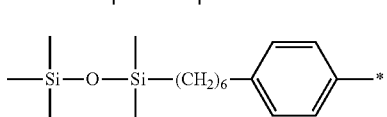 | H | 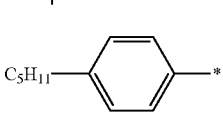 | H |

TABLE 43-continued

| | $X^{b1}$ | $X^{b2}$ | $R^{b11}$ | $R^{b12}$ | $R^{b21}$ | $R^{b22}$ |
|---|---|---|---|---|---|---|
| Compound 1102 | S | S | $C_8H_{17}$–C≡C–C₆H₄–* | H | $C_8H_{17}$–C≡C–C₆H₄–* | H |
| Compound 1103 | S | S | $C_8H_{17}$–CH=CH–C₆H₄–* | H | $C_8H_{17}$–CH=CH–C₆H₄–* | H |
| Compound 1104 | S | S | CH₂=CH–(CH₂)₆–* | H | CH₂=CH–(CH₂)₆–* | H |
| Compound 1105 | S | S | CH₂=CH–(CH₂)₆–* | H | H | H |
| Compound 1106 | S | S | CH₃–CH=CH–(CH₂)₂–* | H | CH₃–CH=CH–(CH₂)₂–* | H |
| Compound 1107 | S | S | CH₃–CH₂–CH=CH–(CH₂)₂–* (cis) | H | CH₃–CH₂–CH=CH–(CH₂)₂–* (cis) | H |
| Compound 1108 | S | S | CH₂=CH–(CH₂)₅–C₆H₄–* | H | CH₂=CH–(CH₂)₅–C₆H₄–* | H |
| Compound 1109 | S | S | $C_8H_{17}$–C₆H₄–* | H | CH₂=CH–(CH₂)₅–C₆H₄–* | H |

TABLE 44

| | $X^{c1}$ | $X^{c2}$ | $R^{c11}$ | $R^{c21}$ |
|---|---|---|---|---|
| Compound 1110 | S | S | $C_5H_{11}$—* | $C_5H_{11}$—* |
| Compound 1111 | S | S | $C_6H_{13}$—* | $C_6H_{13}$—* |
| Compound 1112 | S | S | $C_7H_{15}$—* | $C_7H_{15}$—* |
| Compound 1113 | S | S | $C_8H_{17}$—* | $C_8H_{17}$—* |
| Compound 1114 | S | S | $C_9H_{19}$—* | $C_9H_{19}$—* |
| Compound 1115 | S | S | $C_{10}H_{21}$—* | $C_{10}H_{21}$—* |
| Compound 1116 | S | S | $C_{11}H_{23}$—* | $C_{11}H_{23}$—* |
| Compound 1117 | S | S | $C_{12}H_{25}$—* | $C_{12}H_{25}$—* |
| Compound 1118 | S | S | $C_{13}H_{27}$—* | $C_{13}H_{27}$—* |
| Compound 1119 | S | S | $C_{14}H_{29}$—* | $C_{14}H_{29}$—* |
| Compound 1120 | S | S | $C_{15}H_{31}$—* | $C_{15}H_{31}$—* |
| Compound 1121 | S | S | $C_{16}H_{33}$—* | $C_{16}H_{33}$—* |
| Compound 1122 | S | S | $C_{17}H_{35}$—* | $C_{17}H_{35}$—* |
| Compound 1123 | S | S | $C_{18}H_{37}$—* | $C_{18}H_{37}$—* |
| Compound 1124 | S | S | p-$C_5H_{11}$—Ph—* | p-$C_5H_{11}$—Ph—* |
| Compound 1125 | S | S | p-$C_6H_{13}$—Ph—* | p-$C_6H_{13}$—Ph—* |
| Compound 1126 | S | S | p-$C_7H_{15}$—Ph—* | p-$C_7H_{15}$—Ph—* |
| Compound 1127 | S | S | p-$C_8H_{17}$—Ph—* | p-$C_8H_{17}$—Ph—* |
| Compound 1128 | S | S | p-$C_9H_{19}$—Ph—* | p-$C_9H_{19}$—Ph—* |
| Compound 1129 | S | S | p-$C_{10}H_{21}$—Ph—* | p-$C_{10}H_{21}$—Ph—* |
| Compound 1130 | S | S | p-$C_{11}H_{23}$—Ph—* | p-$C_{11}H_{23}$—Ph—* |
| Compound 1131 | S | S | p-$C_{12}H_{25}$—Ph—* | p-$C_{12}H_{25}$—Ph—* |
| Compound 1132 | S | S | p-$C_{13}H_{27}$—Ph—* | p-$C_{13}H_{27}$—Ph—* |
| Compound 1133 | S | S | p-$C_{14}H_{29}$—Ph—* | p-$C_{14}H_{29}$—Ph—* |
| Compound 1134 | S | S | p-$C_{15}H_{31}$—Ph—* | p-$C_{15}H_{31}$—Ph—* |
| Compound 1135 | S | S | p-$C_{16}H_{33}$—Ph—* | p-$C_{16}H_{33}$—Ph—* |
| Compound 1136 | S | S | p-$C_{17}H_{35}$—Ph—* | p-$C_{17}H_{35}$—Ph—* |
| Compound 1137 | S | S | p-$C_{18}H_{37}$—Ph—* | p-$C_{18}H_{37}$—Ph—* |
| Compound 1138 | S | S | 5-$C_5H_{11}$-thien-2-yl—* | 5-$C_5H_{11}$-thien-2-yl—* |
| Compound 1139 | S | S | 5-$C_6H_{13}$-thien-2-yl—* | 5-$C_6H_{13}$-thien-2-yl—* |
| Compound 1140 | S | S | 5-$C_7H_{15}$-thien-2-yl—* | 5-$C_7H_{15}$-thien-2-yl—* |

TABLE 44-continued

| | $X^{c1}$ | $X^{c2}$ | $R^{c11}$ | $R^{c21}$ |
|---|---|---|---|---|
| Compound 1141 | S | S | C8H17-thiophen-2-yl | C8H17-thiophen-2-yl |
| Compound 1142 | S | S | C9H19-thiophen-2-yl | C9H19-thiophen-2-yl |
| Compound 1143 | S | S | C10H21-thiophen-2-yl | C10H21-thiophen-2-yl |
| Compound 1144 | S | S | C11H23-thiophen-2-yl | C11H23-thiophen-2-yl |
| Compound 1145 | S | S | C12H25-thiophen-2-yl | C12H25-thiophen-2-yl |

TABLE 45

| | $X^{c1}$ | $X^{c2}$ | $R^{c11}$ | $R^{c21}$ |
|---|---|---|---|---|
| Compound 1146 | S | S | C13H27-thiophen-2-yl | C13H27-thiophen-2-yl |
| Compound 1147 | S | S | C14H29-thiophen-2-yl | C14H29-thiophen-2-yl |
| Compound 1148 | S | S | C15H31-thiophen-2-yl | C15H31-thiophen-2-yl |
| Compound 1149 | S | S | C16H33-thiophen-2-yl | C16H33-thiophen-2-yl |
| Compound 1150 | S | S | C17H35-thiophen-2-yl | C17H35-thiophen-2-yl |
| Compound 1151 | S | S | C18H37-thiophen-2-yl | C18H37-thiophen-2-yl |
| Compound 1152 | S | S | C5H11-(4-substituted)-thiophen-2-yl | C5H11-(4-substituted)-thiophen-2-yl |
| Compound 1153 | S | S | C6H13-(4-substituted)-thiophen-2-yl | C6H13-(4-substituted)-thiophen-2-yl |

TABLE 45-continued

| | $X^{c1}$ | $X^{c2}$ | $R^{c11}$ | $R^{c21}$ |
|---|---|---|---|---|
| Compound 1154 | S | S | C7H15-(4-substituted)-thiophen-2-yl | C7H15-(4-substituted)-thiophen-2-yl |
| Compound 1155 | S | S | C8H17-(4-substituted)-thiophen-2-yl | C8H17-(4-substituted)-thiophen-2-yl |
| Compound 1156 | S | S | C9H19-(4-substituted)-thiophen-2-yl | C9H19-(4-substituted)-thiophen-2-yl |
| Compound 1157 | S | S | C10H21-(4-substituted)-thiophen-2-yl | C10H21-(4-substituted)-thiophen-2-yl |
| Compound 1158 | S | S | C11H23-(4-substituted)-thiophen-2-yl | C11H23-(4-substituted)-thiophen-2-yl |
| Compound 1159 | S | S | C12H25-(4-substituted)-thiophen-2-yl | C12H25-(4-substituted)-thiophen-2-yl |
| Compound 1160 | S | S | C13H27-(4-substituted)-thiophen-2-yl | C13H27-(4-substituted)-thiophen-2-yl |
| Compound 1161 | S | S | C14H29-(4-substituted)-thiophen-2-yl | C14H29-(4-substituted)-thiophen-2-yl |
| Compound 1162 | S | S | C15H31-(4-substituted)-thiophen-2-yl | C15H31-(4-substituted)-thiophen-2-yl |
| Compound 1163 | S | S | C16H33-(4-substituted)-thiophen-2-yl | C16H33-(4-substituted)-thiophen-2-yl |

TABLE 46

| | $X^{c1}$ | $X^{c2}$ | $R^{c11}$ | $R^{c21}$ |
|---|---|---|---|---|
| Compound 1164 | S | S | C17H35-(4-substituted)-thiophen-2-yl | C17H35-(4-substituted)-thiophen-2-yl |
| Compound 1165 | S | S | C18H37-(4-substituted)-thiophen-2-yl | C18H37-(4-substituted)-thiophen-2-yl |
| Compound 1166 | S | S | H | C5H11—* |
| Compound 1167 | S | S | H | C6H13—* |

TABLE 46-continued

| | $X^{c1}$ | $X^{c2}$ | $R^{c11}$ | $R^{c21}$ |
|---|---|---|---|---|
| Compound 1168 | S | S | H | $C_7H_{15}$—* |
| Compound 1169 | S | S | H | $C_8H_{17}$—* |
| Compound 1170 | S | S | H | $C_9H_{19}$—* |
| Compound 1171 | S | S | H | $C_{10}H_{21}$—* |
| Compound 1172 | S | S | H | $C_{11}H_{23}$—* |
| Compound 1173 | S | S | H | $C_{12}H_{25}$—* |
| Compound 1174 | S | S | H | $C_{13}H_{27}$—* |
| Compound 1175 | S | S | H | $C_{14}H_{29}$—* |
| Compound 1176 | S | S | H | $C_{15}H_{31}$—* |
| Compound 1177 | S | S | H | $C_{16}H_{33}$—* |
| Compound 1178 | S | S | H | $C_{17}H_{35}$—* |
| Compound 1179 | S | S | H | $C_{18}H_{37}$—* |
| Compound 1180 | S | S | Ph | $C_5H_{11}$—* |
| Compound 1181 | S | S | Ph | $C_6H_{13}$—* |
| Compound 1182 | S | S | Ph | $C_7H_{15}$—* |
| Compound 1183 | S | S | Ph | $C_8H_{17}$—* |
| Compound 1184 | S | S | Ph | $C_9H_{19}$—* |
| Compound 1185 | S | S | Ph | $C_{10}H_{21}$—* |
| Compound 1186 | S | S | Ph | $C_{11}H_{23}$—* |
| Compound 1187 | S | S | Ph | $C_{12}H_{25}$—* |
| Compound 1188 | S | S | Ph | $C_{13}H_{27}$—* |
| Compound 1189 | S | S | Ph | $C_{14}H_{29}$—* |
| Compound 1190 | S | S | Ph | $C_{15}H_{31}$—* |
| Compound 1191 | S | S | Ph | $C_{16}H_{33}$—* |
| Compound 1192 | S | S | Ph | $C_{17}H_{35}$—* |
| Compound 1193 | S | S | Ph | $C_{18}H_{37}$—* |

TABLE 46-continued

| | $X^{c1}$ | $X^{c2}$ | $R^{c11}$ | $R^{c21}$ |
|---|---|---|---|---|
| Compound 1194 | S | S | 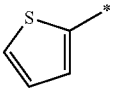 | $C_5H_{11}$—* |
| Compound 1195 | S | S | 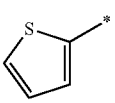 | $C_6H_{13}$—* |
| Compound 1196 | S | S | 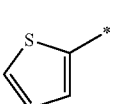 | $C_7H_{15}$—* |
| Compound 1197 | S | S | 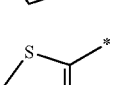 | $C_8H_{17}$—* |
| Compound 1198 | S | S | 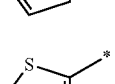 | $C_9H_{19}$—* |
| Compound 1199 | S | S | 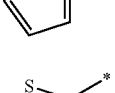 | $C_{10}C_{21}$—* |

TABLE 47

| | $X^{c1}$ | $X^{c2}$ | $R^{c11}$ | $R^{c21}$ |
|---|---|---|---|---|
| Compound 1200 | S | S | 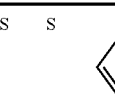 | $C_{11}C_{23}$—* |
| Compound 1201 | S | S | 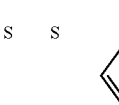 | $C_{12}C_{25}$—* |
| Compound 1202 | S | S | 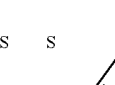 | $C_{13}C_{27}$—* |
| Compound 1203 | S | S | 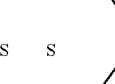 | $C_{14}C_{29}$—* |
| Compound 1204 | S | S | 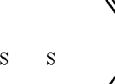 | $C_{15}C_{31}$—* |
| Compound 1205 | S | S | 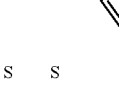 | $C_{16}C_{33}$—* |
| Compound 1206 | S | S | 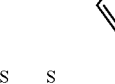 | $C_{17}C_{35}$—* |

TABLE 47-continued

| | $X^{c1}$ | $X^{c2}$ | $R^{c11}$ | $R^{c21}$ |
|---|---|---|---|---|
| Compound 1207 | S | S |  thienyl | $C_{18}C_{37}$—* |
| Compound 1208 | S | S | H | p-$C_5H_{11}$—Ph—* |
| Compound 1209 | S | S | H | p-$C_6H_{13}$—Ph—* |
| Compound 1210 | S | S | H | p-$C_7H_{15}$—Ph—* |
| Compound 1211 | S | S | H | p-$C_8H_{17}$—Ph—* |
| Compound 1212 | S | S | H | p-$C_9H_{19}$—Ph—* |
| Compound 1213 | S | S | H | p-$C_{10}H_{21}$—Ph—* |
| Compound 1214 | S | S | H | p-$C_{11}H_{23}$—Ph—* |
| Compound 1215 | S | S | H | p-$C_{12}H_{25}$—Ph—* |
| Compound 1216 | S | S | H | p-$C_{13}H_{27}$—Ph—* |
| Compound 1217 | S | S | H | p-$C_{14}H_{29}$—Ph—* |
| Compound 1218 | S | S | H | p-$C_{15}H_{31}$—Ph—* |
| Compound 1219 | S | S | H | p-$C_{16}H_{33}$—Ph—* |
| Compound 1220 | S | S | H | p-$C_{17}H_{35}$—Ph—* |
| Compound 1221 | S | S | H | p-$C_{18}H_{37}$—Ph—* |
| Compound 1222 | S | S | Ph | p-$C_5H_{11}$—Ph—* |
| Compound 1223 | S | S | Ph | p-$C_6H_{13}$—Ph—* |
| Compound 1224 | S | S | Ph | p-$C_7H_{15}$—Ph—* |
| Compound 1225 | S | S | Ph | p-$C_8H_{17}$—Ph—* |
| Compound 1226 | S | S | Ph | p-$C_9H_{19}$—Ph—* |
| Compound 1227 | S | S | Ph | p-$C_{10}H_{21}$—Ph—* |
| Compound 1228 | S | S | Ph | p-$C_{11}H_{23}$—Ph—* |
| Compound 1229 | S | S | Ph | p-$C_{12}H_{25}$—Ph—* |
| Compound 1230 | S | S | Ph | p-$C_{13}H_{27}$—Ph—* |
| Compound 1231 | S | S | Ph | p-$C_{14}H_{29}$—Ph—* |
| Compound 1232 | S | S | Ph | p-$C_{15}H_{31}$—Ph—* |
| Compound 1233 | S | S | Ph | p-$C_{16}H_{33}$—Ph—* |
| Compound 1234 | S | S | Ph | p-$C_{17}H_{35}$—Ph—* |
| Compound 1235 | S | S | Ph | p-$C_{18}H_{37}$—Ph—* |

TABLE 48

| | $X^{c1}$ | $X^{c2}$ | $R^{c11}$ | $R^{c21}$ |
|---|---|---|---|---|
| Compound 1236 | S | S | thienyl | p-$C_5H_{11}$—Ph—* |
| Compound 1237 | S | S | thienyl | p-$C_6H_{13}$—Ph—* |
| Compound 1238 | S | S | thienyl | p-$C_7H_{15}$—Ph—* |
| Compound 1239 | S | S | thienyl | p-$C_8H_{17}$—Ph—* |
| Compound 1240 | S | S | thienyl | p-$C_9H_{19}$—Ph—* |
| Compound 1241 | S | S | thienyl | p-$C_{10}H_{21}$—Ph—* |
| Compound 1242 | S | S | thienyl | p-$C_{11}H_{23}$—Ph—* |
| Compound 1243 | S | S | thienyl | p-$C_{12}H_{25}$—Ph—* |
| Compound 1244 | S | S | thienyl | p-$C_{13}H_{27}$—Ph—* |
| Compound 1245 | S | S | thienyl | p-$C_{14}H_{29}$—Ph—* |
| Compound 1246 | S | S | thienyl | p-$C_{15}H_{31}$—Ph—* |
| Compound 1247 | S | S | thienyl | p-$C_{16}H_{33}$—Ph—* |
| Compound 1248 | S | S | thienyl | p-$C_{17}H_{35}$—Ph—* |
| Compound 1249 | S | S | thienyl | p-$C_{18}H_{37}$—Ph—* |
| Compound 1250 | S | S | H | $C_5H_{11}$-thienyl-* |
| Compound 1251 | S | S | H | $C_6H_{13}$-thienyl-* |
| Compound 1252 | S | S | H | $C_7H_{15}$-thienyl-* |
| Compound 1253 | S | S | H | $C_8H_{17}$-thienyl-* |

TABLE 49

| | $X^{c1}$ | $X^{c2}$ | $R^{c11}$ | $R^{c21}$ |
|---|---|---|---|---|
| Compound 1254 | S | S | H | $C_9H_{19}$-thienyl-* |
| Compound 1255 | S | S | H | $C_{10}H_{21}$-thienyl-* |

TABLE 49-continued

| | $X^{c1}$ | $X^{c2}$ | $R^{c11}$ | $R^{c21}$ |
|---|---|---|---|---|
| Compound 1256 | S | S | H | 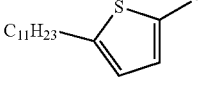 |
| Compound 1257 | S | S | H | 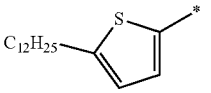 |
| Compound 1258 | S | S | H | 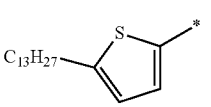 |
| Compound 1259 | S | S | H | 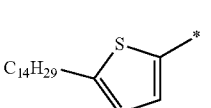 |
| Compound 1260 | S | S | H |  |
| Compound 1261 | S | S | H | 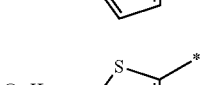 |
| Compound 1262 | S | S | H | 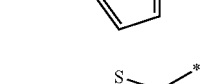 |
| Compound 1263 | S | S | Ph | 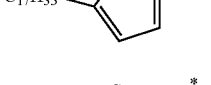 |
| Compound 1264 | S | S | Ph | 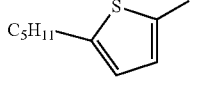 |
| Compound 1265 | S | S | Ph | 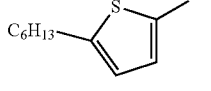 |
| Compound 1266 | S | S | Ph | 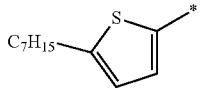 |
| Compound 1267 | S | S | Ph | 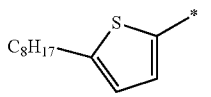 |
| Compound 1268 | S | S | Ph | 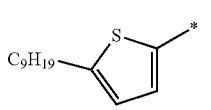 |
| Compound 1269 | S | S | Ph | 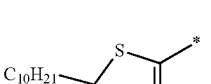 |
| Compound 1270 | S | S | Ph | 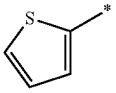 |
| Compound 1271 | S | S | Ph | 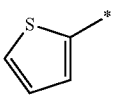 |

TABLE 50

| | $X^{c1}$ | $X^{c2}$ | $R^{c11}$ | $R^{c21}$ |
|---|---|---|---|---|
| Compound 1272 | S | S | Ph | 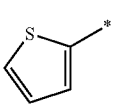 |
| Compound 1273 | S | S | Ph | 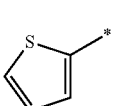 |
| Compound 1274 | S | S | Ph | 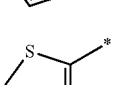 |
| Compound 1275 | S | S | Ph | 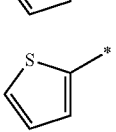 |
| Compound 1276 | S | S |  |  |
| Compound 1277 | S | S |  |  |
| Compound 1278 | S | S |  |  |
| Compound 1279 | S | S |  |  |
| Compound 1280 | S | S |  |  |
| Compound 1281 | S | S |  |  |
| Compound 1282 | S | S |  |  |

TABLE 50-continued

| | $X^{c1}$ | $X^{c2}$ | $R^{c11}$ | $R^{c21}$ |
|---|---|---|---|---|
| Compound 1283 | S | S | thiophen-2-yl | 5-$C_{12}H_{25}$-thiophen-2-yl |
| Compound 1284 | S | S | thiophen-2-yl | 5-$C_{13}H_{27}$-thiophen-2-yl |
| Compound 1285 | S | S | thiophen-2-yl | 5-$C_{14}H_{29}$-thiophen-2-yl |
| Compound 1286 | S | S | thiophen-2-yl | 5-$C_{15}H_{31}$-thiophen-2-yl |
| Compound 1287 | S | S | thiophen-2-yl | 5-$C_{16}H_{33}$-thiophen-2-yl |
| Compound 1288 | S | S | thiophen-2-yl | 5-$C_{17}H_{35}$-thiophen-2-yl |
| Compound 1289 | S | S | H | 4-$C_5H_{11}$-thiophen-2-yl |

TABLE 51

| | $X^{c1}$ | $X^{c2}$ | $R^{c11}$ | $R^{c21}$ |
|---|---|---|---|---|
| Compound 1290 | S | S | H | 4-$C_6H_{13}$-thiophen-2-yl |
| Compound 1291 | S | S | H | 4-$C_7H_{15}$-thiophen-2-yl |
| Compound 1292 | S | S | H | 4-$C_8H_{17}$-thiophen-2-yl |
| Compound 1293 | S | S | H | 4-$C_9H_{19}$-thiophen-2-yl |
| Compound 1294 | S | S | H | 4-$C_{10}H_{21}$-thiophen-2-yl |
| Compound 1295 | S | S | H | 4-$C_{11}H_{23}$-thiophen-2-yl |
| Compound 1296 | S | S | H | 4-$C_{12}H_{25}$-thiophen-2-yl |
| Compound 1297 | S | S | H | 4-$C_{13}H_{27}$-thiophen-2-yl |
| Compound 1298 | S | S | H | 4-$C_{14}H_{29}$-thiophen-2-yl |
| Compound 1299 | S | S | H | 4-$C_{15}H_{31}$-thiophen-2-yl |
| Compound 1300 | S | S | H | 4-$C_{16}H_{33}$-thiophen-2-yl |
| Compound 1301 | S | S | H | 4-$C_{17}H_{35}$-thiophen-2-yl |
| Compound 1302 | S | S | H | 4-$C_{18}H_{37}$-thiophen-2-yl |
| Compound 1303 | S | S | Ph | 4-$C_5H_{11}$-thiophen-2-yl |
| Compound 1304 | S | S | Ph | 4-$C_6H_{13}$-thiophen-2-yl |
| Compound 1305 | S | S | Ph | 4-$C_7H_{15}$-thiophen-2-yl |
| Compound 1306 | S | S | Ph | 4-$C_8H_{17}$-thiophen-2-yl |
| Compound 1307 | S | S | Ph | 4-$C_9H_{19}$-thiophen-2-yl |

TABLE 52

| | $X^{c1}$ | $X^{c2}$ | $R^{c11}$ | $R^{c21}$ |
|---|---|---|---|---|
| Compound 1308 | S | S | Ph | 4-$C_{10}H_{21}$-thiophen-2-yl |

TABLE 52-continued

| | X^{c1} | X^{c2} | R^{c11} | R^{c21} |
|---|---|---|---|---|
| Compound 1309 | S | S | Ph | C_{11}H_{23}-thienyl* |
| Compound 1310 | S | S | Ph | C_{12}H_{25}-thienyl* |
| Compound 1311 | S | S | Ph | C_{13}H_{27}-thienyl* |
| Compound 1312 | S | S | Ph | C_{14}H_{29}-thienyl* |
| Compound 1313 | S | S | Ph | C_{15}H_{31}-thienyl* |
| Compound 1314 | S | S | Ph | C_{16}H_{33}-thienyl* |
| Compound 1315 | S | S | Ph | C_{17}H_{35}-thienyl* |
| Compound 1316 | S | S | Ph | C_{18}H_{37}-thienyl* |
| Compound 1317 | S | S | thienyl* | C_5H_{11}-thienyl* |
| Compound 1318 | S | S | thienyl* | C_6H_{13}-thienyl* |
| Compound 1319 | S | S | thienyl* | C_7H_{15}-thienyl* |
| Compound 1320 | S | S | thienyl* | C_8H_{17}-thienyl* |
| Compound 1321 | S | S | thienyl* | C_9H_{19}-thienyl* |
| Compound 1322 | S | S | thienyl* | C_{10}H_{21}-thienyl* |
| Compound 1323 | S | S | thienyl* | C_{11}H_{23}-thienyl* |
| Compound 1324 | S | S | thienyl* | C_{12}H_{25}-thienyl* |
| Compound 1325 | S | S | thienyl* | C_{13}H_{27}-thienyl* |

TABLE 53

| | X^{c1} | X^{c2} | R^{c11} | R^{c21} |
|---|---|---|---|---|
| Compound 1326 | S | S | thienyl* | C_{14}H_{29}-thienyl* |
| Compound 1327 | S | S | thienyl* | C_{15}H_{31}-thienyl* |
| Compound 1328 | S | S | thienyl* | C_{16}H_{33}-thienyl* |
| Compound 1329 | S | S | thienyl* | C_{17}H_{35}-thienyl* |
| Compound 1330 | S | S | thienyl* | C_{18}H_{37}-thienyl* |
| Compound 1331 | S | S | C_{10}H_{21}—* | p-C_5H_{11}—Ph—* |
| Compound 1332 | S | S | C_{10}H_{21}—* | p-C_6H_{13}—Ph—* |
| Compound 1333 | S | S | C_{10}H_{21}—* | p-C_7H_{15}—Ph—* |
| Compound 1334 | S | S | C_{10}H_{21}—* | p-C_8H_{17}—Ph—* |
| Compound 1335 | S | S | C_{10}H_{21}—* | p-C_9H_{19}—Ph—* |
| Compound 1336 | S | S | C_{10}H_{21}—* | p-C_{10}H_{21}—Ph—* |
| Compound 1337 | S | S | C_{10}H_{21}—* | p-C_{11}H_{23}—Ph—* |
| Compound 1338 | S | S | C_{10}H_{21}—* | p-C_{12}H_{25}—Ph—* |
| Compound 1339 | S | S | C_{10}H_{21}—* | p-C_{13}H_{27}—Ph—* |

TABLE 53-continued

| | $X^{c1}$ | $X^{c2}$ | $R^{c11}$ | $R^{c21}$ |
|---|---|---|---|---|
| Compound 1340 | S | S | $C_{10}H_{21}$—* | p-$C_{14}H_{29}$—Ph—* |
| Compound 1341 | S | S | $C_{10}H_{21}$—* | p-$C_{15}H_{31}$—Ph—* |
| Compound 1342 | S | S | $C_{10}H_{21}$—* | p-$C_{16}H_{33}$—Ph—* |
| Compound 1343 | S | S | $C_{10}H_{21}$—* | p-$C_{17}H_{35}$—Ph—* |
| Compound 1344 | S | S | $C_{10}H_{21}$—* | p-$C_{18}H_{37}$—Ph—* |
| Compound 1345 | S | S | $C_{12}H_{25}$—* | 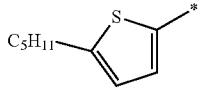 |
| Compound 1346 | S | S | $C_{12}H_{25}$—* | 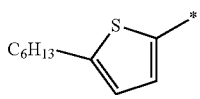 |
| Compound 1347 | S | S | $C_{12}H_{25}$—* | 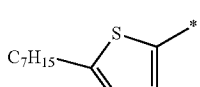 |
| Compound 1348 | S | S | $C_{12}H_{25}$—* | 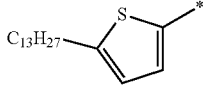 |
| Compound 1349 | S | S | $C_{12}H_{25}$—* | 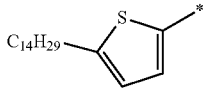 |
| Compound 1350 | S | S | $C_{12}H_{25}$—* | 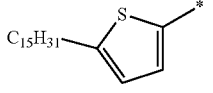 |
| Compound 1351 | S | S | $C_{12}H_{25}$—* | 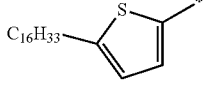 |
| Compound 1352 | S | S | $C_{12}H_{25}$—* | 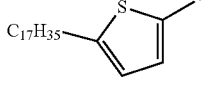 |

TABLE 54

| | $X^{c1}$ | $X^{c2}$ | $R^{c11}$ | $R^{c21}$ |
|---|---|---|---|---|
| Compound 1353 | S | S | $C_{12}H_{25}$—* | 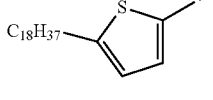 |
| Compound 1354 | S | S | $C_{12}H_{25}$—* | |
| Compound 1355 | S | S | $C_{12}H_{25}$—* | |
| Compound 1356 | S | S | $C_{12}H_{25}$—* | |
| Compound 1357 | S | S | $C_{12}H_{25}$—* | |
| Compound 1358 | S | S | $C_{12}H_{25}$—* | |
| Compound 1359 | S | S | 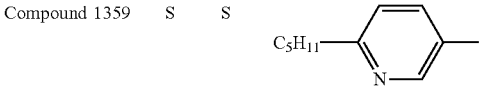 | 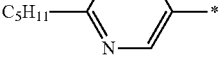 |

TABLE 54-continued

| | $X^{c1}$ | $X^{c2}$ | $R^{c11}$ | $R^{c21}$ |
|---|---|---|---|---|
| Compound 1360 | S | S | 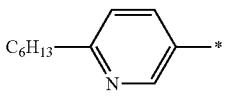 C$_6$H$_{13}$—pyridyl—* | 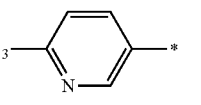 C$_6$H$_{13}$—pyridyl—* |
| Compound 1361 | S | S | 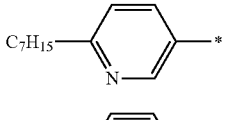 C$_7$H$_{15}$—pyridyl—* | 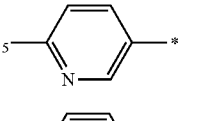 C$_7$H$_{15}$—pyridyl—* |
| Compound 1362 | S | S | 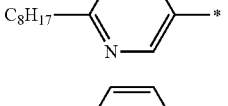 C$_8$H$_{17}$—pyridyl—* | 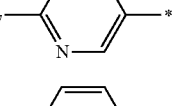 C$_8$H$_{17}$—pyridyl—* |
| Compound 1363 | S | S | 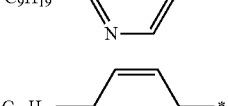 C$_9$H$_{19}$—pyridyl—* | 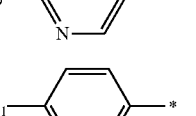 C$_9$H$_{19}$—pyridyl—* |
| Compound 1364 | S | S | 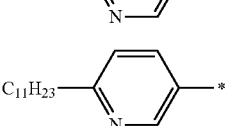 C$_{10}$H$_{21}$—pyridyl—* | 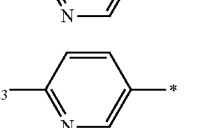 C$_{10}$H$_{21}$—pyridyl—* |
| Compound 1365 | S | S | 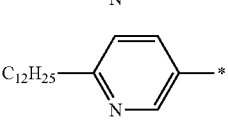 C$_{11}$H$_{23}$—pyridyl—* | 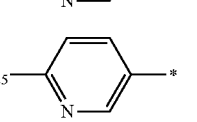 C$_{11}$H$_{23}$—pyridyl—* |
| Compound 1366 | S | S | 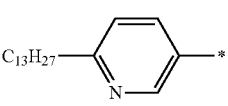 C$_{12}$H$_{25}$—pyridyl—* | 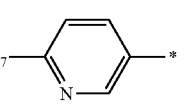 C$_{12}$H$_{25}$—pyridyl—* |
| Compound 1367 | S | S | 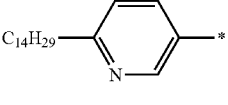 C$_{13}$H$_{27}$—pyridyl—* | 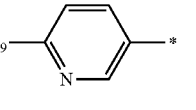 C$_{13}$H$_{27}$—pyridyl—* |
| Compound 1368 | S | S | 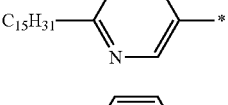 C$_{14}$H$_{29}$—pyridyl—* | 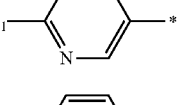 C$_{14}$H$_{29}$—pyridyl—* |
| Compound 1369 | S | S | 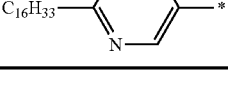 C$_{15}$H$_{31}$—pyridyl—* | 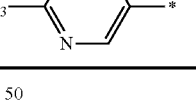 C$_{15}$H$_{31}$—pyridyl—* |
| Compound 1370 | S | S |  C$_{16}$H$_{33}$—pyridyl—* |  C$_{16}$H$_{33}$—pyridyl—* |

TABLE 55

| | $X^{c1}$ | $X^{c2}$ | $R^{c11}$ | $R^{c21}$ |
|---|---|---|---|---|
| Compound 1371 | S | S | 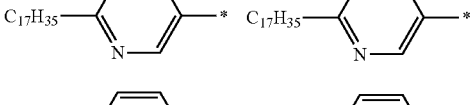 C$_{17}$H$_{35}$—pyridyl—* | 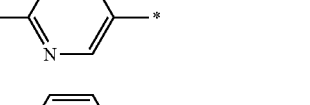 C$_{17}$H$_{35}$—pyridyl—* |
| Compound 1372 | S | S | 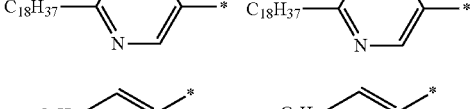 C$_{18}$H$_{37}$—pyridyl—* | 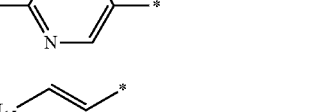 C$_{18}$H$_{37}$—pyridyl—* |
| Compound 1373 | S | S |  C$_7$H$_{15}$—CH=CH—* |  C$_7$H$_{15}$—CH=CH—* |

TABLE 55-continued

| | $X^{c1}$ | $X^{c2}$ | $R^{c11}$ | $R^{c21}$ |
|---|---|---|---|---|
| Compound 1374 | S | S | $C_6H_{13}$–CH=CH–* | $C_6H_{13}$–CH=CH–* |
| Compound 1375 | S | S | $C_8H_{17}$–CH=CH–* | $C_8H_{17}$–CH=CH–* |
| Compound 1376 | S | S | $C_9H_{19}$–CH=CH–* | $C_9H_{19}$–CH=CH–* |
| Compound 1377 | S | S | $C_{10}H_{21}$–CH=CH–* | $C_{10}H_{21}$–CH=CH–* |
| Compound 1378 | S | S | $C_{11}H_{23}$–CH=CH–* | $C_{11}H_{23}$–CH=CH–* |
| Compound 1379 | S | S | $C_{12}H_{25}$–CH=CH–* | $C_{12}H_{25}$–CH=CH–* |
| Compound 1380 | S | S | $C_{13}H_{27}$–CH=CH–* | $C_{13}H_{27}$–CH=CH–* |
| Compound 1381 | S | S | $C_{14}H_{29}$–CH=CH–* | $C_{14}H_{29}$–CH=CH–* |
| Compound 1382 | S | S | $C_{15}H_{31}$–CH=CH–* | $C_{15}H_{31}$–CH=CH–* |
| Compound 1383 | S | S | $C_{16}H_{33}$–CH=CH–* | $C_{16}H_{33}$–CH=CH–* |
| Compound 1384 | S | S | $C_{17}H_{35}$–CH=CH–* | $C_{17}H_{35}$–CH=CH–* |
| Compound 1385 | S | S | $C_{18}H_{37}$–CH=CH–* | $C_{18}H_{37}$–CH=CH–* |
| Compound 1386 | S | S | $C_5H_{11}$–C≡C–* | $C_5H_{11}$–C≡C–* |
| Compound 1387 | S | S | $C_6H_{13}$–C≡C–* | $C_6H_{13}$–C≡C–* |
| Compound 1388 | S | S | $C_7H_{15}$–C≡C–* | $C_7H_{15}$–C≡C–* |

TABLE 56

| | $X^{c1}$ | $X^{c2}$ | $X^{c11}$ | $X^{c21}$ |
|---|---|---|---|---|
| Compound 1389 | S | S | $C_8H_{17}$–C≡C–* | $C_8H_{17}$–C≡C–* |
| Compound 1390 | S | S | $C_9H_{19}$–C≡C–* | $C_9H_{19}$–C≡C–* |
| Compound 1391 | S | S | $C_{10}H_{21}$–C≡C–* | $C_{10}H_{21}$–C≡C–* |
| Compound 1392 | S | S | $C_{11}H_{23}$–C≡C–* | $C_{11}H_{23}$–C≡C–* |
| Compound 1393 | S | S | $C_{12}H_{25}$–C≡C–* | $C_{12}H_{25}$–C≡C–* |

TABLE 56-continued

| | $X^{c1}$ | $X^{c2}$ | $X^{c11}$ | $X^{c21}$ |
|---|---|---|---|---|
| Compound 1394 | S | S | 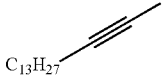C₁₃H₂₇ | 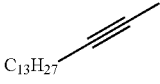C₁₃H₂₇ |
| Compound 1395 | S | S | 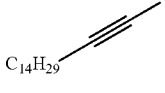C₁₄H₂₉ | 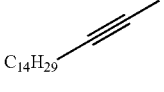C₁₄H₂₉ |
| Compound 1396 | S | S | 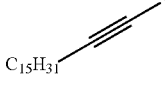C₁₅H₃₁ | 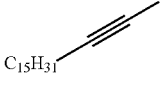C₁₅H₃₁ |
| Compound 1397 | S | S | 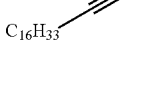C₁₆H₃₃ | 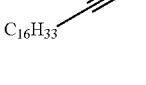C₁₆H₃₃ |
| Compound 1398 | S | S | 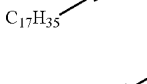C₁₇H₃₅ | 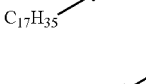C₁₇H₃₅ |
| Compound 1399 | S | S | 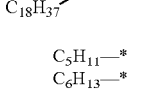C₁₈H₃₇ | 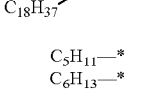C₁₈H₃₇ |
| Compound 1400 | O | O | C₅H₁₁—* | C₅H₁₁—* |
| Compound 1401 | O | O | C₆H₁₃—* | C₆H₁₃—* |
| Compound 1402 | O | O | C₇H₁₅—* | C₇H₁₅—* |
| Compound 1403 | O | O | C₈H₁₇—* | C₈H₁₇—* |
| Compound 1404 | O | O | C₉H₁₉—* | C₉H₁₉—* |
| Compound 1405 | O | O | C₁₀H₂₁—* | C₁₀H₂₁—* |
| Compound 1406 | O | O | C₁₁H₂₃—* | C₁₁H₂₃—* |
| Compound 1407 | O | O | C₁₂H₂₅—* | C₁₂H₂₅—* |
| Compound 1408 | O | O | C₁₃H₂₇—* | C₁₃H₂₇—* |
| Compound 1409 | O | O | C₁₄H₂₉—* | C₁₄H₂₉—* |
| Compound 1410 | O | O | C₁₅H₃₁—* | C₁₅H₃₁—* |
| Compound 1411 | O | O | C₁₆H₃₃—* | C₁₆H₃₃—* |
| Compound 1412 | O | O | C₁₇H₃₅—* | C₁₇H₃₅—* |
| Compound 1413 | O | O | C₁₈H₃₇—* | C₁₈H₃₇—* |
| Compound 1414 | O | O | p-C₅H₁₁—Ph—* | p-C₅H₁₁—Ph—* |
| Compound 1415 | O | O | p-C₆H₁₃—Ph—* | p-C₆H₁₃—Ph—* |
| Compound 1416 | O | O | p-C₇H₁₅—Ph—* | p-C₇H₁₅—Ph—* |
| Compound 1417 | O | O | p-C₈H₁₇—Ph—* | p-C₈H₁₇—Ph—* |
| Compound 1418 | O | O | p-C₉H₁₉—Ph—* | p-C₉H₁₉—Ph—* |
| Compound 1419 | O | O | p-C₁₀H₂₁—Ph—* | p-C₁₀H₂₁—Ph—* |
| Compound 1420 | O | O | p-C₁₁H₂₃—Ph—* | p-C₁₁H₂₃—Ph—* |
| Compound 1421 | O | O | p-C₁₂H₂₅—Ph—* | p-C₁₂H₂₅—Ph—* |

TABLE 57

| | $X^{c1}$ | $X^{c2}$ | $R^{c11}$ | $R^{c21}$ |
|---|---|---|---|---|
| Compound 1422 | O | O | p-C₁₃H₂₇—Ph—* | p-C₁₃H₂₇—Ph—* |
| Compound 1423 | O | O | p-C₁₄H₂₉—Ph—* | p-C₁₄H₂₉—Ph—* |
| Compound 1424 | O | O | p-C₁₅H₃₁—Ph—* | p-C₁₅H₃₁—Ph—* |
| Compound 1425 | O | O | p-C₁₆H₃₃—Ph—* | p-C₁₆H₃₃—Ph—* |
| Compound 1426 | O | O | p-C₁₇H₃₅—Ph—* | p-C₁₇H₃₅—Ph—* |

TABLE 57-continued

| | $X^{c1}$ | $X^{c2}$ | $R^{c11}$ | $R^{c21}$ |
|---|---|---|---|---|
| Compound 1427 | O | O | p-C₁₈H₃₇—Ph—* | p-C₁₈H₃₇—Ph—* |
| Compound 1428 | O | O |  |  |
| Compound 1429 | O | O |  |  |
| Compound 1430 | O | O |  |  |
| Compound 1431 | O | O |  |  |
| Compound 1432 | O | O |  |  |
| Compound 1433 | O | O |  |  |
| Compound 1434 | O | O |  |  |
| Compound 1435 | O | O |  |  |
| Compound 1436 | O | O |  |  |
| Compound 1437 | O | O |  |  |
| Compound 1438 | O | O |  |  |
| Compound 1439 | O | O |  |  |
| Compound 1440 | O | O |  |  |

TABLE 57-continued

| | $X^{c1}$ | $X^{c2}$ | $R^{c11}$ | $R^{c21}$ |
|---|---|---|---|---|
| Compound 1441 | O | O | 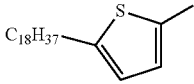 C$_{18}$H$_{37}$ | 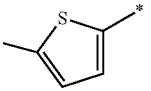 C$_{18}$H$_{37}$ |
| Compound 1442 | S | S | C$_4$H$_3$OC$_4$H$_8$—* | C$_4$H$_3$OC$_4$H$_8$—* |
| Compound 1443 | S | S | C$_2$H$_5$OC$_2$H$_4$—* | C$_2$H$_5$OC$_2$H$_4$—* |

TABLE 58

| | $X^{c1}$ | $X^{c2}$ | $R^{c11}$ | $R^{c12}$ |
|---|---|---|---|---|
| Compound 1444 | S | S | C$_6$H$_{13}$OC$_4$H$_8$—* | C$_6$H$_{13}$OC$_4$H$_8$—* |
| Compound 1445 | S | S | C$_2$H$_5$OC$_4$H$_8$—* | C$_2$H$_5$OC$_4$H$_8$—* |
| Compound 1446 | S | S | CH$_3$OC$_3$H$_6$—* | CH$_3$OC$_3$H$_6$—* |
| Compound 1447 | S | S | 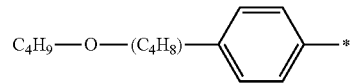 C$_4$H$_9$—O—(C$_4$H$_8$)— | 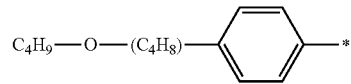 C$_4$H$_9$—O—(C$_4$H$_8$)— |
| Compound 1448 | S | S | 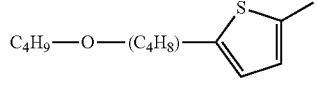 C$_4$H$_9$—O—(C$_4$H$_8$)— | 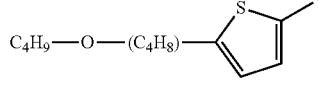 C$_4$H$_9$—O—(C$_4$H$_8$)— |
| Compound 1449 | S | S | 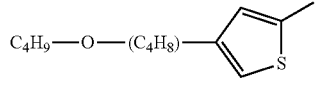 C$_4$H$_9$—O—(C$_4$H$_8$)— | 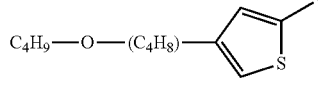 C$_4$H$_9$—O—(C$_4$H$_8$)— |
| Compound 1450 | S | S | PhC$_3$H$_6$—* | PhC$_3$H$_6$—* |
| Compound 1451 | S | S | PhOC$_3$H$_6$—* | PhOC$_3$H$_6$—* |
| Compound 1452 | S | S | 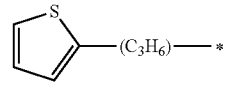 —(C$_3$H$_6$)—* | 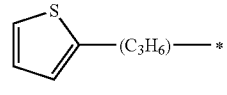 —(C$_3$H$_6$)—* |
| Compound 1453 | S | S | 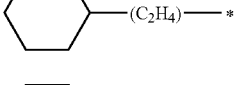 —(C$_2$H$_4$)—* | 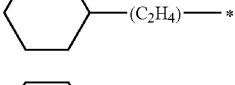 —(C$_2$H$_4$)—* |
| Compound 1454 | S | S | 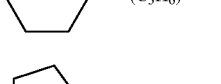 —(C$_3$H$_6$)—* |  —(C$_3$H$_6$)—* |
| Compound 1455 | S | S | 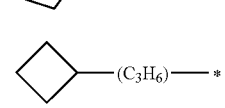 —(C$_3$H$_6$)—* | 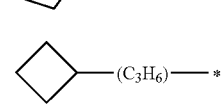 —(C$_3$H$_6$)—* |
| Compound 1456 | S | S | 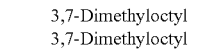 —(C$_3$H$_6$)—* | 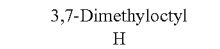 —(C$_3$H$_6$)—* |
| Compound 1457 | S | S | 3,7-Dimethyloctyl | 3,7-Dimethyloctyl |
| Compound 1458 | S | S | 3,7-Dimethyloctyl | H |
| Compound 1459 | S | S | 2-Ethylhexyl | 2-Ethylhexyl |
| Compound 1460 | S | S | 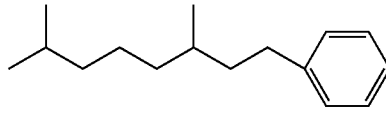 | 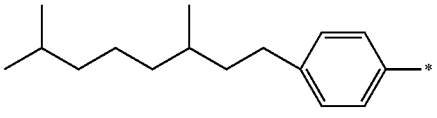 |
| Compound 1461 | S | S | 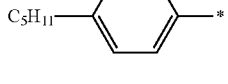 C$_5$H$_{11}$—* | 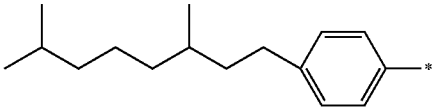 |

TABLE 59

| | $X^{c1}$ | $X^{c2}$ | $R^{c11}$ | $R^{c21}$ |
|---|---|---|---|---|
| Compound 1462 | S | S | 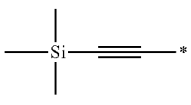 | 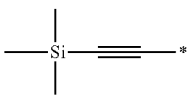 |
| Compound 1463 | S | S | 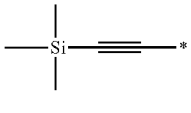 | H |
| Compound 1464 | S | S | 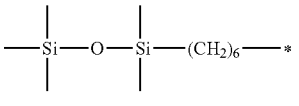 | 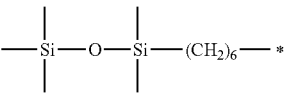 |
| Compound 1465 | S | S | C$_5$H$_{11}$—* | 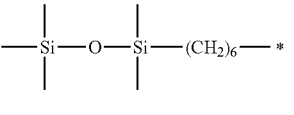 |
| Compound 1466 | S | S | 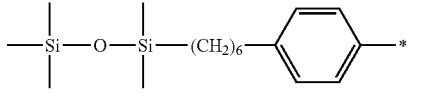 | 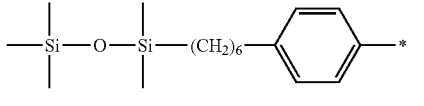 |
| Compound 1467 | S | S | 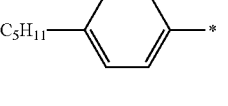 | 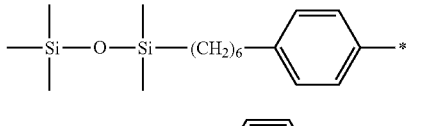 |
| Compound 1468 | S | S | 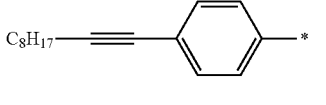 | 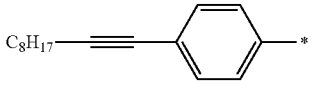 |
| Compound 1469 | S | S | 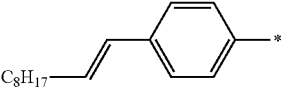 | 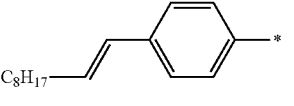 |
| Compound 1470 | S | S | 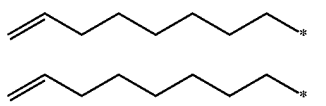 | 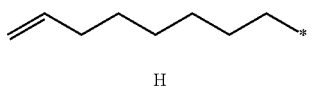 |
| Compound 1471 | S | S | 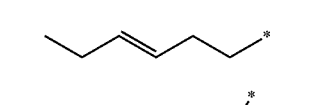 | H |
| Compound 1472 | S | S | 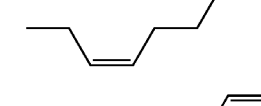 | 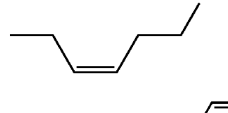 |
| Compound 1473 | S | S | 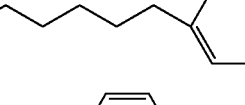 | 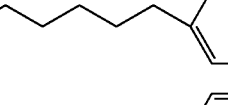 |
| Compound 1474 | S | S | 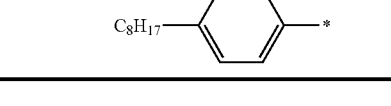 | 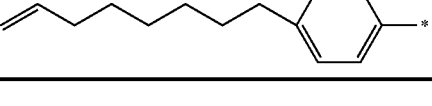 |
| Compound 1475 | S | S | 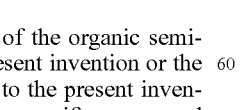 | 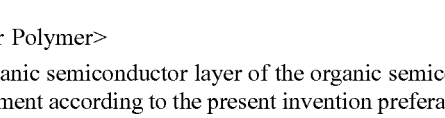 |

In the organic semiconductor layer of the organic semiconductor element according to the present invention or the organic semiconductor film according to the present invention described below, the content of the specific compound is preferably 30 to 100 mass %, more preferably 50 to 100 mass %, and even more preferably 70 to 100 mass %. In a case where a binder polymer described below is not contained, the content is preferably 90 to 100 mass % and more preferably 95 to 100 mass %.

<Binder Polymer>

The organic semiconductor layer of the organic semiconductor element according to the present invention preferably contains the binder polymer.

The organic semiconductor element according to the present invention may be an organic semiconductor element having a layer including the organic semiconductor layer and the binder polymer.

The types of the binder polymer are not particularly limited, and well-known binder polymers can be used.

Examples of the binder polymer include a polystyrene resin, an acrylic resin, rubber, and a thermoplastic elastomer.

Among these, as the binder polymer, a polymer compound (a polymer having a monomer unit having a benzene ring group) having a benzene ring is preferable. The content of the monomer unit having a benzene ring group is not particularly limited. However, the content is preferably 50 mol % or greater, more preferably 70 mol % or greater, and even more preferably 90 mol % or greater with respect to the entire monomer unit. The upper limit is not particularly limited, but examples of the upper limit include 100 mol %.

Examples of the binder polymer include polystyrene, poly($\alpha$-methylstyrene), polyvinyl cinnamate, poly(4-vinylphenyl), and poly(4-methylstyrene).

A weight-average molecular weight of the binder polymer is not particularly limited, but is preferably 1,000 to 2,000,000, more preferably 3,000 to 1,000,000, and even more preferably 5,000 to 600,000.

In a case where a solvent described below is used, it is preferable that the binder polymer exhibits solubility higher than the solubility of the specific compound in a used solvent. If the above aspect is adopted, mobility and heat stability of the obtained organic semiconductor are further improved.

A content of the binder polymer in the organic semiconductor layer of the organic semiconductor element of the present invention is preferably 1 to 200 parts by mass, more preferably 10 to 150 parts by mass, and even more preferably 20 to 120 parts by mass with respect to 100 parts by mass of the content of the specific compound. If the content is within the above range, mobility and heat stability of the obtained organic semiconductor are further improved.

<Other Components>

Other components may be included other than the specific compound and the binder polymer may be included in the organic semiconductor layer according to the organic semiconductor element of the present invention.

As other components, known additives and the like can be used.

In the organic semiconductor layer, a content of the components other than the specific compound and the binder polymer is preferably 10 mass % or less, more preferably 5 mass % or less, even more preferably 1 mass % or less, and particularly preferably 0.1 mass % or less. If the content of other components is within the above range, film formability is improved, and mobility and heat stability of the obtained organic semiconductor are further improved.

(Method of Forming Organic Semiconductor Layer)

The method of forming the organic semiconductor layer according to the organic semiconductor element of the present invention is not particularly limited. However, a desired organic semiconductor layer can be formed by applying the composition for forming the organic semiconductor film according to the present invention described below to a source electrode, a drain electrode, and a gate insulating film and performing a drying treatment, if necessary.

(Method of Manufacturing Organic Semiconductor Element and Organic Semiconductor Film)

The organic semiconductor element and an organic semiconductor film of the present invention is preferably manufactured using the composition for forming an organic semiconductor film of the present invention described below.

A method of manufacturing an organic semiconductor film or an organic semiconductor element by using the composition for forming an organic semiconductor film of the present invention is not particularly limited, and known methods can be adopted. Examples thereof include a method of manufacturing an organic semiconductor film by applying the composition onto a predetermined base material and if necessary, performing a drying treatment.

The method of applying the composition onto a base material is not particularly limited, and known methods can be adopted. Examples thereof include an ink jet printing method, a flexographic printing method, a bar coating method, a spin coating method, a knife coating method, a doctor blade method, and the like. Among these, an ink jet printing method and a flexographic printing method are preferable.

Preferred examples of the flexographic printing method include an aspect in which a photosensitive resin plate is used as a flexographic printing plate. By printing the composition onto a substrate according to the aspect, a pattern can be easily formed.

Among these, the method of manufacturing an organic semiconductor element and an organic semiconductor film according to the present invention preferably include an applying step of applying an composition for forming an organic semiconductor film according to the present invention to a substrate and a removing step of removing at least a portion of a solvent having a boiling point of 100° C. or higher included in the composition for forming the organic semiconductor film.

<Solvent Having Boiling Point of 100° C. or Higher>

The composition for forming the organic semiconductor film according to the present invention contains a solvent having a boiling point of 100° C. or higher (hereinafter, referred to a "specific solvent").

Examples of the specific solvent include a hydrocarbon-based solvent such as octane, decane, toluene, xylene, mesitylene, ethylbenzene, decalin, 1-methylnaphthalene, tetralin, and dimethyltetralin, a ketone-based solvent such as methyl isobutyl ketone and cyclohexanone, a halogenated hydrocarbon-based solvent such as tetrachloroethane, chlorobenzene, dichlorobenzene, chlorotoluene, 1-fluoronaphthalene, and 1-chloronaphthalene, an ester-based solvent such as butyl acetate and amyl acetate, an alcohol-based solvent such as butanol, pentanol, hexanol, cyclohexanol, methyl cellosolve, ethyl cellosolve, and ethylene glycol, an ether-based solvent such as dibutyl ether, dioxane, anisole, 4-tertiary butyl anisole, and m-dimethoxybenzene, an amide-based solvent such as N,N-dimethylformamide and N,N-dimethylacetamide, an imide-based solvent such as 1-methyl-2-pyrrolidone and 1-methyl-2-imidazolidinone, a sulfoxide-based solvent such as dimethyl sulfoxide, and a nitrile-based solvent such as butyronitrile and benzonitrile.

The specific solvent may be used singly or two or more types thereof may be used in combination.

Among these, a hydrocarbon-based solvent, a halogenated hydrocarbon-based solvent and/or an ether-based solvent are preferable, toluene, xylene, mesitylene, tetralin, dichlorobenzene, or anisole is more preferable, and toluene is even more preferable.

If the specific solvent is the aforementioned solvent, coating properties are excellent, and thus an organic semiconductor film can be easily formed.

In view of stability of the composition for forming the organic semiconductor film, forming an even film, and drying, the boiling point of the specific solvent in normal pressure is 100° C. or higher, preferably 100° C. to 300° C., more preferably 100° C. to 200° C., and even more preferably 100° C. to 150° C.

The drying treatment in the removing step is a treatment performed if necessary, and the optimal treatment conditions are suitably selected according to the type of the specific compound used and the solvent. In view of further improving mobility and heat stability of the obtained organic semiconductor and improving productivity, a heating temperature is preferably 30° C. to 100° C. and more preferably 40° C. to 80° C., and a heating time is preferably 10 to 300 minutes and more preferably 30 to 180 minutes.

A thickness of the formed organic semiconductor layer is not particularly limited. From the viewpoint of mobility and heat stability of the obtained organic semiconductor, the film thickness is preferably 10 to 500 nm and more preferably 30 to 200 nm.

<Organic Semiconductor Element>

The organic semiconductor element is not particularly limited, but is preferably an organic semiconductor element having 2 to 5 terminals, and more preferably an organic semiconductor element having 2 or 3 terminals.

It is preferable that the organic semiconductor element is not a photoelectric conversion element.

The organic semiconductor element according to the present invention is preferably a non-luminous organic semiconductor element.

Examples of a 2-terminal element include a rectifier diode, a constant voltage diode, a PIN diode, a Schottky barrier diode, a surge protection diode, a diac, a varistor, a tunnel diode, and the like.

Examples of a 3-terminal element include a bipolar transistor, a Darlington transistor, a field effect transistor, insulated gate bipolar transistor, a uni-junction transistor, a static induction transistor, a gate turn-off thyristor, a triac, a static induction thyristor, and the like.

Among these, a rectifier diode and transistors are preferable, and a field effect transistor is more preferable.

An aspect of the organic thin film transistor of the present invention will be described with reference to drawings.

FIG. 1 is a schematic cross-sectional view of an aspect of an organic semiconductor element (organic thin film transistor (organic TFT)) of the present invention.

In FIG. 1, an organic thin film transistor 100 includes a substrate 10, a gate electrode 20 disposed on the substrate 10, a gate insulating film 30 covering the gate electrode 20, a source electrode 40 and a drain electrode 42 which contact a surface of the gate insulating film 30 that is on the side opposite to the gate electrode 20 side, an organic semiconductor film 50 covering a surface of the gate insulating film 30 between the source electrode 40 and the drain electrode 42, and a sealing layer 60 covering each member. The organic thin film transistor 100 is a bottom gate-bottom contact type organic thin film transistor.

In FIG. 1, the organic semiconductor film 50 corresponds to a film formed of the composition described above.

Hereinafter, the substrate, the gate electrode, the gate insulating film, the source electrode, the drain electrode, the organic semiconductor film, the sealing layer, and methods for forming each of these will be specifically described.

<Substrate>

The substrate plays a role of supporting the gate electrode, the source electrode, the drain electrode, and the like which will be described later.

The type of the substrate is not particularly limited, and examples thereof include a plastic substrate, a glass substrate, a ceramic substrate, and the like. Among these, from the viewpoint of applicability to each device and costs, a glass substrate or a plastic substrate is preferable.

Examples of materials of the plastic substrate include a thermosetting resin (for example, an epoxy resin, a phenol resin, a polyimide resin, or a polyester resin (for example, polyethylene terephthalate (PET) or polyethylene naphthalate (PEN)) and a thermoplastic resin (for example, a phenoxy resin, a polyethersulfone, polysulfone, or polyphenylene sulfone).

Examples of materials of the ceramic substrate include alumina, aluminum nitride, zirconia, silicon, silicon nitride, silicon carbide, and the like.

Examples of materials of the glass substrate include soda lime glass, potash glass, borosilicate glass, quartz glass, aluminosilicate glass, lead glass, and the like.

<Gate Electrode, Source Electrode, and Drain Electrode>

Examples of materials of the gate electrode, the source electrode, and the drain electrode include a metal such as gold (Au), silver, aluminum (Al), copper, chromium, nickel, cobalt, titanium, platinum, tantalum, magnesium, calcium, barium, or sodium; a conductive oxide such as $InO_2$, $SnO_2$, or indium tin oxide (ITO); a conductive polymer such as polyaniline, polypyrrole, polythiophene, polyacetylene, or polydiacetylene; a semiconductor such as silicon, germanium, or gallium arsenide; a carbon material such as fullerene, carbon nanotubes, or graphite; and the like. Among these, a metal is preferable, and silver and aluminum are more preferable.

A thickness of each of the gate electrode, the source electrode, and the drain electrode is not particularly limited, but is preferably 20 to 200 nm.

A method of forming the gate electrode, the source electrode, and the drain electrode is not particularly limited, but examples thereof include a method of vacuum vapor-depositing or sputtering an electrode material onto a substrate, a method of coating a substrate with a composition for forming an electrode, a method of printing a composition for forming an electrode onto a substrate, and the like. Furthermore, in a case where the electrode is patterned, examples of the patterning method include a photolithography method; a printing method such as ink jet printing, screen printing, offset printing, or relief printing; a mask vapor deposition method; and the like.

<Gate Insulating Film>

Examples of materials of the gate insulating film include a polymer such as polymethyl methacrylate, polystyrene, polyvinylphenol, polyimide, polycarbonate, polyester, polyvinylalcohol, polyvinyl acetate, polyurethane, polysulfone, polybenzoxazole, polysilsesquioxane, an epoxy resin, or a phenol resin; an oxide such as silicon dioxide, aluminum oxide, or titanium oxide; a nitride such as silicon nitride; and the like. Among these materials, in view of the compatibility with the organic semiconductor film, a polymer is preferable.

In a case where a polymer is used as the material of the gate insulating film, it is preferable to use a cross-linking agent (for example, melamine) in combination. If the cross-linking agent is used in combination, the polymer is cross-linked, and durability of the formed gate insulating film is improved.

A film thickness of the gate insulating film is not particularly limited, but is preferably 100 to 1,000 nm.

A method of forming the gate insulating film is not particularly limited, but examples thereof include a method of coating a substrate, on which the gate electrode is formed, with a composition for forming a gate insulating film, a method of vapor-depositing or sputtering the material of the gate insulating film onto a substrate on which the gate electrode is formed, and the like. A method of coating the aforementioned substrate with the composition for forming a gate insulating film is not particularly limited, and it is possible to use a known method (a bar coating method, a spin coating method, a knife coating method, or a doctor blade method).

In a case where the gate insulating film is formed by coating the substrate with the composition for forming a gate insulating film, for the purpose of removing the solvent, causing cross-linking, or the like, the composition may be heated (baked) after coating.

<Organic Semiconductor Film>

The organic semiconductor film according to the present invention is a film formed of the composition for forming the organic semiconductor film according to the present invention.

The method of forming the organic semiconductor film is not particularly limited. A desired organic semiconductor film can be formed by applying the aforementioned composition to a source electrode, a drain electrode, and a gate insulating film and performing a drying treatment, if desired.

<Binder Polymer Layer>

The organic semiconductor element of the present invention preferably has a layer of the aforementioned binder polymer between the aforementioned organic semiconductor layer and an insulating film, and more preferably has a layer of the aforementioned binder polymer between the aforementioned organic semiconductor layer and the gate insulating film. A film thickness of the binder polymer layer is not particularly limited, but is preferably 20 to 500 nm. The binder polymer layer should be a layer containing the aforementioned polymer, and is preferably a layer composed of the aforementioned binder polymer.

A method of forming the binder polymer layer is not particularly limited, and a known method (a bar coating method, a spin coating method, a knife coating method, a doctor blade method, or an ink jet method) can be used.

In a case where the binder polymer layer is formed by performing coating by using a composition for forming a binder polymer layer, for the purpose of removing a solvent, causing cross-linking, or the like, the composition may be heated (baked) after coating.

<Sealing Layer>

From the viewpoint of durability, the organic semiconductor element of the present invention preferably includes a sealing layer as an outermost layer. In the sealing layer, a known sealant can be used.

A thickness of the sealing layer is not particularly limited, but is preferably 0.2 to 10 μm.

A method of forming the sealing layer is not particularly limited, but examples thereof include a method of coating a substrate, on which the gate electrode, the gate insulating film, the source electrode, the drain electrode, and the organic semiconductor film are formed, with a composition for forming a sealing layer, and the like. Specific examples of the method of coating the substrate with the composition for forming a sealing layer are the same as the examples of the method of coating the substrate with the composition for forming a gate insulating film. In a case where the organic semiconductor film is formed by coating the substrate with the composition for forming a sealing layer, for the purpose of removing the solvent, causing cross-linking, or the like, the composition may be heated (baked) after coating.

Figure 2:
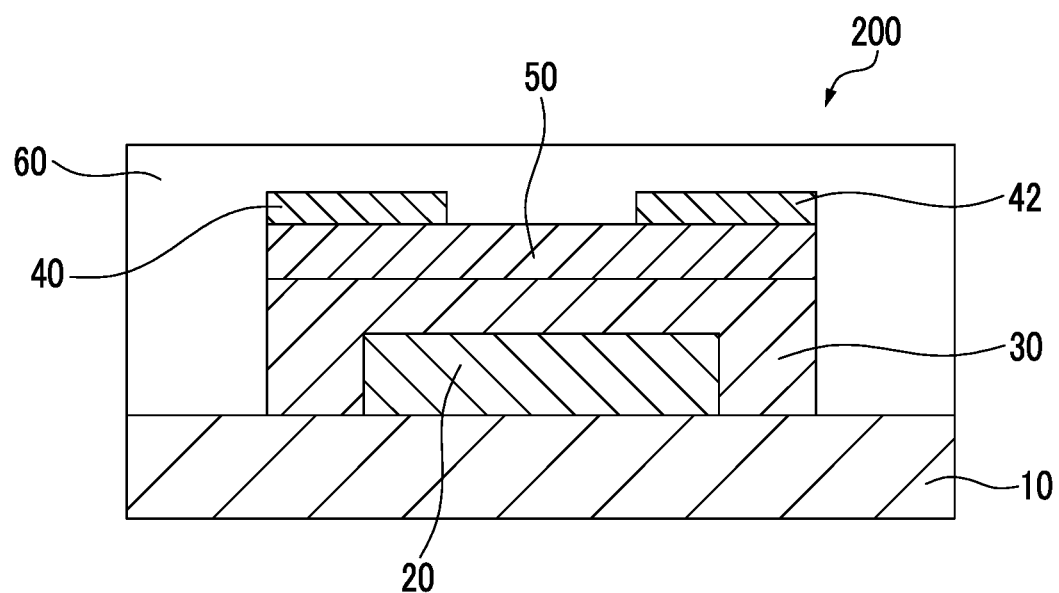
FIG. 2 is a schematic cross-sectional view of another aspect of the organic semiconductor element of the present invention.

FIG. 2 is a schematic cross-sectional view of another aspect of the organic semiconductor element (organic thin film transistor) of the present invention.

In FIG. 2, an organic thin film transistor 200 includes the substrate 10, the gate electrode 20 disposed on the substrate 10, the gate insulating film 30 covering the gate electrode 20, the organic semiconductor film 50 disposed on the gate insulating film 30, the source electrode 40 and the drain electrode 42 disposed on the organic semiconductor film 50, and the sealing layer 60 covering each member. Herein, the source electrode 40 and the drain electrode 42 are formed using the aforementioned composition of the present invention. The organic thin film transistor 200 is a top contact type organic thin film transistor.

The substrate, the gate electrode, the gate insulating film, the source electrode, the drain electrode, the organic semiconductor film, and the sealing layer are as described above.

In FIGS. 1 and 2, the aspects of the bottom gate-bottom contact type organic thin film transistor and the bottom gate-top contact type organic thin film transistor were specifically described. However, the organic semiconductor element of the present invention can also suitably used in a top gate-bottom contact type organic thin film transistor and a top gate-top contact type organic thin film transistor.

The organic thin film transistor described above can be suitably used for electronic paper and a display device.

(Composition for Forming Organic Semiconductor Film)

The composition for forming the organic semiconductor film according to the present invention contains a solvent having a boiling point of 100° C. or higher and a compound represented by Formula 1, and a content of the compound represented by Formula 1 is 20 mass % or less with respect to a total amount of the composition for forming the organic semiconductor film.

The composition for forming the organic semiconductor film according to the present invention preferably contains a binder polymer.

The specific compound, the binder polymer, and the solvent in the composition for forming the organic semiconductor film according to the present invention are the same as the aforementioned specific compound, the aforementioned binder polymer, and the aforementioned solvent, and preferable aspects are also the same.

The content of the specific compound of the composition for forming the organic semiconductor film according to the present invention is 20 mass % or less, preferably 0.001 to 15 mass %, and more preferably 0.01 to 10 mass % with respect to the total amount of the composition for forming the organic semiconductor film. In a case where two or more types of specific compounds are used in combination, the total content of the specific compounds is preferably in the range described above. If the content of the specific compound is in the range described above, the organic semiconductor element having high mobility and high driving stability can be obtained, storage stability of the composition for forming the organic semiconductor film is also satisfactory.

The content of the specific compound is preferably 30 to 100 mass %, more preferably 50 to 100 mass %, and even more preferably 70 to 100 mass % with respect to the total solid content of the composition for forming the organic semiconductor film. In a case where a binder polymer described below is not contained, the total content is preferably 90 to 100 mass % and more preferably 95 to 100 mass %. The solid content is an amount of the component except for the volatile component such as the solvent.

The content of the binder polymer in the composition for forming the organic semiconductor film according to the present invention is preferably greater than 0 mass % and 20 mass % or less, more preferably 0.01 to 15 mass %, and even more preferably 0.25 to 10 mass % with respect to the total amount of the composition for forming the organic semiconductor film. If the content is in the range described above, mobility and heat resistance of the obtained organic semiconductor become more excellent.

The composition for forming the organic semiconductor film according to the present invention may include other component in addition to the specific compound and the binder polymer.

As the component, well-known additives may be used.

The content of the component in addition to the specific compound and the binder polymer in the composition for forming the organic semiconductor film according to the present invention is preferably 10 mass % or less, more preferably 5 mass % or less, even more preferably 1 mass % or less, and particularly preferably 0.1 mass % or less with respect to the total solid content. If the content is in the range described above, film formability is improved, and mobility and heat stability of the obtained organic semiconductor are further improved.

The viscosity of the composition for forming the organic semiconductor film according to the present invention is not particularly limited. However, in view of excellent coating properties, the viscosity is preferably 3 to 100 mPa·s, more preferably 5 to 50 mPa·s, and even more preferably 9 to 40 mPa·s. The viscosity according to the present invention refers to viscosity at 25° C.

As a method of measuring the viscosity, a measuring method in conformity of JIS Z8803 is preferable.

The method of manufacturing the composition for forming the organic semiconductor film according to the present invention is not particularly limited, and well-known methods can be applied. For example, a desired composition can be obtained by adding a specific amount of a specific compound in the solvent and applying an suitable stirring treatment. In a case where the binder polymer is used, the specific compound and the binder polymer are simultaneously or sequentially added, so as to suitably manufacture the composition.

EXAMPLES

Hereinafter, the present invention will be more specifically described based on examples. The materials and the amount thereof used, the proportion of the materials, the content and procedure of treatments, and the like described in the following examples can be suitably changed within a scope that does not depart from the gist of the present invention. Accordingly, the scope of the present invention is not limited to the following specific examples. Herein, unless otherwise specified, "part" and "%" are based on mass.

Specific Compounds and Synthesis Examples

Structures of E-1 to E-10 used in the examples and C-1 to C-2 used in the comparative examples are provided below.

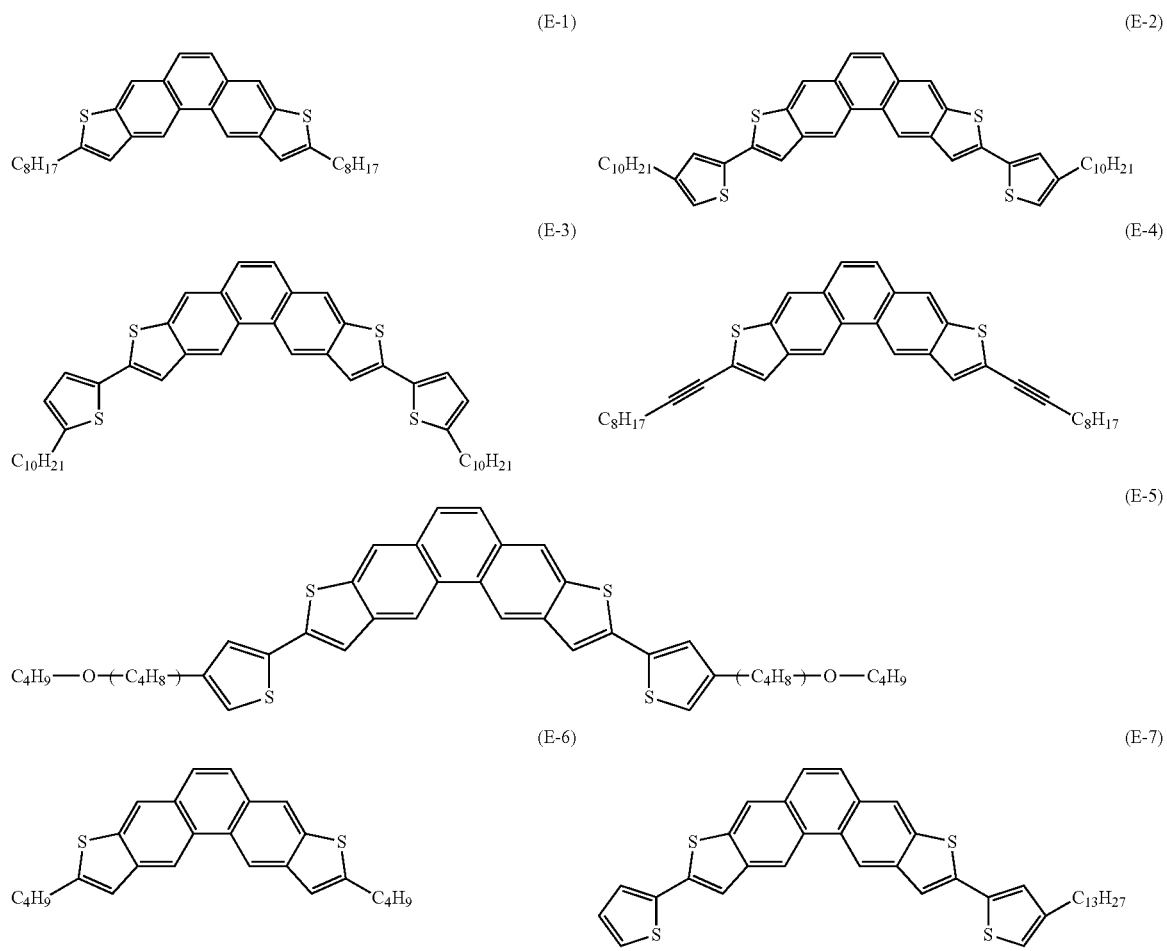

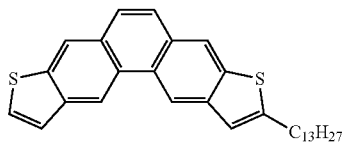
(E-8)

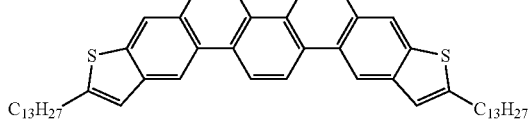
(E-9)

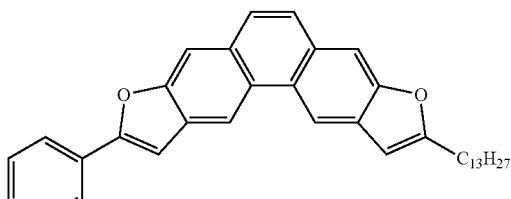
(E-10)

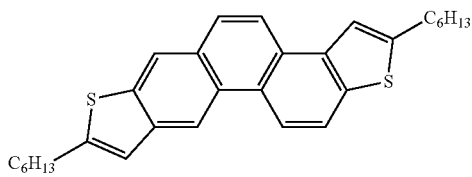
(C-1)

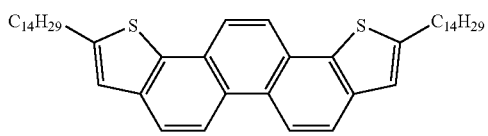

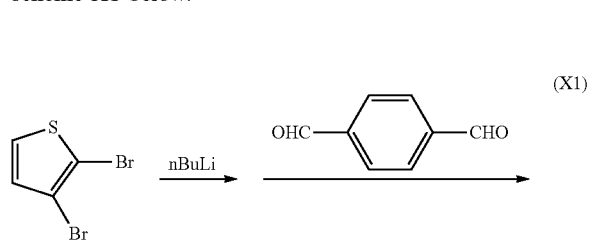
(C-2)

<Synthesis of E-1>

An intermediate M1 was synthesized according to a scheme X1 below.

(X1)

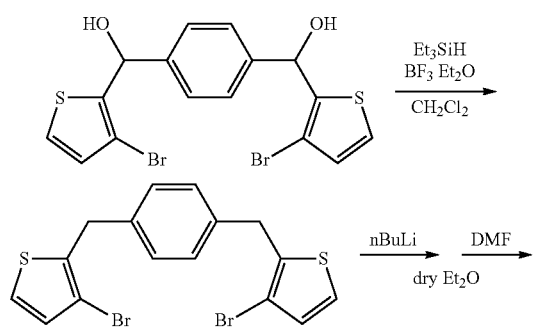

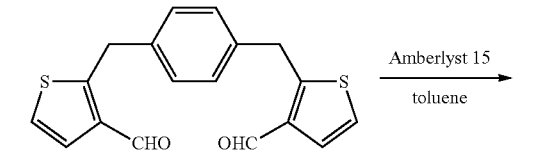

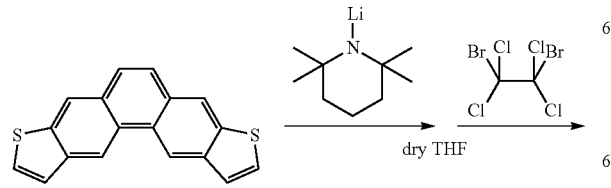

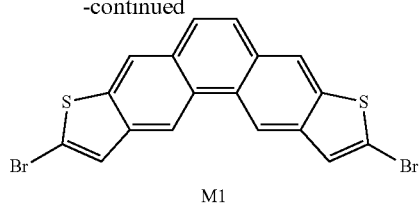
M1

The intermediate M1 and octyl zinc chloride were fused by negishi coupling reaction, so as to synthesize a compound E-1.

(X2)

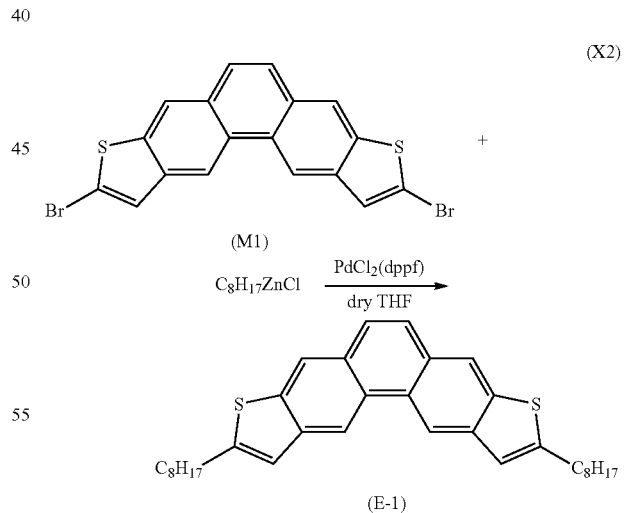
(E-1)

<Synthesis of E-2 to E-10>

E-2 to E-10 were also synthesized in the same manner as in E-1, except for changing an organic zinc compound fused with the intermediate M1 to suitable compounds.

<Synthesis of C-1>

A compound C-1 was synthesized according to the method described in JP2010-177637A.

<Synthesis of C-2>

A compound C-2 was synthesized according to the method disclosed in WO2013/168048A.

Examples 1 to 10 and Comparative Examples 1 to 2

<Manufacturing of TFT Element>

The specific compound presented in Table 60 or a comparative compound (1 mg) and toluene (1 mL) were mixed with each other and heated to 100° C., and the composition for forming the organic semiconductor film was obtained.

An organic semiconductor film was formed by casting this composition to a substrate for measuring FET characteristics which was heated to 90° C. under the nitrogen atmosphere, and an organic thin film transistor element for measuring FET characteristics was obtained. As the substrate for measuring FET characteristics, a silicon substrate in a bottom gate-bottom contact structure including chromium/gold (gate width W=100 mm, gate length L=100 µm) arranged in a comb-shape as source and drain electrodes and SiO$_2$ (film thickness: 200 nm) as an insulating film was used.

The obtained composition was applied to a substrate for measuring FET characteristics by flexographic printing. Specifically, a flexographic printability test machine F1 (manufactured by IGT Testing Systems) was used as a printing machine, and AFP DSH 1.70% (manufactured by Asahi Kasei Corporation)/a solid image was used as a flexographic resin version. After printing was performed in a pressure between a plate and a substrate of 60 N and a transportation speed of 0.4 m/second, drying was performed at 40° C. for two hours, so as to form an organic semiconductor film, and an organic thin film transistor element (organic TFT element) for measuring FET characteristics was obtained.

As the substrate for measuring FET characteristics, a silicon substrate in a bottom gate-bottom contact structure including chromium/gold (gate width W=100 mm, gate length L=100 µm) arranged in a comb-shape as source and drain electrodes and SiO$_2$ (film thickness: 200 nm) as an insulating film was used.

The ink was applied to the substrate for measuring FET characteristics by ink jet printing. Specifically, DPP2831 (manufactured by FUJIFILM Global Graphic Systems Co., Ltd.) was used as an inkjet device and 10 pL heads were used, so as to form a solid film with a jetting frequency of 2 Hz and a pitch between dots of 20 µm. Thereafter, drying was performed for one hour at 70° C., so as to form an organic semiconductor film, and the organic TFT element for measuring FET characteristics was obtained.

In the examples and the comparative examples, evaluations of mobility, coating film formability, and heat resistance described below with respect to the organic TFT element obtained by ink jet printing were the same as those of the organic TFT element obtained by casting the composition.

<Carrier Mobility (Mobility)>

With respect to the FET characteristics of the organic thin film transistor elements of the respective examples and the respective comparative examples, carrier mobility was evaluated under normal pressure and the nitrogen atmosphere by employing a semiconductor parameter analyzer (manufactured by Agilent, 4156C) to which a semi automatic prober (manufactured by Vector Semiconductor Co., Ltd., AX-2000) was connected.

A voltage of −80 V was applied between source electrodes and drain electrodes of the respective organic thin film transistor elements (FET elements), a gate voltage was changed in the range of 20 V to −100 V, an equation below presenting a drain current Id was used, so as to calculate carrier mobility µ.

$$Id=(w/2L)\mu Ci(Vg-Vth)^2$$

In the equation, L represents a gate length, W represents a gate width, Ci represents capacitance of the insulating layer per unit area, Vg represents a gate voltage, and Vth represents a threshold voltage. The numerical value of the carrier mobility is required to be practically 0.01 or greater, preferably 0.1 or greater, and more preferably 0.3 or greater.

The expression "no characteristics" in the tables presents the created element did not have TFT characteristics.

<Coating Film Formability>

The compound according to the present invention or the comparative compound (5 mg) and toluene (1 mL) were mixed and heated to 100° C., so as to obtain a non-luminescent organic semiconductor solution. This coating liquid was casted under nitrogen atmosphere to the entire surface of the substrate which was heated to 90° C. and on which channels for 50 elements were formed, so as to form an organic semiconductor thin film, and 50 organic thin film transistor elements for measuring FET characteristics were obtained. Evaluation standards of the coating film formability were set as below, and the evaluation results were presented in Table 60.

[Evaluation standard] A: 45 or more elements out of the obtained 50 elements were driven as organic thin film transistor element B: Less than 45 elements out of the obtained 50 elements were driven as organic thin film transistor element <Heat Resistance>

After the manufactured respective organic thin film transistor elements were heated for one hour at 130° C. in a nitrogen glove box, carrier mobility µ was measured, so as to calculate a carrier mobility maintenance rate after heating by the equation below.

Carrier mobility maintenance rate after heating (%)=Carrier mobility (after heating)/carrier mobility (initial value)×100

Obtained results were evaluated according to evaluation standards below. The evaluation results are presented in Table 60. The expression "N/A" in the table means that a heat resistance was not performed since a created element did not have TFT characteristics.

[Evaluation Standard]

A: Carrier mobility maintenance rate after heating was 95% or greater

B: Carrier mobility maintenance rate after heating was 70% or greater and less than 95%

C: Carrier mobility maintenance rate after heating was 40% or greater and less than 70%

D: Carrier mobility maintenance rate after heating was 20% or greater and less than 40%

E: Carrier mobility maintenance rate after heating was less than 20%

TABLE 60

|  | Specific compound | Mobility | Solubility | Coating film formability | Heat resistance |
| --- | --- | --- | --- | --- | --- |
| Example 1 | E-1 | 1.1 | A | A | A |
| Example 2 | E-2 | 1 | B | A | A |
| Example 3 | E-3 | 0.5 | A | A | A |
| Example 4 | E-4 | 0.7 | B | A | A |

TABLE 60-continued

| | Specific compound | Mobility | Solubility | Coating film formability | Heat resistance |
|---|---|---|---|---|---|
| Example 5 | E-5 | 0.6 | A | A | B |
| Example 6 | E-6 | 0.3 | A | A | A |
| Example 7 | E-7 | 0.05 | B | A | A |
| Example 8 | E-8 | 0.03 | B | A | B |
| Example 9 | E-9 | 0.03 | C | A | A |
| Example 10 | E-10 | 0.01 | B | A | A |
| Comparative Example 1 | C-1 | No Characteristics | C | B | N/A |
| Comparative Example 2 | C-2 | $5 \times 10^{-3}$ | C | B | D |

Examples 11 to 16, Comparative Examples 3 to 4

<Manufacturing of TFT Elements>

Respective evaluations were performed in the same manner as in Examples 1 to 10 and Comparative Examples 1 to 2 except for mixing the specific compound of the present invention or the comparative compound presented in Table 61, the binder polymer presented in Table 61, and the solvent presented in Table 61 in the concentrations presented in Table 61, performing heating to 100° C., and using the resultant as the composition for forming the organic semiconductor film. The respective evaluation results are presented in Table 61.

Abbreviations used in Table 61 are as below.

PαMS: Poly(α-methylstyrene), Mw=300,000, manufactured by Sigma-Aldrich Co. LLC.)

THF: Tetrahydrofuran

TABLE 61

| | Specific compound | Binder polymer | Solvent | Concentration of semiconductor in composition (mass %) | Concentration of binder polymer in composition (mass %) | Mobility | Heat resistance | Coating film formability |
|---|---|---|---|---|---|---|---|---|
| Example 11 | E-1 | PαMS | Toluene | 0.5 | 0.5 | 1.2 | A | A |
| Example 12 | E-2 | PαMS | Toluene | 0.5 | 0.5 | 1.2 | A | A |
| Example 13 | E-5 | PαMS | Toluene | 0.5 | 0.5 | 0.8 | A | A |
| Example 14 | E-6 | PαMS | Toluene | 0.5 | 0.5 | 0.5 | A | A |
| Example 15 | E-1 | PαMS | THF | 0.5 | 0.5 | 0.1 | B | A |
| Example 16 | E-1 | PαMS | Toluene | 0.5 | 12.0 | 0.02 | B | A |
| Comparative Example 3 | C-1 | PαMS | Toluene | 0.5 | 0.5 | $2 \times 10^{-3}$ | D | B |
| Comparative Example 4 | C-2 | PαMS | Toluene | 0.5 | 0.5 | No characteristics | N/A | B |

Comparative Examples 5 to 21

The organic semiconductor films were formed in the same manner as in Example 1 to 16 except for weighing the specific compounds and toluene (1 mL) presented in Tables 60 and 61 and further the binder polymer (5 mg) in the examples presented in Table 61 such that the content of the respective specific compounds become 21 mass %, performing mixture, performing heating to 100° C., and using the resultant as the composition for forming the organic semiconductor film. However, in all of Comparative Examples 5 to 21, due to insoluble matters, various defects were generated, and thus TFT characteristics were not exhibited.

EXPLANATION OF REFERENCES

10: substrate
20: gate electrode
30: gate insulating film
40: source electrode
42: drain electrode
50: organic semiconductor film
60: sealing layer
100,200: organic thin film transistor

What is claimed is:

1. An organic semiconductor element comprising:
a compound represented by Formula 1 below in an organic semiconductor layer:

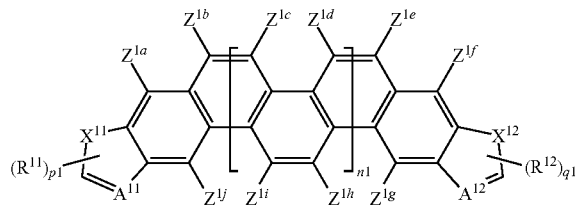

(1)

wherein, in Formula 1, $X^{11}$ and $X^{12}$ each independently represent a chalcogen atom, $Z^{1a}$ to $Z^{1j}$ each independently represent a hydrogen atom or a halogen atom, $A^{11}$ represents $=CR^{411}-$ or a nitrogen atom, $R^{411}$ represents a hydrogen atom or a group represented by $R^{11}$, $A^{12}$ represents $=CR^{412}-$ or a nitrogen atom, $R^{412}$ represents a hydrogen atom or a group represented by $R^{12}$, n1 represents 0 or 1, p1 represents an integer of 0 to 2 in a case where $A^{11}$ is $=CR^{411}-$ and represents 0 or 1 in a case where $A^{11}$ is a nitrogen atom, q1 represents an integer of 0 to 2 in a case where $A^{12}$ is $=CR^{412}-$ and represents 0 or 1 in a case where $A^{12}$ is a nitrogen atom, at least one of p1 or q1 is not 0, $R^{11}$ and $R^{12}$ each independently represent a halogen atom, an aryl group, a heteroaryl group, or a group represented by Formula W below:

$$-S^W-L^W-T^W \quad (W)$$

wherein, in Formula W, $S^W$ represents a single bond or an alkylene group represented by $-(CR^S_2)_k-$, $R^S$ each independently represent a hydrogen atom or a halogen atom, k represents an integer of 1 to 17, $L^W$ represents a single bond, a divalent linking group represented by any one of Formulae L-1 to L-16 below, or a group obtained by bonding any two or more of divalent linking groups represented by Formulae L-1 to L-16 below, $T^W$ represents an alkyl group, a cyano group, a vinyl group, an ethynyl group, an aryl group, a heteroaryl group, an oxyethylene group, an oligooxyethylene group of which the repetition number of oxyethylene units is two or greater, an oligosiloxane group having two or more silicon atoms, or a trialkylsilyl group, and

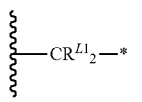 (L-1)

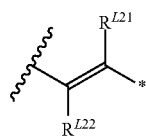 (L-2)

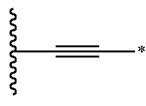 (L-3)

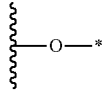 (L-4)

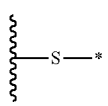 (L-5)

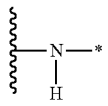 (L-6)

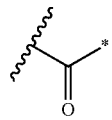 (L-7)

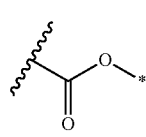 (L-8)

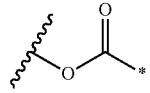 (L-9)

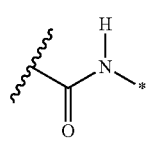 (L-10)

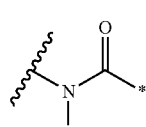 (L-11)

-continued

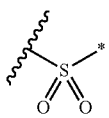 (L-12)

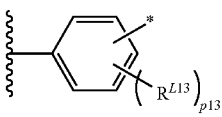 (L-13)

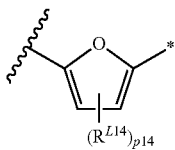 (L-14)

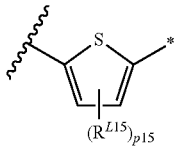 (L-15)

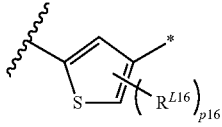 (L-16)

wherein, in Formulae L-1 to L-16, * and wavy line portions represent bonding positions to other structures, p13 represents an integer of 0 to 4, p14, p15, and p16 each independently represent an integer of 0 to 2, $R^{L1}$, $R^{L21}$, $R^{L22}$, $R^{L13}$, $R^{L14}$, $R^{L15}$, and $R^{L16}$ each independently represent a hydrogen atom or a substituent.

2. The organic semiconductor element according to claim 1, wherein all of $Z^{1a}$ to $Z^{1j}$ are hydrogen atoms.

3. The organic semiconductor element according to claim 1, wherein n1 is not 0.

4. The organic semiconductor element according to claim 1, wherein:
at least one of $R^{11}$ or $R^{12}$ is a group represented by Formula W.

5. The organic semiconductor element according to claim 1, wherein p1 and q1 are 1.

6. The organic semiconductor element according to claim 1, wherein both of $X^{11}$ and $X^{12}$ are S atoms, $A^{11}$ is =$CR^{A11}$—, and $A^{12}$ is =$CR^{A12}$—.

7. The organic semiconductor element according to claim 1, wherein a compound represented by Formula 1 is a compound represented by Formula 2 below:

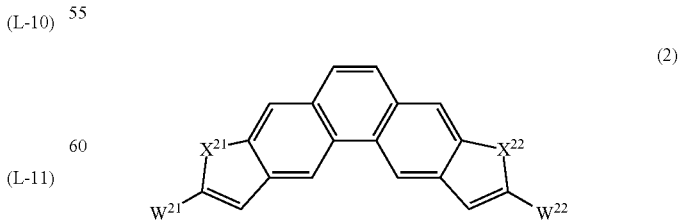 (2)

wherein, in Formula 2, $X^{21}$ and $X^{22}$ each independently represent a chalcogen atom, $W^{21}$ and $W^{22}$ each independently represent a group represented by Formula W.

8. The organic semiconductor element according to claim 1, wherein the compound represented by Formula 1 is a line symmetric structure.

9. The organic semiconductor element according to claim 1, wherein the number of carbon atoms in the group represented by Formula W is 5 to 40.

10. The organic semiconductor element according to claim 1, wherein $L^W$ is a single bond, a divalent linking group represented by any one of Formulae L-1 to L-4 and Formulae L-13 to L-16, or a divalent linking group obtained by bonding two or more divalent linking groups represented by any one of Formulae L-1 to L-4 and Formulae L-13 to L-16.

11. The organic semiconductor element according to claim 1, wherein $L^W$ is a single bond or a divalent linking group represented by any one of Formulae L-1 to L-4 and Formulae L-13 to L-16.

12. The organic semiconductor element according to claim 1, wherein $S^W$ is a single bond.

13. The organic semiconductor element according to claim 1, wherein $L^W$ is a single bond or a divalent linking group represented by any one of Formula L-1 and Formulae L-13 to L-16.

14. The organic semiconductor element according to claim 1, wherein $T^W$ is an alkyl group.

15. The organic semiconductor element according to claim 1, wherein a group represented by Formula W is an alkyl group.

16. A composition for forming an organic semiconductor film, comprising:
a solvent having a boiling point of 100° C. or higher; and
a compound represented by Formula 1,
wherein a content of the compound represented by Formula 1 is from 0.001% by mass to 15% by mass with respect to a total amount of the composition for forming an organic semiconductor film:

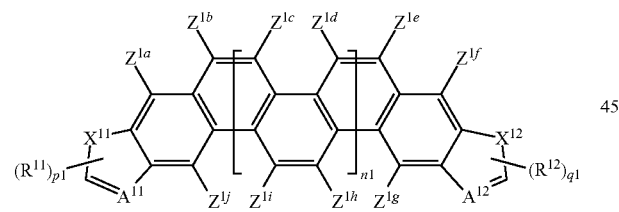
(1)

wherein, in Formula 1, $X^{11}$ and $X^{12}$ each independently represent a chalcogen atom, $Z^{1a}$ to $Z^{1j}$ each independently represent a hydrogen atom or a halogen atom, $A^{11}$ represents $=CR^{411}$— or a nitrogen atom, $R^{411}$ represents a hydrogen atom or a group represented by $R^{11}$, $A^{12}$ represents $=CR^{412}$— or a nitrogen atom, $R^{412}$ represents a hydrogen atom or a group represented by $R^{12}$, n1 represents 0 or 1, p1 represents an integer of 0 to 2 in a case where $A^{11}$ is $=CR^{411}$— and represents 0 or 1 in a case where $A^{11}$ is a nitrogen atom, q1 represents an integer of 0 to 2 in a case where $A^{12}$ is $=CR^{412}$—, and represents 0 or 1 in a case where $A^{12}$ is a nitrogen atom, $R^{11}$ and $R^{12}$ each independently represent a halogen atom, an aryl group, a heteroaryl group, or a group represented by Formula W below:

—$S^W$-$L^W$-$T^W$ (W)

wherein, in Formula W, $S^W$ represents a single bond or an alkylene group represented by —$(CR^S_2)_k$—, $R^S$ each independently represent a hydrogen atom or a halogen atom, k represents an integer of 1 to 17, $L^W$ represents a single bond, a divalent linking group represented by any one of Formulae L-1 to L-16 below, or a group obtained by bonding any two or more of divalent linking groups represented by Formulae L-1 to L-16 below, $T^W$ represents an alkyl group, a cyano group, a vinyl group, an ethynyl group, an aryl group, a heteroaryl group, an oxyethylene group, an oligooxyethylene group of which the repetition number of oxyethylene units is two or greater, an oligosiloxane group having two or more silicon atoms, or a trialkylsilyl group, and

(L-1)

(L-2)

(L-3)

(L-4)

(L-5)

(L-6)

(L-7)

(L-8)

(L-9)

(L-10)

-continued

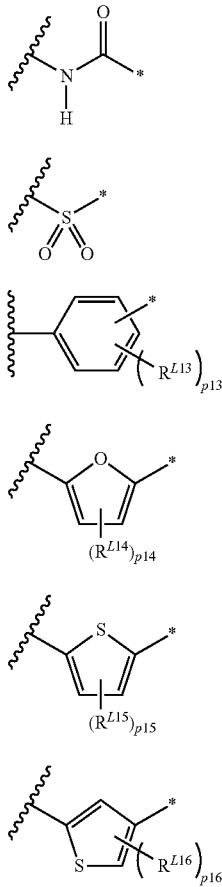

(L-11)

(L-12)

(L-13)

(L-14)

(L-15)

(L-16)

wherein, in Formulae L-1 to L-16, * and wavy line portions represent bonding positions to other structures, p13 represents an integer of 0 to 4, p14, p15, and p16 each independently represent an integer of 0 to 2, $R^{L1}$, $R^{L21}$, $R^{L22}$, $R^{L13}$, $R^{L14}$, $R^{L15}$, and $R^{L16}$ each independently represent a hydrogen atom or a substituent.

17. The composition for forming an organic semiconductor film according to claim 16, wherein all of $Z^{1a}$ to $Z^{1j}$ are hydrogen atoms.

18. The composition for forming an organic semiconductor film according to claim 16, wherein n1 is 0.

19. The composition for forming an organic semiconductor film according to claim 16, wherein at least one of p1 or q1 is not 0.

20. The composition for forming an organic semiconductor film according to claim 16, wherein:
   at least one of p1 or q1 is not 0, and
   at least one of $R^{11}$ or $R^{12}$ is a group represented by Formula W.

21. The composition for forming an organic semiconductor film according to claim 16, wherein p1 and q1 is 1.

22. The composition for forming an organic semiconductor film according to claim 16, wherein both of $X^{11}$ and $X^{12}$ are S atoms, $A^{11}$ is =$CR^{411}$—, and $A^{12}$ is =$CR^{412}$—.

23. The composition for forming an organic semiconductor film according to claim 16, wherein the compound represented by Formula 1 is a compound represented by Formula 2 below:

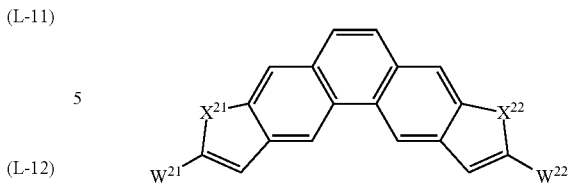

wherein, in Formula 2, $X^{21}$ and $X^{22}$ each independently represent a chalcogen atom, $W^{21}$ and $W^{22}$ each independently represent a group represented by Formula W.

24. The composition for forming an organic semiconductor film according to claim 16, wherein the compound represented by Formula 1 is a line symmetric structure.

25. The composition for forming an organic semiconductor film according to claim 16, wherein the number of carbon atoms in the group represented by Formula W is 5 to 40.

26. The composition for forming an organic semiconductor film according to claim 16, wherein $L^W$ is a single bond, a divalent linking group represented by any one of Formulae L-1 to L-4 and Formulae L-13 to L-16, and a divalent linking group obtained by bonding two or more divalent linking groups represented by any one of Formulae L-1 to L-4 and Formulae L-13 to L-16.

27. The composition for forming an organic semiconductor film according to claim 16, wherein $L^W$ is a single bond or a divalent linking group represented by any one of Formulae L-1 to L-4 and Formulae L-13 to L-16.

28. The composition for forming an organic semiconductor film according to claim 16, wherein $S^W$ is a single bond.

29. The composition for forming an organic semiconductor film according to claim 16, wherein $L^W$ is a single bond or a divalent linking group represented by any one of Formula L-1 and Formulae L-13 to L-16.

30. The composition for forming an organic semiconductor film according to claim 16, wherein $T^W$ is an alkyl group.

31. The composition for forming an organic semiconductor film according to claim 16, wherein a group represented by Formula W is an alkyl group.

32. The composition for forming an organic semiconductor film according to claim 16, further comprising:
   a binder polymer,
   wherein a content of the binder polymer is 10 mass % or less with respect to a total amount of the composition for forming an organic semiconductor film.

33. A compound represented by Formula 1 below:

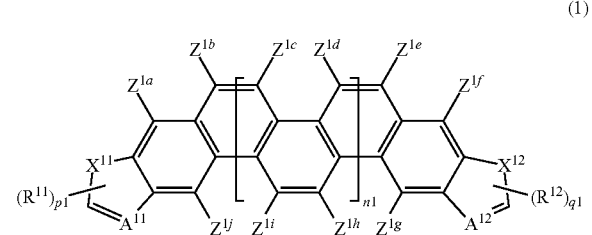

wherein, in Formula 1, $X^{11}$ and $X^{12}$ each independently represent a chalcogen atom, $Z^{1a}$ to $Z^{1j}$ each independently represent a hydrogen atom or a halogen atom, $A^{11}$ represents =$CR^{411}$— or a nitrogen atom, $R^{411}$ represents a hydrogen atom or a group represented by $R^{11}$, $A^{12}$ represents =$CR^{412}$— or a nitrogen atom, $R^{412}$ represents a hydrogen atom or a group represented by $R^{12}$, n1 represents 0 or 1, p1 represents an integer of 0 to 2 in a case where $A^{11}$ is =$CR^{A11}$— and represents 0 or 1 in a case where $A^{11}$ is a nitrogen atom, q1 represents an integer of 0 to 2 in a case where $A^{12}$ is =$CR^{A12}$— and represents 0 or 1 in a case where $A^{12}$ is a nitrogen atom, at least one of p1 or q1 is not 0, $R^{11}$ and $R^{12}$ each independently represent a halogen atom, an aryl group, a heteroaryl group, or a group represented by Formula W below:

$$-S^W-L^W-T^W \quad (W)$$

wherein, in Formula W, $S^W$ represents a single bond or an alkylene group represented by —$(CR^S_2)_k$—, $R^S$ each independently represent a hydrogen atom or a halogen atom, k represents an integer of 1 to 17, $L^W$ represents a single bond, a divalent linking group represented by any one of Formulae L-1 to L-16 below, or a group obtained by bonding any two or more of divalent linking groups represented by Formulae L-1 to L-16 below, $T^W$ represents an alkyl group, a cyano group, a vinyl group, an ethynyl group, an aryl group, a heteroaryl group, an oxyethylene group, an oligooxyethylene group of which the repetition number of oxyethylene units is two or greater, an oligosiloxane group having two or more silicon atoms, or a trialkylsilyl group, and

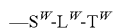

(L-1)

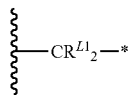

(L-2)

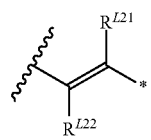

(L-3)

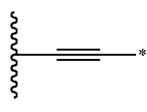

(L-4)

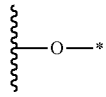

(L-5)

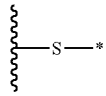

(L-6)

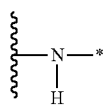

(L-7)

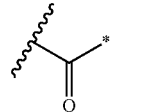

(L-8)

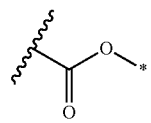

-continued

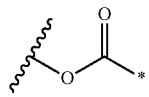

(L-9)

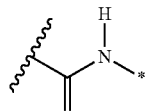

(L-10)

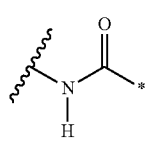

(L-11)

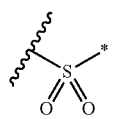

(L-12)

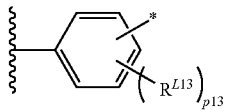

(L-13)

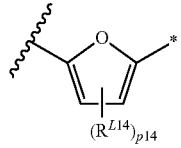

(L-14)

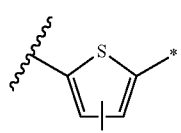

(L-15)

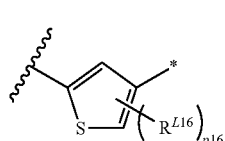

(L-16)

wherein, in Formulae L-1 to L-16, * and wavy line portions represent bonding positions to other structures, p13 represents an integer of 0 to 4, p14, p15, and p16 each independently represent an integer of 0 to 2, $R^{L1}$, $R^{L21}$, $R^{L22}$, $R^{L13}$, $R^{L14}$, $R^{L15}$, and $R^{L16}$ each independently represent a hydrogen atom or a substituent.

34. A method of manufacturing an organic semiconductor film, comprising:
    an applying step of applying the composition for forming an organic semiconductor film according to claim 16 to a substrate, and
    a removing step of removing at least a portion of the solvent having a boiling point of 100° C. or higher included in the composition for forming an organic semiconductor film.

35. The method of manufacturing the organic semiconductor film according to claim 34, wherein the applying step is performed by an ink jet method or a flexographic printing method.

36. An organic semiconductor film comprising the compound according to claim 33.

37. A method of manufacturing an organic semiconductor element, comprising:
- an applying step of applying the composition for forming an organic semiconductor film according to claim 16 to a substrate, and
- a removing step of removing at least a portion of the solvent having a boiling point of 100° C. or higher included in the composition for forming an organic semiconductor film.

38. The method of manufacturing the organic semiconductor element according to claim 37, wherein the applying step is performed by an ink jet method or a flexographic printing method.

39. An organic semiconductor element comprising the compound according to claim 33.

* * * * *